(12) United States Patent
Marziali et al.

(10) Patent No.: US 9,340,835 B2
(45) Date of Patent: May 17, 2016

(54) METHOD FOR SEPARATING HOMODUPLEXED AND HETERODUPLEXED NUCLEIC ACIDS

(71) Applicants: Boreal Genomics Corp., Mountain View, CA (US); The University of British Columbia, Vancouver (CA)

(72) Inventors: Andrea Marziali, North Vancouver (CA); Joel Pel, Vancouver (CA)

(73) Assignees: Boreal Genomics Corp., Vancouver, BC (CA); The University Of British Columbia, Vancouver, BC (CA)

(*) Notice: Subject to any disclaimer, the term of this patent is extended or adjusted under 35 U.S.C. 154(b) by 159 days.

(21) Appl. No.: 14/210,696

(22) Filed: Mar. 14, 2014

(65) Prior Publication Data

US 2014/0274737 A1    Sep. 18, 2014

Related U.S. Application Data

(60) Provisional application No. 61/791,001, filed on Mar. 15, 2013.

(51) Int. Cl.
    *C12P 19/34* (2006.01)
    *C12Q 1/68* (2006.01)

(52) U.S. Cl.
    CPC ............ *C12Q 1/6886* (2013.01); *C12Q 1/6827* (2013.01); *C12Q 2600/156* (2013.01)

(58) Field of Classification Search
    USPC .............................................. 506/2; 435/6.12
    See application file for complete search history.

(56) References Cited

U.S. PATENT DOCUMENTS

| | | | |
|---|---|---|---|
| 4,148,703 A | 4/1979 | Trop et al. | |
| 4,390,403 A | 6/1983 | Batchelder | |
| 4,390,404 A | 6/1983 | Esho et al. | |
| 4,732,656 A | 3/1988 | Hurd | |
| 4,911,817 A | 3/1990 | Kindlmann | |
| 4,971,671 A | 11/1990 | Slater et al. | |
| 5,084,157 A | 1/1992 | Clark et al. | |
| 5,185,071 A | 2/1993 | Serwer et al. | |
| 5,286,434 A | 2/1994 | Slater et al. | |
| 5,384,022 A | 1/1995 | Rajasekaran | |
| 5,453,162 A | 9/1995 | Sabanayagam et al. | |
| 5,609,743 A | 3/1997 | Sasagawa et al. | |
| 5,641,628 A | 6/1997 | Bianchi | |
| 5,938,904 A | 8/1999 | Bader et al. | |
| 6,036,831 A | 3/2000 | Bishop | |
| 6,110,670 A | 8/2000 | Van Broeckhoven et al. | |
| 6,146,511 A | 11/2000 | Slater et al. | |
| 6,193,866 B1 | 2/2001 | Bader et al. | |
| 6,258,540 B1 | 7/2001 | Lo et al. | |
| 6,693,620 B1 | 2/2004 | Herb et al. | |
| 6,824,664 B1 | 11/2004 | Austin et al. | |
| 6,827,830 B1 | 12/2004 | Slater et al. | |
| 6,893,546 B2 | 5/2005 | Jullien et al. | |
| 6,927,028 B2 | 8/2005 | Dennis et al. | |
| 7,175,747 B2 | 2/2007 | Bayerl et al. | |
| 7,198,702 B1 | 4/2007 | Washizu et al. | |
| 7,371,533 B2 | 5/2008 | Slater et al. | |
| 7,427,343 B2 | 9/2008 | Han et al. | |
| 7,442,506 B2 | 10/2008 | Dhallan | |
| 7,452,668 B2 | 11/2008 | Boles et al. | |
| 7,838,647 B2 | 11/2010 | Hahn et al. | |
| 7,888,017 B2 | 2/2011 | Quake et al. | |
| 7,960,159 B2* | 6/2011 | Barany .................. C12Q 1/683 435/199 |
| 8,008,018 B2 | 8/2011 | Quake et al. | |
| 8,119,339 B2* | 2/2012 | Philpott ................. C12Q 1/703 435/325 |
| 8,133,371 B2 | 3/2012 | Marziali et al. | |
| 8,182,666 B2 | 5/2012 | Marziali et al. | |
| 8,195,415 B2 | 6/2012 | Fan et al. | |
| 8,480,871 B2* | 7/2013 | Marziali ................ B01D 57/02 204/457 |
| 8,518,228 B2* | 8/2013 | Marziali ............ G01N 33/5308 204/457 |
| 8,529,744 B2* | 9/2013 | Marziali .......... G01N 27/44713 204/457 |
| 8,877,028 B2* | 11/2014 | Marziali ............ G01N 21/6428 204/457 |
| 9,011,661 B2* | 4/2015 | Marziali .......... G01N 27/44713 204/457 |
| 2001/0045359 A1 | 11/2001 | Cheng et al. | |
| 2002/0036139 A1 | 3/2002 | Becker et al. | |
| 2002/0081280 A1 | 6/2002 | Curiel et al. | |
| 2002/0119448 A1 | 8/2002 | Sorge et al. | |
| 2002/0179445 A1 | 12/2002 | Alajoki et al. | |
| 2003/0027178 A1 | 2/2003 | Vasmatzis et al. | |
| 2003/0215855 A1 | 11/2003 | Dubrow et al. | |
| 2005/0164241 A1 | 7/2005 | Hahn et al. | |
| 2005/0164402 A1 | 7/2005 | Belisle et al. | |
| 2005/0247563 A1 | 11/2005 | Shuber et al. | |

(Continued)

FOREIGN PATENT DOCUMENTS

CA    2 552 262 A1    8/2005
CA    2 523 089 A1    4/2006

(Continued)

OTHER PUBLICATIONS

Jorgez et al., 2009, Improving Enrichment of Circulating Fetal DNA for Genetic Testing: Size Franctionation Followed by Whole Gene Amplification, Fetal Diagn. Ther 25:314-319.

(Continued)

*Primary Examiner* — Kenneth Horlick
(74) *Attorney, Agent, or Firm* — Brown Rudnick LLP

(57) ABSTRACT

The invention includes methods and apparatus for separating heteroduplexed nucleic acids from homoduplexed nucleic acids having similar sequences and being at a much higher concentration. The heteroduplexed nucleic acids may be separated through the application of a time varying driving field and a time-varying mobility field to a sample of heteroduplexed and homoduplexed nucleic acids in a separation medium. Once the heteroduplexed nucleic acids are isolated and recovered, it is straightforward to analyze the sequences of the heteroduplexed nucleic acids, e.g., using sequencing or hybrid assays.

20 Claims, 26 Drawing Sheets

(56) References Cited

U.S. PATENT DOCUMENTS

| | | | |
|---|---|---|---|
| 2005/0247564 | A1 | 11/2005 | Volkel et al. |
| 2007/0215472 | A1 | 9/2007 | Slater et al. |
| 2007/0218494 | A1 | 9/2007 | Slater et al. |
| 2008/0108063 | A1 | 5/2008 | Lucero et al. |
| 2008/0314751 | A1 | 12/2008 | Bukshpan et al. |
| 2009/0026082 | A1 | 1/2009 | Rothberg et al. |
| 2009/0120795 | A1 | 5/2009 | Marziali et al. |
| 2009/0127589 | A1 | 5/2009 | Rothberg et al. |
| 2009/0139867 | A1 | 6/2009 | Marziali et al. |
| 2009/0152116 | A1 | 6/2009 | Boles et al. |
| 2010/0035252 | A1 | 2/2010 | Rothberg et al. |
| 2010/0137143 | A1 | 6/2010 | Rothberg et al. |
| 2010/0188073 | A1 | 7/2010 | Rothberg et al. |
| 2010/0197507 | A1 | 8/2010 | Rothberg et al. |
| 2010/0273219 | A1 | 10/2010 | May et al. |
| 2010/0282617 | A1 | 11/2010 | Rothberg et al. |
| 2010/0285537 | A1 | 11/2010 | Zimmermann |
| 2010/0300559 | A1 | 12/2010 | Schultz et al. |
| 2010/0300895 | A1 | 12/2010 | Nobile et al. |
| 2010/0301398 | A1 | 12/2010 | Rothberg et al. |
| 2010/0304982 | A1 | 12/2010 | Hinz et al. |
| 2011/0048950 | A1 | 3/2011 | Marziali et al. |
| 2011/0152111 | A1 | 6/2011 | Fan et al. |
| 2011/0245482 | A1 | 10/2011 | Hahn et al. |
| 2011/0272282 | A1 | 11/2011 | Marziali et al. |
| 2012/0035062 | A1 | 2/2012 | Schultz et al. |
| 2012/0048735 | A1 | 3/2012 | Marziali et al. |
| 2012/0160682 | A1 | 6/2012 | Marziali et al. |
| 2012/0199481 | A1 | 8/2012 | Marziali et al. |

FOREIGN PATENT DOCUMENTS

| | | | |
|---|---|---|---|
| CA | 2 496 294 | A1 | 8/2006 |
| CA | 2 641 326 | A1 | 8/2006 |
| CA | 2 713 313 | A1 | 8/2009 |
| CA | 2 742 460 | A1 | 5/2010 |
| EP | 0 356 187 | A2 | 2/1990 |
| EP | 1720636 | A1 | 11/2006 |
| EP | 1859249 | | 11/2007 |
| EP | 2238434 | | 10/2010 |
| EP | 2 458 004 | A1 | 5/2012 |
| GB | 2 249 395 | A | 5/1992 |
| JP | 7-167837 | A | 7/1995 |
| JP | 2000-505545 | A | 5/2000 |
| JP | 2001-165906 | A | 6/2001 |
| JP | 2002-502020 | A | 1/2002 |
| JP | 2003-062401 | A | 3/2003 |
| JP | 2003-066004 | A | 3/2003 |
| JP | 2003-513240 | A | 4/2003 |
| JP | 2003-215099 | A | 7/2003 |
| JP | 2003-247980 | A | 9/2003 |
| WO | 95/14923 | A1 | 6/1995 |
| WO | 97/27933 | A1 | 8/1997 |
| WO | 99/38874 | A2 | 8/1999 |
| WO | 99/45374 | A2 | 9/1999 |
| WO | 01/31325 | A | 5/2001 |
| WO | 02/42500 | A2 | 5/2002 |
| WO | 03/019172 | A2 | 3/2003 |
| WO | 2005/072854 | A1 | 8/2005 |
| WO | 2006/063625 | A1 | 6/2006 |
| WO | 2006/081691 | A1 | 8/2006 |
| WO | 2007/092473 | A2 | 8/2007 |
| WO | 2009/094772 | A1 | 8/2009 |
| WO | 2010/051649 | A1 | 5/2010 |
| WO | 2010/104798 | A1 | 9/2010 |
| WO | 2010/121381 | A1 | 10/2010 |
| WO | 2013/002616 | A2 | 1/2013 |

OTHER PUBLICATIONS

Varley et al., 2008, Nested Patch PCR enables highly multiplexed mutation discovery in candidate genes, Genome Res. 18:1844-1850.
Margulies, M., et al., "Genome sequencing in microfabricated high-density picolitre reactors", Nature 437, 376-380 (Sep. 15, 2005).
Anonymous, "Nucleic Acid Purification + Technical Presentation," Boreal Genomics, http://www.borealgenomics.com/technology/purification/, Jan. 24, 2010.
Asbury, et al., "Trapping of DNA by dielectrophoresis", Electrophoresis, 2002, 23:2658-2666.
Asbury, et al., "Trapping of DNA in Nonuniform Oscillating Electric Fields", Biophysical Journal, 1998, 74:1024-1030.
Astumian, et al., "Fluctuation Driven Ratchets: Molecular Motors", Physical Review Letters, 1994, 72(11):1766-1769.
Baba, Yoshinobu, "Capillary Affinity Gel Electrophoresis", Molecular Biotechnology, 1996, (9):1-11.
Bier, Martin, et al., "Biasing Brownian Motion in Different Directions in a 3-State Fluctuating Potential and an Application for the Separation of Small Particles", Physical Review Letters, 1996, 76(22):4277-4280.
Broemeling, D., et al., "An Instrument for Automated Purification of Nucleic Acids from Contaminated Forensic Samples", JALA 2008, 13, 40-48.
Carle, G.F., et al., "Electrophoretic Separations of Large DNA Molecules by Periodic Inversion of the Electric Field", Science, 1986, 232(4726):65-68.
Chacron, M.J., et al., "Particle trapping and self-focusing in temporarily asymmetric ratchets with strong field gradients", Physical Review E, 1997, 56(3):3446-3450.
Chakrabarti, Subrata, et al., "Highly Selective Isolation of Unknown Mutations in Diverse DNA Fragments: Toward New Multiplex Screening in Cancer", American Association for Cancer Reserch, 2000, 60:3732-3737.
Chan, K.C. Allen, et al., "Size Distributions of Maternal and Fetal DNA in Maternal Plasma", Molecular Diagnostics and Genetics, Clinical Chemistry, 2004, 50(1):88-92.
Chu, Gilbert, "Bag model for DNA migration during pulsed-field electrophoresis", Proc. Natl. Acad. Sci., 1991, 88:11071-11075.
European Search Report corresponding to EP11004417, Mar. 29, 2012, 4 pages.
Frumin, L.L., et al., "Anomalous size dependence of the non-linear mobility of DNA", In PhysChemComm, 2000, 11 (3):61-63.
Frumin, L.L., et al., "Nonlinear focusing of DNA macromolecules", Physical Review E—Statistical, Nonlinear and Soft Matter Physics, 2001, 64:021902-1-5.
Griess, Gary A., et al., "Cyclic capillary electrophoresis", Electrophoresis, 2002, 23:2610-2617.
International Preliminary Report on Patentability corresponding to PCT/CA2005/000124, Aug. 7, 2006, 8 pages.
International Preliminary Report on Patentability corresponding to PCT/CA2006/000172, Aug. 7, 2007, 8 pages.
International Preliminary Report on Patentability corresponding to PCT/CA2009/000111, Aug. 3, 2010, 9 pages.
International Seach Report and Written Opinion for PCT/US13/39553 dated Sep. 18, 2013, pp. 13.
International Search Report dated Feb. 23, 2010 corresponding to PCT/CA2009/001648, 6 pages.
International Search Report for PCT/CA2006/000172, International Searching Authority, Jun. 2, 2006, 4 pages.
International Search Report for PCT/CA2012/050576, Feb. 28, 2013 3 pages.
Jorgez, Carolina J., et al., "Quantity versus quality: Optimal methods for cell-free DNA isolation from plasma of pregnant women", American College of Medical Genetics, 2006, 8(10):615-619.
Kitzman, Jacob O., et al., "Noninvasive Whole-Genome Sequencing of a Human Fetus", Sci Transl Med 4, 137ra76 (2012); DOI: 10.1126/scitranslmed.3004323, 9 pages.
Kopecka, K., et al., "Capillary electrophoresis sequencing of small ssDNA molecules versus the Ogston regime: Fitting data and interpreting parameters", Electrophoresis, 2004, 25(14):2177-2185.
LaLande, Marc, et al., "Pulsed-field electrophoresis: Application of a computer model to the separation of large DNA molecules", Proc. Natl. Acad. Sci. USA, 1987, 84:8011-8015.
Lun, Fiona M. F., et al., "Microfluidics Digital PCR Reveals a Higher than Expected Fraction of Fetal DNA in Maternal Plasma", Molecular Diagnostics and Genetics, Clinical Chemistry, 2008, 54(10):1664-1672.

(56) References Cited

OTHER PUBLICATIONS

Magnasco, Marcelo, O., "Forced Thermal Ratchets", Physical Review Letters, 1993, 71(10):1477-1481.

Makridakis, Nick M., "PCR-free method detects high frequency of genomic instability in prostate cancer", Nucleic Acids Research, 2009, 37(22):7441-7446.

Marziali, A., et al., "Novel electrophoresis mechanism based on synchronous alternating drag perturbation", Electrophoresis 2005, 26:82-90, published on-line Dec. 29, 2004 at URL www.3.interscience.wiley.com/cgi-bin/issue/109861245.

Nollau, Peter, et al., "Methods for detection of point mutations: performance and quality assessment", Department of Clinical Chemistry, 1997, 43(7):1114-1128.

Office Action mailed Aug. 19, 2011 for U.S. Appl. No. 11/815,760.

Office Action mailed Dec. 27, 2010 for U.S. Appl. No. 11/815,760.

Pel, J., "A novel electrophoretic mechanism and separation parameter for selective nucleic acid concentration based on synchronous coefficient of drag alteration (SCODA)", (Ph.D. Thesis), Vancouver: University of British Columbia, 2009.

Pel, J., et al., "Nonlinear electrophoretic response yields a unique parameter for separation of biomolecules", PNAS 2009, vol. 106, No. 35, 14796-14801.

Rousseau, J., et al., "Gel electrophoretic mobility of single-stranded DNA: The two reptation field-dependent factors", Electrophoresis, 2000, 21(8):1464-1470.

Sikora, Aleksandra, et al., "Detection of Increased Amounts of Cell-Free DNA with Short PCR Amplicons", Clinical Chemistry, 2010, 56(1):136-138.

Slater, G.W., et al., "Recent developments in DNA electrophoretic separations", Electrophoresis, 1998, 19 (10):1525-1541.

Slater, G.W., et al., "The theory of DNA separation by capillary electrophoresis", Current Opinion in Biotechnology, 2003, 14:58-64.

Slater, G.W., et al., "Theory of DNA electrophoresis: A look at some current challenges", Electrophoresis, 2000, 21:3873-3887.

So. A., et al., "Efficient genomic DNA extraction from low target concentration bacterial cultures using SCODA DNA extraction technology", Cold Spring Harb Protoc, 2010, 1150-1153; 1185-1198.

Supplementary European Search Report corresponding to EP09706657, May 12, 2011, 2 pages.

Supplementary Partial European Search Report corresponding to EP05706448, May 14, 2012, 3 pages.

Tessier, F., et al., "Strategies for the separation of polyelectrolytes based on non-linear dynamics and entropic ratchets in a simple microfluidic device", Applied Physics A—Materials Science & Processing, 2002, 75:285-291.

Thompson, J.D., et al., "Winnowing DNA for Rare Sequences: Highly Specific Sequence and Methylation Based Enrichment," PLOS One, vol. 7, No. 2, Feb. 15, 2012.

Turmel, C., et al., "Molecular detrapping and band narrowing with high frequency modulation of pulsed field electrophoresis", Nucleic Acids Research, 1990, 18(3):569-575.

Viovy, J.L., "Electrophoresis of DNA and other polyelectrolytes: Physical mechanisms", Review of Modern Physics, 2000, 72(3):813-872.

Wright, Caroline, "Cell-free fetal nucleic acids for non-invasive prenatal diagnosis", Report of the UK export working group, Jan. 2009, 64 pages.

Yobas, L., et al., "Nucleic Acid Extraction, Amplification, and Detection on Si-Based Microfluidic Platforms," IEEE Journal of Solid-State Circuits, vol. 42, No. 8, Aug. 2007, 12 pages.

* cited by examiner

METHOD FOR SEPARATING HOMODUPLEXED AND HETERODUPLEXED NUCLEIC ACIDS

RELATED APPLICATION

This application claims priority to U.S. Provisional Application No. 61/791,001, filed Mar. 15, 2013, which is incorporated by reference in its entirety.

TECHNICAL FIELD

The invention relates to methods and apparatus for isolating mutations in nucleic acids, especially unknown mutations. The invention also relates to enriching a sample for nucleic acid mutations as part of a diagnostic workflow.

BACKGROUND

Standard nucleic acid separation techniques limit researchers' abilities to analyze samples for nucleic acids that are present in low abundance, such as mutations. In particular, it is difficult to resolve rare nucleic acids that are present at low concentrations in the presence of closely-related nucleic acids, e.g., wild-type DNA.

In order to resolve rare mutations in a sample, all of the nucleic acids in a sample are typically amplified prior to isolation and analysis. For example, using Polymerase Chain Reaction (PCR) amplification, each nucleic acid in a sample can be amplified one million times (or more). Theoretically, there will be a million-fold increase of each nucleic acid originally present, and, thus, a greater opportunity to isolate and find the nucleic acids in low abundance. In practice, however, PCR amplification has significant drawbacks when used to amplify nucleic acids that are present in low abundance. The PCR reaction is stochastic, and to the extent that a low-abundance nucleic acid is not amplified in the first few rounds of PCR, it likely will not be detected. In addition, PCR amplification introduces sequence errors in the amplicons because of the lack of fidelity in the polymerases used. In some systems, PCR and/or sequencing errors can result in error rates on the order of 0.1% or higher. If the error rate is greater than or equivalent to the mutation rate in a system, it is difficult to reliably detect the mutations in the system.

An additional shortcoming of PCR amplification is that at least a portion of the sequence of interest must be known prior to the amplification. During the amplification process, a primer having a sequence at least partially complementary to the target is used to begin amplicon construction. The primer need not be exactly complementary to the mutation, but it must be similar enough to prompt a polymerase to copy the region of interest. When a known mutation is sought, the sequence of the corresponding primer is easily determined, and nucleic acids can be reliably amplified, subject to the shortcoming discussed above. When an unknown mutation is present, however, it is possible that the selected primers will not hybridize with the unknown mutation. If the primers do not hybridize with the unknown mutation, the mutation will not be amplified, and it is very unlikely that the unknown mutation will be later identified in the presence of millions-fold excesses of known mutations. Furthermore, if the unknown mutation is only a matter of one or two base changes, it is impossible to distinguish the mutation from an error introduced by the amplification process itself.

There is a need for techniques that easily separate closely-related mutations without introducing errors into the sample. There is also a need for techniques to isolate unknown mutations in a nucleic acid sample.

SUMMARY OF THE INVENTION

The invention is a method to separate mutant nucleic acids, including both known and unknown mutants, or epigenetic changes from wild-type nucleic acids. In particular, using the methods of the invention, heteroduplexed nucleic acid strand pairings can be isolated and recovered from a sample having a vast majority of homoduplexed nucleic acid strand pairings of the same size and similar sequence. The mutants may vary from the wild-type sequences by having one or more base pair polymorphisms, insertions, or deletions. The mutants may be present at a concentration of 0.1% or less compared to the wild-type nucleic acids. Additionally, using the disclosed apparatus, the isolated heteroduplexes are recovered in a concentrated aqueous product, making additional analysis, e.g., sequencing, quite straightforward.

The methods of the invention are well-suited for the isolation of mutations in oncogenes, e.g., for the detection of cancer, cancer typing, or to determine the progression of cancer in humans. Typically a sample from a subject, such as blood, urine, or tissue, is processed to isolate nucleic acids, and the nucleic acids are amplified with primers selected to facilitate amplification of oncogenes of interest (including both wild-type and mutant sequences). The amplified products are then denatured and allowed to re-anneal to create a population of homoduplexes and heteroduplexes having sequences related to the oncogenes. The heteroduplexed nucleic acids are then separated from the homoduplexed nucleic acids and the heteroduplexes sequenced, giving key information about the type and amounts of mutations in the oncogene in the sample.

In another aspect, the invention provides methods for recovering mutant nucleic acids from a sample by enriching the sample for heteroduplexes containing the mutant nucleic acid species. Methods of the invention are fundamentally different from conventional separation techniques in that methods of the invention create a subsample in which a mutant that was present in only a small amount in the original sample becomes the dominant nucleic acid species in the subsample. Furthermore, in some samples, it is not necessary to know the locus of the mutation prior to performing the enrichment. As a result, unknown mutations are readily separated for further analysis. Such techniques are especially useful in rapidly isolating mutated sequences in pathogens, e.g., pathogenic bacteria or viruses.

The invention provides the additional benefit of allowing isolation and recovery of rare mutations without the need to amplify a sample prior to the isolation, thereby reducing the likelihood that mutations detected at low concentration are merely transcription errors introduced during amplification, e.g., PCR. Furthermore, because the technique can isolate both the homoduplexes or the heteroduplexes, the technique lends itself to assessing a ratio of wild-type to mutant sequences in addition to the ratio of various mutants. Such information can be used to identify the stage of a disease, e.g., cancer, and/or to evaluate the efficacy of a treatment for the disease, e.g., chemotherapy.

While the invention is fundamentally different from well-known techniques such as slab electrophoresis and PCR amplification, the invention provides many of the same advantages (high specificity, high sensitivity, and high speed) without the drawbacks of those techniques (sample loss, introduction of errors, high cost). This fidelity allows the mutant nucleic acids to be directly sequenced using next generation sequencing. Alternatively, the enriched mutant nucleic acids can be amplified after enrichment, prior to further processing, e.g., sequencing.

Further aspects of the invention and features of specific embodiments of the invention are described below.

DESCRIPTION

Figure 1A:
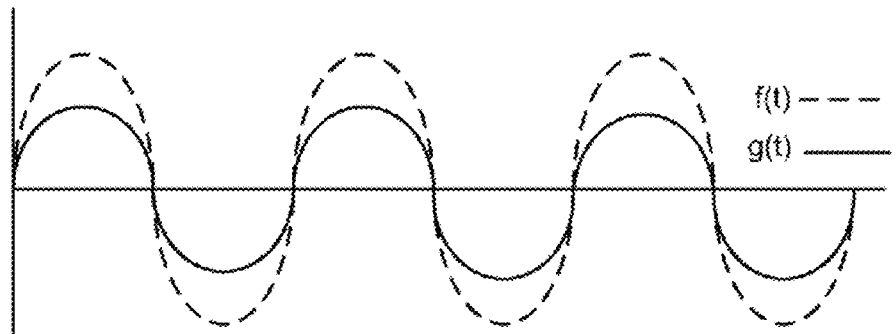
FIG. 1A shows an exemplary waveform for driving and mobility-modifying fields.

The invention includes methods and apparatus for isolating mutant nucleic acids, especially in the form of heteroduplexed and homoduplexed nucleic acid strand pairings. Typically a sample comprising an abundance of wild-type and mutant nucleic acids will be denatured with mixing and subsequently cooled to allow heteroduplexed nucleic acids to form. The heteroduplexed nucleic acids are then separated from the population of homoduplexed (primarily wild-type) nucleic acids, allowing the heteroduplexes to be analyzed. The post-separation analysis may include amplification and sequencing. Accordingly, the invention is a powerful bioanalytical tool that can be used for advanced separation or used as part of a diagnostic or research workflow.

Methods of the invention additionally provide the ability to isolate low-abundance biological molecules, such as mutant nucleic acids, from a sample. The invention provides for enriching low-abundance variants of a biological molecule relative to more common, or wild-type, variants of the molecule. In preferred embodiments, methods of the invention are used to create a subsample in which a mutant that was present in the original sample in low-abundance relative to a more common species (e.g., a mutated nucleic acid and its wild-type equivalent) is present in relative high abundance in the subsample.

Typically, the methods of the invention are used on a mixture of heteroduplexed and homoduplexed nucleic acid strand pairings resulting from targeted amplification of a gene of interest. In an embodiment, nucleic acids from a sample, e.g., genomic DNA, are amplified with primers targeted for a sequence of interest. After a few amplification cycles, e.g., two or more amplification cycles, e.g., three or more amplification cycles, e.g., four or more amplification cycles, e.g., less than five amplification cycles, the amplicons are denatured, mixed, and reannealed to create a mixture of homoduplexed and heteroduplexed nucleic acid strand pairings. Because of the sample statistics prior to the denaturing and reannealing, the homoduplexed nucleic acids will typically comprise two wild-type sequences and the heteroduplexed nucleic acids will comprise one wild-type and one mutant sequence, although other configurations are possible. The sample may be any biological sample comprising nucleic acids, such as blood, plasma, sweat, saliva, sputum, urine, stool, tears, hair, tissue, exhaled breath, or a buccal swab. In some instances, the invention allows resolution of different nucleic acids without amplification in the isolating step and without regard for the sequence difference between a nucleic add and a variant of it.

Accordingly, use of the invention allows detection and analysis of nucleic acids present in low abundance in biological samples. The ability to interrogate low-abundance nucleic acids is especially important in cancer diagnostics, where early detection enables effective treatment. For example, identification of the presence of a specific mutation may suggest a particular treatment regimen (e.g., surgery versus radiation therapy) or suggest that a first line treatment is likely to be ineffective, (e.g., the cancer is resistant to docetaxel). Additionally, when mutational events are detected earlier, patients typically have more options for treatment, as well as the time to identify a preferred treatment provider.

Methods of the invention are useful in many types of samples. Preferred samples are derived from tissue or body fluid, for example, tissues, blood, sputum, sweat, urine, tears, feces, aspirates, or a combination thereof. Typically, the biological sample will be from a human, however the methods of the invention may be used to recover nucleic acids from many organisms, including, mammals. In other applications, the methods can be used to identify variations in organism such as plants, fungi, bacteria, or viruses. Thus, the invention allows for rapid detection of mutations that may be responsible for crop failures, epidemics, or a biological weapon attack.

Once a sample is enriched for a target, it will typically be useful to identify the target using sequencing, hybrid capture, antibodies or other known techniques. Once the target nucleic acid is identified, it will be possible to correlate its presence in the sample with a condition, or a likely outcome for the subject from which the sample was taken. For example, the presence of the target nucleic acid may be indicative of a genetic disorder or cancer. Additionally, because the methods of the invention can be used to enrich a sample for multiple targets (serially or in parallel), the invention lends itself to diagnosing diseases by identifying specific biomarker panels that correlate with specific diseases. In some instances the invention will allow the identification of 5 or more targets, e.g., 10 or more targets, e.g., 20 or more targets, e.g., 50 or more targets, e.g., 100 or more targets. Furthermore, when screening panels comprising multiple biomarkers are used, the confidence in the resulting diagnosis is increased. That is, a diagnosis based upon identifying one target nucleic acid may be the result of noise or error, but when a diagnosis is based upon identifying 10 or more targets simultaneously, it is very likely not the result of noise or error.

The skilled artisan will appreciate that there are numerous ways to practice the invention described and claimed herein. However, one preferred embodiment is exemplified below using a technique called scodaphoresis or SCODA (Synchronous Coefficient of Drag Alteration). Scodaphoresis refers to methods for moving and/or concentrating particles in a medium. Scodaphoresis involves exposing particles that are to be moved and/or concentrated to two time-varying fields or stimuli. A first one of the fields results in a force f(t) that drives motion of the particles in the medium. The direction of particle motion caused by the interaction of the particle with the first field varies in time. The first field may provide a driving force that averages to zero over an integral number of cycles of the first field.

A second one of the fields alters the mobility of the particles in the medium according to a function g(t). The first and second fields are such that f(t) and g(t) have a non-zero correlation over a time period of interest. Achieving such a non-zero correlation can be achieved in various ways. In some embodiments, f(t) and g(t) are each time varying at the same frequency and f(t) and g(t) are synchronized so that there is a substantially constant phase relationship between f(t) and g(t). In other embodiments, f(t) has a frequency that is twice that of g(t).

Application of the fields to the particles causes a net drift of the particles. This net drift can be harnessed to separate particles of different types or to concentrate (enrich) particles in selected areas, or both. As discussed below, the first and second fields may be of the same type (homogeneous SCODA) or of different types (heterogeneous SCODA).

As a demonstration of SCODA, consider the case where:

$$f(t)=\sin(\omega t), g(t)=\sin(\omega t), \text{ and } v(f(t),g(t))= f(t)\times(\mu_0+\mu_1 g(t)) \quad (1)$$

where $\mu_0$, is the unperturbed mobility of the particle in the medium and $\mu_1$ is the susceptibility of the mobility to g(t). It can be seen that in the absence of g(t), the velocity of the particle is given simply by $\mu_0 f(t)$. Where f(t) is given by Equation (1) there is no net displacement of the particle over a cycle of f(t). Where g(t) is as given above, however, over one cycle, the velocity integrates to yield a distance, d, traveled by the particle of:

$$d = \int_{t=0}^{2\pi/\omega} \mu_1 \sin^2(\omega t) dt = \frac{\mu_1 \pi}{\omega} \quad (2)$$

Thus, the simultaneous application of the two fields imparts a net motion to the particle. In this example, the net motion is independent of $\mu_0$.

"Particle" is used herein to mean any microscopic or macroscopic thing that can be moved by scodaphoresis.

The correlation of f(t) and g(t) may be computed according to a suitable correlation function such as:

$$C_{f(t),g(t)} = \int_T f(t)g(t+\lambda)dt \tag{3}$$

where C is the correlation, T is a period of interest, and $\lambda$ is a constant time shift. C must have a non-zero value for some value of $\lambda$.

Ideally f(t) and g(t) have a large correlation for efficient operation of SCODA, but some SCODA motion can occur even in cases where the chosen functions f(t) and g(t) and the chosen value of $\lambda$ result in small values of C. The velocity of the particle undergoing SCODA motion must be a function of both f(t) and g(t). Further, the velocity of the particle as a result of the application of f(t) and g(t) together must not be the same as the sum of the velocities resulting from application of f(t) and g(t) independently. That is:

$$\vec{v}(f(t),g(t)) \neq \vec{v}(f(t),0) + \vec{v}(0,g(t+\lambda)) \tag{4}$$

One set of conditions which is convenient, but not necessary, for scodaphoresis is:

$$\int_{-\infty}^{\infty} f(t)dt = 0, \int_{-\infty}^{\infty} g(t)dt = 0,$$

$$\int_{-\infty}^{\infty} v(f(t),0)dt = 0, \text{ and } \int_{-\infty}^{\infty} v(0,g(t))dt = 0 \tag{5}$$

where v(f(t),0) is the velocity of a particle as a function of time when the particle is interacting only with the driving field f(t); v(0,g(t)) is the velocity of a particle as a function of time when the particle is interacting only with the mobility-varying field g(t); and, $$\int_{-\infty}^{\infty} v(f(t),g(t))dt \neq 0 \tag{6}$$

in this case, the two fields, acting independently, do not produce any net motion of the particle. However, the combined effect of the first and second fields does result in the particle being moved with a net velocity.

To optimize SCODA one can select functions f(t) and g(t) so that the first order velocity of the particles caused by either f(t) or g(t) is zero (so particles have no net drift), and so that the combination of f(t) and g(t) acts on the particles to provide a maximum velocity. One can select f(t) and g(t) and a phase shift $\lambda$ to maximize the integral:

$$\int_0^T \vec{v}(f(t),g(t+\lambda))dt \tag{7}$$

The process in this case runs from time 0 to time T or possibly for multiple periods wherein t runs from 0 to T in each period.

It is not necessary that f(t) and g(t) be represented by sinusoidal functions, by the same functions, or even by periodic functions. In some embodiments of the invention, f(t) and g(t) are different functions. In some embodiments of the invention, f(t) and g(t) are not periodic. FIGS. 1A through 1H show some examples of functions f(t) and g(t) that could be used in specific embodiments of the invention.

Figure 1B:
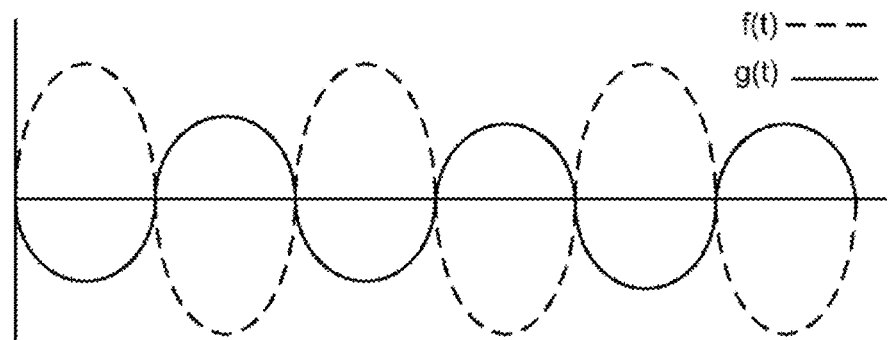
FIG. 1B shows an exemplary waveform for driving and mobility-modifying fields.

FIG. 1A shows a case wherein f(t) and g(t) are both sine functions with f(t) and g(t) in phase. FIG. 1B shows a case where f(t) and g(t) are both sine functions with f(t) and g(t) out of phase. As described below, the direction in which particles are caused to move can be reversed by altering the relative phase of f(t) and g(t).

Figure 1C:
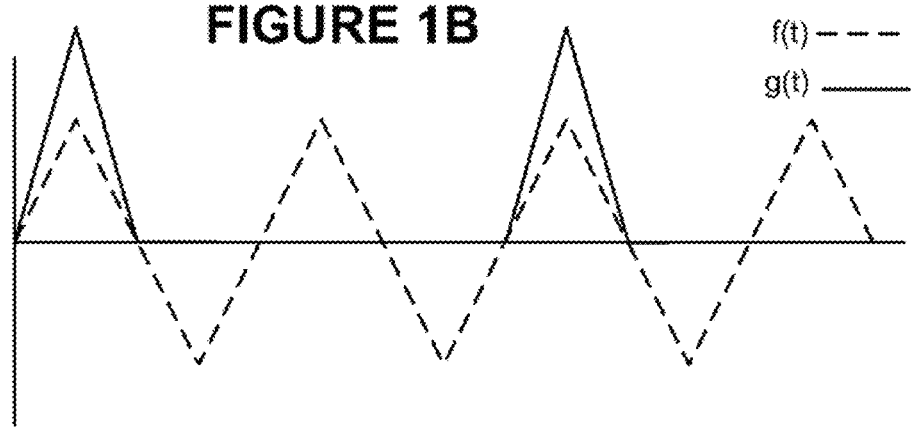
FIG. 1C shows an exemplary waveform for driving and mobility-modifying fields.
Figure 1D:
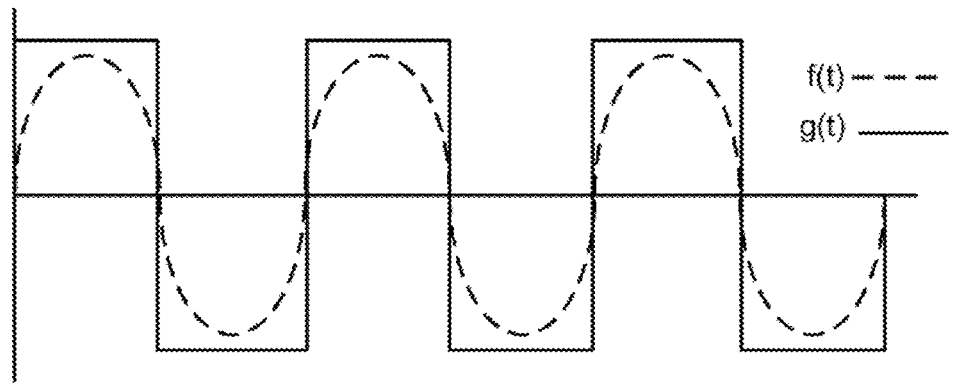
FIG. 1D shows an exemplary waveform for driving and mobility-modifying fields.
Figure 1E:
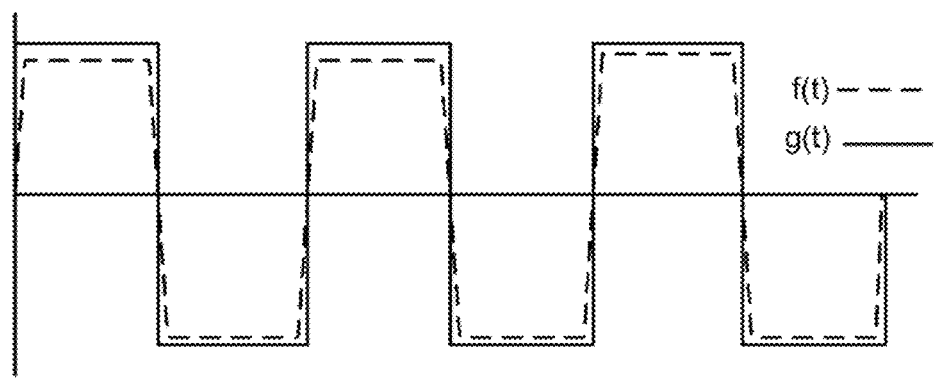
FIG. 1E shows an exemplary waveform for driving and mobility-modifying fields.
Figure 1F:
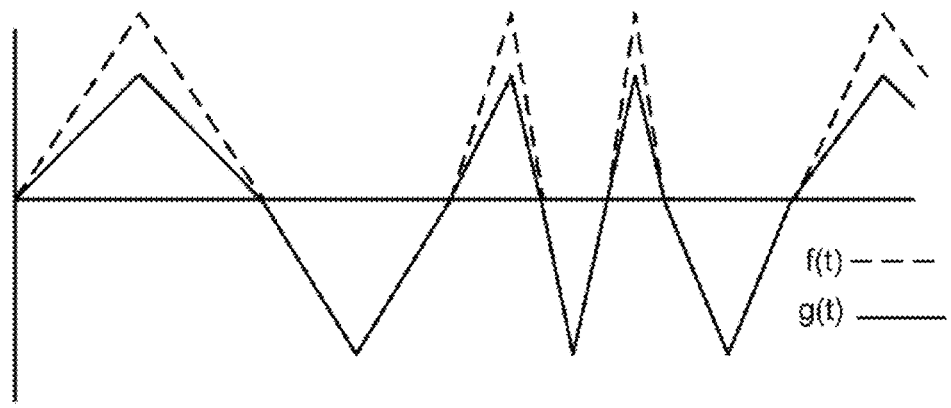
FIG. 1F shows an exemplary waveform for driving and mobility-modifying fields.
Figure 1G:
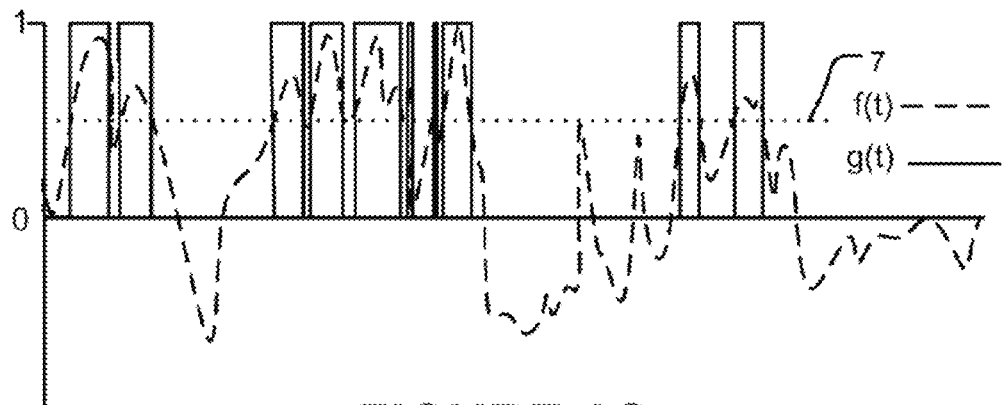
FIG. 1G shows an exemplary waveform for driving and mobility-modifying fields.
Figure 1H:
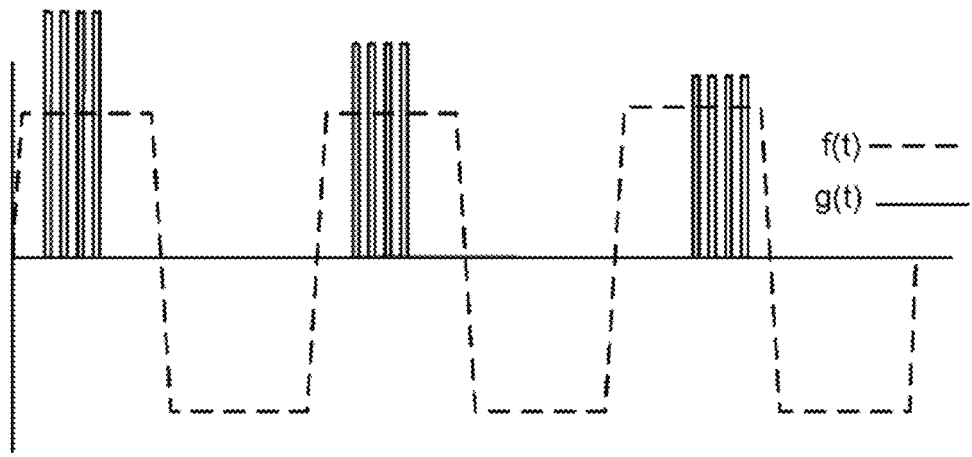
FIG. 1H shows an exemplary waveform for driving and mobility-modifying fields.

FIG. 1C shows a case where g(t) is unbalanced. In FIG. 1C, f(t) and g(t) are both triangular functions. In FIG. 1C g(t) has a frequency half of that of f(t). In FIG. 1D, f(t) has a square waveform while g(t) has a sinusoidal waveform. In FIG. 1E, f(t) and g(t) both have substantially square waveforms. In FIG. 1F, f(t) and g(t) have varying frequencies. In FIG. 1G, f(t) is essentially random noise and g(t) has a value of 1 (in arbitrary units) when f(t) exceeds a threshold 7 and has a value of 0 otherwise. In FIG. 1H, g(t) has the form of a series of short-duration impulses.

As another example, $$f(t) = \sin(\omega t), g(t) = 1 \text{ for } \frac{2n\pi}{\omega} < t < \frac{(2n+1)\pi}{\omega} \tag{8}$$

where n is any integer or set of integers (e.g. $n \in \{1, 2, 3, \ldots\}$ or $n \in \{2, 4, 6, \ldots\}$ or $n \in \{1, 4, 7, \ldots\}$. The integers n do not need to be regularly spaced apart. For example, the methods of the invention could be made to work in a case wherein the set of integers n consists of a non-periodic series. An otherwise periodic waveform f(t) or g(t) could be made aperiodic by randomly omitting troughs (or peaks) of the waveform, for example.

Figure 1I:
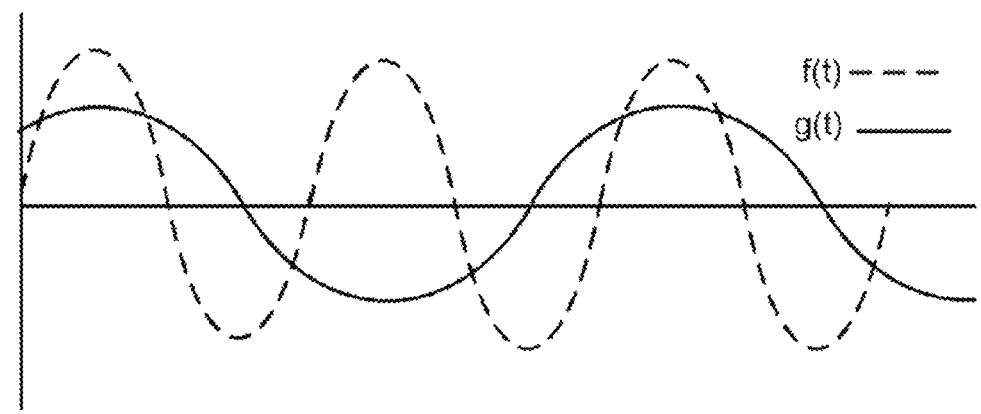
FIG. 1I shows an exemplary waveform for driving and mobility-modifying fields.

FIG. 1I illustrates a case where f(t) has a frequency twice that of g(t). The waveforms of FIG. 1I can produce SCODA motion, for example, where the mobility of particles varies in response to |g(t)|. It can be seen that |g(t)| has larger values for positive-going peaks of f(t) than for negative-going peaks of f(t).

While the waveforms shown in most of FIGS. 1A to 1I are symmetrical (i.e. they have the same overall form if inverted in spatial direction) this is not mandatory. f(t) could, in general, be asymmetrical.

Driving Fields f(t) is referred to herein as a driving function because it drives motion of the particles in the medium. In different embodiments of the invention, f(t) is produced by fields of different types. For example, f(t) may be produced by any of:

a time-varying electric field;

a time-varying magnetic field;

a time-varying flow in the medium;

a time-varying density gradient of some species in the medium;

a time-varying gravitational or acceleration field (which may be obtained, for example by accelerating a medium containing particles and periodically changing an orientation of the medium relative to the direction of the gravitational or acceleration field);

or the like.

In some embodiments, f(t) applies a force to particles that alternates in direction wherein the magnitude of the force is the same in each direction. In other embodiments, f(t) combines a component that alternates in direction and a bias component that does not alternate in direction such that the magnitude of the force applied to particles is larger in one direction than in the other. The bias component may be termed a DC component while the alternating component may be termed an AC component.

The driving field is selected to interact with the particles of interest. For example:

Where the particles are electrically charged particles (ions for example), an electric field may be used for the driving field. Electrically neutral particles may be made responsive to an electric field by binding charged particles to the electrically neutral particles. In some cases an electrically neutral particle, such as a neutral molecule, can be carried by a charged particle, such as a charged molecule. For example, neutral proteins that interact with charged micelles may be driven by an electrical driving field through the interaction with the driving field and the micelles.

Where the particles have dielectric constants different from that of the medium, an electric field having a time-varying gradient can drive motion of the particles through the medium by dielectrophoresis.

Where the particles contain magnetic material (for example, where particles of interest can be caused to bind to small beads of a type affected by magnetic forces, for example ferromagnetic beads) a magnetic field may be used for the driving field.

Where the particles have magnetic susceptibilities different from that of the medium then a gradient in a magnetic field may be used to drive motion of the particles relative to the medium by magnetophoresis.

Where the particles have densities different from that of the medium then a gravitational or other acceleration acting on the particles may drive motion of the particles relative to the medium. An AC acceleration is provided in some embodiments by exposing the medium to an acoustic field.

The driving field may directly apply a force to the particles or may indirectly cause motion of the particles. As an example of the latter, the driving field may cause living particles (mobile bacteria for example) to move in response to their own preference for certain environments. For example, some organisms will swim toward light, chemical gradients, or magnetic fields (these phenomena are known as chemotaxis, phototaxis, and magnetotaxis respectively).

Mobility-Varying Fields

The mobility of particles may by altered according to any of a wide variety of mechanisms. For example:

changing a temperature of the medium;

exposing the particles to light or other radiation having an intensity and/or polarization and/or wavelength that varies in time with the driving field;

applying an electric field to the portion of the medium through which the particles are passing;

applying a magnetic field to the medium through which the particles are passing (the magnetic field may, for example, alter an orientation of a magnetic dipole associated with the particle and thereby affect a coefficient of drag of the particle or alter a viscosity of the medium which may comprise a suitable magneto-rheological fluid);

applying an acoustic signal to the portion of the medium through which the particles are passing;

causing a cyclic change in concentration of a species in the medium;

exploiting electroosmotic effects;

causing cyclic chemical changes in the medium;

causing the particles to cyclically bind and unbind to other particles in or components of the medium;

varying a hydrostatic pressure experienced by the medium;

varying physical dimensions of the medium to cause a change in an effective drag experienced by particles in the medium;

applying magnetic fields to the medium.

Any effect that varies the mobility of a particle in response to a driving field, such as an electrophoretic driving field, can be used.

In some embodiments of the invention, the mobility of particles is varied by exploiting non-linearities in the relationship between the velocity of a particle and the intensity of the driving field. Some embodiments apply a second driving field having a component acting perpendicular to the direction of the first driving field but a frequency half that of the first driving field. Applied by itself, such a second driving field would simply cause particles to oscillate back and forth in a direction perpendicular to the direction of the main driving field. When applied together with the main driving field, however, such a second driving field can cause particles to have higher average speeds relative to the medium for one direction of the main driving field than for the other direction of the main driving field. This results in a net drift of the particles because of the non-linear relationship between particle mobility and particle speed. In some embodiments the main driving field has a symmetrical waveform, such as a sinusoidal, triangular or square waveform.

A temperature of the medium in which the particles are situated may be altered in time with the driving field. The changing temperature may result in a change in one or more of a conformation of the particles, a viscosity of the medium, a strength of interaction between the particles and the medium, some combination of these, or the like. The result is that the mobility of the particles is altered by the change in temperature. The temperature of regions in a medium may be controlled in any suitable manner including:

directing radiation at the portion of the medium to heat that portion of the medium;

energizing heaters or coolers in thermal contact with the portion of the medium;

causing endothermic or exothermic chemical reactions to occur in the portion of the medium (or in a location that is in thermal contact with the portion of the medium); and, the like.

In some embodiments of the invention the medium comprises a material that absorbs radiation and releases the absorbed radiation energy as heat. In some embodiment, localized heating of the medium in the vicinity of the particles being moved is achieved by irradiating the particles with electromagnetic radiation having a wavelength that is absorbed by the particles themselves and released as heat. In such embodiments it can be advantageous to select a wavelength for the radiation that is not absorbed or converted to heat significantly by constituents of the medium so that heating is local to the particles.

Some examples of particles that have mobilities that vary with temperature are: proteins that can be cyclically denatured or caused to fold in different ways by cyclically changing the temperature; and DNA that can be cyclically denatured.

Exposing the area of the medium in which the particles are travelling to radiation changes one or more of: a conformation of the particles, a viscosity of the medium, a strength of interaction between the particles and the medium, some combination of these, or the like. The result is that the mobility of the particles is altered by changes in the intensity and/or polarization and/or wavelength of the applied radiation. Some examples of particles that have mobilities that can be caused to change by applying light are molecules such as azobenzene or spiro-pyrans, that can be caused to undergo reversible changes in conformation by applying light. Another example of the use of light to vary the mobilities of particles in a medium is the application of light to cause partial cross-linking of polymers in a medium containing polymers.

The intensity of an electric field applied to the medium may be varied in time with the driving field. In some media the mobility of particles of certain types varies with the applied electric field. In some media the particle velocity varies non-linearly with the applied electric field.

The mobility of particles in a medium may vary with the intensity of an acoustic field applied to the medium. In some cases, an acoustic standing waves in a solution or other medium may cause transient differences in local properties of the medium (e.g. electrical resistivity) experienced by particles in the medium thus leading to local inhomogeneity in the driving field (e.g. a driving electric field).

Where mobility of particles is controlled by altering a concentration of a species, the species having the varying concentration may, for example, be a species that binds to the particles or a species that affects binding of the particles to some other species or to a surface or other adjacent structure. The species may directly affect a viscosity of the medium.

As an example of the use of electroosmotic effects to control particle mobility, consider the case where the medium in which the particles are moving is a solution containing one or more polymers. In such solutions, an applied electric field can cause bulk fluid flow. Such a flow could be controlled to provide a perturbing stimulus to a pressure or flow induced driving force, or as a perturbation to an electrical driving force, possibly exploiting non-linearities in the onset of electroosmotic flow.

Chemical changes that are exploited to control particle mobility may, for example, induce changes in one or more of:
 a conformation of the particles;
 a conformation of some other species;
 binding of the particles to one another or to other species or structures in the medium;
 binding of species in the medium to one another;
 viscosity of the medium; or
 the like.

The chemical changes may be induced optically, for example, by optically inducing cross-linking or by optically inducing oxidation or reduction of photoactive molecules such as ferrocene. The chemical changes may be induced by introducing chemical species into the medium. The chemical changes may include one or more of changes: that alter the pH of the medium; changes that result in changes in the concentration of one or more chemical species in the medium; or the like.

Particle mobility may be affected by applied magnetic fields according to any of a variety of mechanisms. For example:

The medium may contain small magnetic beads. The beads may be linked to polymers in a polymer matrix. By applying a magnetic field, the beads may be pulled away from a path of the particles, thereby reducing an effective viscosity of the medium experienced by the particles.

The medium could be a magneto-rheological fluid having a viscosity that varies with applied magnetic field.

A magnetic field may be used to cause medium viscosity to vary according to a two-dimensional pattern. The magnetic field could change in time in such a manner that the viscosity of the medium varies with position and varies in time in a manner that provides a synchronous perturbation to a periodic driving force. As another example, where the particles themselves are magnetic, transport and concentration of the particles could be affected by a magnetic field. The particles could be driven electrophoretically. The magnetic field could be switched on periodically to drive the particles toward a drag-inducing surface, or release them from such a surface. The magnetic field could also be used to make the particles aggregate.

Particles

The methods of the invention may be applied to particles of virtually any kind including molecules, ions, and larger particulates. Some non-limiting examples of particles which may be moved, concentrated and/or extracted through use of the methods of the invention are:

electrically charged or neutral biomacromolecules such as proteins, nucleic acids (single-stranded and double-stranded RNA, DNA), and suitable lipids; long polymers; polypeptides;
 aggregations of molecules such as micelles or other supramolecular assemblies;
 any particles to which magnetic beads or electrically-charged beads can be attached;
 living microorganisms; and,
 the like.

In particular the invention is effective at separating nucleic acids, which may be single-stranded or double stranded, and may vary in length from thousands of bases, to hundreds of bases, to tens of bases. The invention may also be used to separate homoduplexes of double stranded nucleic acids from heteroduplexes of nucleic acids. In one instance, the invention is used to separate or enrich so called short nucleic acids, having 500 or fewer, e.g., 200 or fewer, e.g., 100 or fewer, e.g., 50 or fewer bases. Short nucleic acids are commonly the result of cellular breakdown, and may be found, for example, in cell-free samples (e.g., blood plasma, urine), formalin-fixed samples, or forensic samples.

For any particular type of particle, one can attempt to identify a suitable driving field, medium, and mobility-altering field. Since many biomacromolecules can be electrically charged, it is often suitable to use a time-varying electrical field as the driving field when applying the invention to moving and/or concentrating such particles. Further, there are well developed techniques for causing magnetic beads to bond to specific biological materials. Where it is desired to move and/or concentrate materials which can be caused to bond to magnetic beads then magnetic fields may be used as driving fields.

Media

The medium is selected to be a medium through which the particles can move and also a medium wherein the mobility of the particles can be altered by applying a suitable mobility-altering field. The medium may comprise, for example:
 a gel, such as an agarose gel or a performance optimized polymer (POP) gel (available from Perkin Elmer Corporation);
 a solution, aqueous or otherwise;
 entangled liquid solutions of polymers;
 viscous or dense solutions;
 solutions of polymers designed to bind specifically to the molecules (or other particles) whose motion is to be directed;
 acrylamide, linear poly-acrylamide;
 micro-fabricated structures such as arrays of posts and the like, with spacing such that the particles of interest can be entangled or retarded by frequent collision or interaction with the micro-fabricated structure;
 structures designed to interact with molecules by means of entropic trapping (see, e.g. Craighead et al., in *Science* 12 May 2000 Vol. 288);
 high viscosity fluids such as PLURONIC™ F127 (available from BASF);
 water; or
 the like.

The medium is chosen to have characteristics suitable for the particles being moved. Where the particles are particles of DNA then suitable polymer gels are the media currently preferred by the inventors. In some specific embodiments of the invention the particles comprise DNA and the medium comprises an agarose gel or a suitable aqueous solution. In some embodiments the aqueous solution is a bacterial growth medium mixed with a gel such as an agarose gel.

2D Scodaphoresis

In some embodiments, the particles are constrained to move on a two-dimensional (2D) surface. In some embodiments the 2D surface is planar. The 2D surface is not necessarily planar. In some embodiments, the 2D surface comprises a relatively thin layer of a medium, such as a gel. In some embodiments the medium is free-standing. The medium may be supported on a substrate. The substrate may comprise a sheet of glass or a suitable plastic such as mylar, for example. In some embodiments the 2D layer of medium is sandwiched between the surfaces of two substrates. Where the medium has an exposed surface, the surface may be in air or another gaseous atmosphere or submerged in a liquid such as a suitable buffer, an oil, or the like. In some currently preferred embodiments, the medium comprises a layer of a gel sandwiched between two layers of thicker gel. In an example embodiment, particles move in a layer of a 1% w/v agarose gel sandwiched between two layers of 3% w/v agarose gel.

In some embodiments of the invention, a 2D surface in which particles travel may be provided by a layer within a medium which has a non-uniform viscosity or a non-uniform concentration of a species that reduces (or increases) a mobility of the particles. The viscosity or concentration gradient cause particles to remain in the relatively thin layer within the medium or on a surface of the medium.

3D Scodaphoresis

SCODA may be used to concentrate particles in three dimensions. This may be achieved in various ways. In some embodiments, 2D SCODA is performed in a plane. The 2D SCODA may be performed using the electrophoretic SCODA method described below, for example, Z electrodes placed above and below the plane could apply an electric field that tends to drive any particles that begin to move out of the plane back into the plane.

3D SCODA could also be performed by providing a 6 electrode arrangement, where each electrode is placed on the surface of a body of a medium such as a gel. Defining XY and Z axes of such a cube, 2D SCODA would then be run on the 4 electrodes in the XY plane, then the 4 electrodes in the YZ plane, then the 4 electrodes in the XZ plane, then repeating in the XY plane and so forth. This would produce a net 3D focusing effect, with a net SCODA force that is radial in three dimensions, but about ⅓ as strong as the 2D SCODA force for the same electrode voltages.

Samples

A variety of fluidic samples can be enriched using methods of the invention. Additionally, solid samples may be solubilized or suspended and then enriched. Suitable biological samples may include, but are not limited to, cultures, blood, plasma, serum, saliva, cerebral spinal fluid, pleural fluid, milk, lymph, sputum, semen, urine, stool, tears, saliva, sweat, needle aspirates, external sections of the skin, respiratory, intestinal, and genitourinary tracts, tumors, organs, cell cultures or cell culture constituents, or tissue sections. In some embodiments, the biological sample may be analyzed as is, that is, without additional preparation. In an alternate embodiment, harvest and/or isolation of materials of interest may be performed prior to analysis.

A sample may include any of the aforementioned samples regardless of their physical condition, such as, but not limited to, being frozen or stained or otherwise treated. In some embodiments, a biological sample may include compounds which are not naturally intermixed with the sample such as preservatives, anticoagulants, buffers, fixatives, nutrients, antibiotics, or the like.

In some embodiments, a biological sample may include a tissue sample, a whole cell, a cell constituent, a cytospin, or a cell smear. A tissue sample may include a collection of similar cells obtained from a tissue of a biological subject that may have a similar function. In some embodiments, a tissue sample may include a collection of similar cells obtained from a tissue of a human. Suitable examples of human tissues include, but are not limited to, (1) epithelium; (2) the connective tissues, including blood vessels, bone and cartilage; (3) muscle tissue; and (4) nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines. In some embodiments, a biological sample includes tissue sections from healthy or diseased tissue samples (e.g., tissue section from colon, breast tissue, prostate, lung, etc.). A tissue section may include a single part or piece of a tissue sample, for example, a thin slice of tissue or cells cut from a tissue sample.

In some embodiments, a biological sample may be recovered from a solid support and suspended or solubilized prior to being used with methods of the invention. A solid support may include microarrays (e.g., DNA or RNA microarrays), gels, blots, glass slides, beads, swabs or ELISA plates. In some embodiments, a biological sample may be adhered to a membrane selected from nylon, nitrocellulose, and polyvinylidene difluoride. In some embodiments, the solid support may include a plastic surface selected from polystyrene, polycarbonate, and polypropylene. In some embodiments the biological sample is recovered from a formalin-fixed sample, e.g., a formalin-fixed paraffin-embedded (FFPE) sample.

A biological sample may be of prokaryotic origin or eukaryotic origin (e.g., insects, protozoa, birds, fish, reptiles). In some embodiments, the biological sample is mammalian (e.g., rat, mouse, cow, horse, pig, dog, cat, donkey, guinea pig, or rabbit). In certain embodiments, the biological sample is of primate origin (e.g., example, chimpanzee, or human). The samples may be forensic samples including, but not limited to, blood samples, saliva samples, urine samples, feces samples, microbial samples, pathogen samples, forensic biological samples, crime scene biological samples, drug/alcohol samples, chemicals (e.g., explosives), and residues.

Additional Analysis of Particles

In some instances, enriched samples produced with the methods and apparatus of the invention will be additionally analyzed or processed. For example, the resultant enriched sample may be amplified, hybridized, stored, lyophilized, or sequenced.

Where the enriched sample contains nucleic acids, the sample may be amplified using Polymerase Chain Reaction (PCR) technologies. A typical PCR reaction includes multiple amplification steps, or cycles that selectively amplify a targeted nucleic acid species. Additional references describe the PCR process, and common variations thereof, such as quantitative PCR (QPCR), real-time QPCR, reverse transcription PCR (RT-PCR) and quantitative reverse transcription PCR (QRT-PCR). PCR instruments and reagents are commercially available from suppliers such as Roche Molecular Diagnostics (Pleasanton, Calif.).

A typical PCR reaction includes three steps: a denaturing step in which a targeted nucleic acid is denatured; an annealing step in which a set of PCR primers (forward and backward primers) anneal to complementary DNA strands; and an elongation step in which a thermostable DNA polymerase elongates the primers. By repeating this step multiple times, a DNA fragment is amplified to produce an amplicon, corresponding to the targeted DNA sequence. Typical PCR reactions include 30 or more cycles of denaturation, annealing and elongation. In many cases, the annealing and elongation steps can be performed concurrently, in which case the cycle contains only two steps. Using PCR amplification, it is possible to amplify the targeted nucleic acid exponentially.

However, as discussed in the background of this application, PCR amplification introduces errors into the amplified nucleic acid products. In some instances, the error rate is of the same magnitude as the incidence of target nucleic acids in the sample. In these instances if PCR amplification is used, it is done after enrichment to avoid creating erroneous target nucleic acids. In some embodiments, where the PCR error rate is acceptable compared to the incidence of target nucleic acids in the sample, it is beneficial to do some PCR on the sample prior to enrichment, to boost the total number of target nucleic acids in the sample. In practice, PCR prior to enrichment is limited to fewer than 20 cycles, e.g., 15 or fewer cycles, e.g., 10 or fewer cycles, e.g., 5 or fewer cycles, in order to limit the introduction of errors. After enrichment, the enriched target nucleic acids may be amplified for further processing with 20 or more, e.g., 25 or more, e.g., 30 or more, e.g., 40 or more PCR cycles.

Several methods are available to identify target nucleic acids (e.g., variant nucleic acids, e.g., mutations) that have been enriched using methods and apparatus of the invention. In some instances an enriched sample may be analyzed with a hybridization probe. Typically, a labeled single stranded polynucleotide, which is complementary to all or part of the targeted sequence, is exposed to the sample, a wash step is performed, and then the sample is observed for the presence of the label. In some instances, amplification and hybrid probe analysis may be performed simultaneously, e.g., using quantitative PCR.

In other instances the complementary polynucleotide probes may be immobilized on a solid support. In this instance, hybrid probe analysis typically includes (1) labeling nucleic acids in the enriched sample, (2) pre-hybridization treatment to increase accessibility of support-bound probes and to reduce nonspecific binding; (3) hybridization of the labeled nucleic acids to the surface-bound polynucleotides, typically under high stringency conditions; (4) post-hybridization washes to remove nucleic acid fragments not bound to the solid support polynucleotides; and (5) detection of the hybridized, labeled nucleic acids. Detection may be done, for example by fluorescence detection, however other methods may be used, depending upon the nature of the label.

In some embodiments, an enriched sample containing multiple target nucleic acids may be identified with a multiplex protocol designed to identify multiple specific mutations of interest. For example, single nucleotide polymorphisms (SNPs) among the target nucleic acids may be determined with a single base extension kit, such as SNAPSHOT™ available from Applied Biosystems (Life Technologies, Carlsbad, Calif.). Using this kit, the enriched sample will be mixed with a set of primers of varying length and sequence, each primer being complementary to different loci on the target nucleic acids. Upon mixing, the primers will hybridize with a specific target nucleic acid, forming a duplex with a 3' terminus adjacent to the SNP. In the presence of a polymerase, a single fluorescently-labeled base is added to the duplex and the resulting populations of fluorescently-labeled moieties can be characterized by length and label color (e.g., using Sanger sequencings, for example GENESCAN™ analysis, Applied Biosystems) to determine the presence and amount of the mutations.

Another method that can be used to identify nucleic acids in the enriched sample is genetic sequencing. Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454™ sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD™ sequencing.

In preferred embodiments, nucleic acids enriched with methods of the invention may be sequenced using next-generation sequencing. For example, 454™ sequencing, available from Roche (Branford, Conn.), may be used to quickly and accurately sequence enriched nucleic acid samples. (See Margulies, M et al. 2005, Nature, 437, 376-380, incorporated herein by reference in its entirety.) 454™ sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments are then attached to DNA capture beads, e.g., streptavidin-coated beads using, e.g., Adaptor B, which contains 5'-biotin tag. The fragments attached to the beads are PCR amplified within droplets of an oil-water emulsion to make multiple copies of DNA fragments on each bead. In the second step, the beads are captured in picoliter wells. Finally, pyrosequencing is performed on each DNA fragment in parallel. As nucleotides are added, a light signal is generated and recorded by a CCD camera in the instrument. The signal strength is proportional to the number of nucleotides incorporated. The signals are then analyzed and correlated to determine the sequence.

Alternatively, ION TORRENT™ sequencing systems, available from Life Technologies (Carlsbad, Calif.) may be used to directly obtain the sequences of the enriched nucleic acids. Among other references, the methods and devices of ION TORRENT™ sequencing are disclosed in U.S. patent application numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the content of each of which is incorporated by reference herein in its entirety. In ION TORRENT™ sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments are then attached to a surface at a concentration such that the fragments are individually resolvable. Addition of one or more nucleotides releases a proton ($H^+$), which is detected and recorded in a sequencing instrument. The signal strength is proportional to the number of nucleotides incorporated. The signals are then analyzed and correlated to determine the sequence.

Another example of a next-generation sequencing technology that can be used to sequence enriched nucleic acids is ILLUMINA™ sequencing, available from Illumina, Inc, (San Diego, Calif.). ILLUMINA™ sequencing amplifies DNA on a solid surface using fold-back PCR and anchored primers. The DNA is then fragmented, and adapters are added to the 5' and 3' ends of the fragments. Next, fragments are attached to the surface of flow cell channels, and the DNA is extended and bridge amplified. This process results in several million clusters of approximately 1,000 copies of single-stranded DNA molecules of the same template in each channel of the flow cell. Using primers, DNA polymerase, and four fluorophore-labeled, reversibly-terminating nucleotides, the copies are then sequentially sequenced and fluorescence-imaged to determine the added nucleotide. The 3' terminators and fluorophores from each incorporated base are subsequently removed, and the incorporation, detection and identification steps are repeated to read out the next nucleotide.

In some instances, the enriched nucleic acids will be identified using mass spectrometry. Mass spectrometry uses a combination of electric and/or magnetic fields to cause nucleic acid ions (or pieces of) to follow specific trajectories (or to have specific flight times) depending on their individual mass (m) and charge (z). In addition, by arranging collisions of a parent molecular ion with other particles (e.g. argon atoms), the molecular ion may be fragmented forming secondary ions by the so-called collision induced dissociation (CID). The fragmentation pattern/pathway very often allows the derivation of detailed structural information. The structural information may be used to determine the sequence of the nucleic acid. Nucleic acids are difficult to volatilize, however. Using techniques such as electrospray/ionspray (ES) and matrix-assisted laser desorption/ionization (MALDI), nucleic acids can be volatilized, ionized, and characterized by their mass-to-charge profile. Additionally, DNA massarrays, such as offered by Sequenom (San Diego, Calif.), can be used to facilitate MALDI mass spectrometric analysis by tagging complementary nucleic acids with easily-detected mass labels.

Control Systems

Any suitable control mechanism may be used to cause a driving field and a mobility-varying field to be applied in a coordinated manner to cause particles to move by SCODA. In some embodiments of the invention, the time-variation of the driving field and the mobility-varying field are derived directly from a common source such that their effects on the particles are correlated. In other embodiments of the invention the driving and mobility-varying fields are generated under the control of a controller such as a hard-wired controller, a programmable controller, a general purpose computer equipped with suitable interface electronics or the like. Any suitable control mechanism including those known to those skilled in the art of designing scientific equipment may be applied.

Electrophoretic Concentration of Particles by SCODA

Consider an electrically charged particle that has an electrophoretic mobility, $\mu$ in an electric field given by $\vec{E}=\cos(\omega t) E\hat{E}$ where $\hat{E}$ is a unit vector. By definition, the particle will move with a velocity given by:

$$\vec{v} = \mu \cos(\omega t) E_0 \vec{E} \quad (9)$$

From Equation (9), $\vec{v}$ has a time average of zero. If $\mu$ varies as a function of time and the Fourier transform of $\mu$ has a component proportional to $\cos(\omega t)$ then the time average of v(t) may not be zero. As a simple example, consider the case where:

$$\mu(t) = \mu_0 + \mu_1 \cos(\omega t) \quad (10)$$

In this case, the time average of v(t) is:

$$\vec{v} = \tfrac{1}{2} \mu_1 E_0 \hat{E} \quad (11)$$

This demonstrates the basic principle that there can be a non-zero electrophoretic drift even if the time average of the applied electric field is zero.

Now consider the case where the mobility of a particle is a function of electric field strength. While virtually any nonlinearity can be employed, consider the case where a particle's velocity is parallel to the direction of a driving electric field and the particle's speed is given by:

$$v = kE^2 \quad (12)$$

where k is a constant and E is the magnitude of the electric field. In this case, the particle's speed is proportional to the square of the magnitude of the electric field. The effective mobility of the particle (i.e. the relationship between small changes in drift velocity, $d\vec{v}$, and small changes in the electric field, $d\vec{E}$) varies with the magnitude of the applied electric field.

In Cartesian coordinates:

$$dv_x = \frac{\partial v_x}{\partial E_x} dE_x + \frac{\partial v_x}{\partial E_y} dE_y \text{ and} \quad (13)$$

$$dv_y = \frac{\partial v_y}{\partial E_x} dE_x + \frac{\partial v_y}{\partial E_y} dE_y$$

Where the particle speed varies with the electric field as in Equation (12), Equation (13) reduces to:

$$dv_x = k\left[\left(E + \frac{E_x^2}{E}\right) dE_x + \left(\frac{E_x E_y}{E}\right) dE_y\right], \quad (14)$$

and $$dv_y = k\left[\left(\frac{E_x E_y}{E}\right) dE_x + \left(E + \frac{E_y^2}{E}\right) dE_y\right] \quad (15)$$

To help interpret this, consider the case where $E_y = 0$ such that $E_x = E$. In this case Equations (14) and (15) become:

$$dv_x = 2kE\, dE_x \text{ and } dv_y = kE\, dE_y \quad (16)$$

From Equation (16) one can see that the influence on the particle velocity of perturbations of the electric field has a magnitude proportional to that of the ambient field. A perturbation having the same direction as the electric field has twice the influence on the particle velocity as a perturbation perpendicular to the electric field.

This can be exploited to provide an applied electric field that causes particles to be concentrated. Consider a plane wherein an applied electric field has a constant magnitude, E, and the electric field rotates in direction at an angular frequency $\omega$ so that the components of the electric field in x and y directions are given by:

$$E_x = E \cos(\omega t) \text{ and } E_y = \sin(\omega t) \quad (17)$$

Substituting the values from Equation (17) into Equations (14) and (15) yields a result which is the sum of constant terms, sine and cosine terms having an angular frequency $\omega$, and sine and cosine terms having an angular frequency $2\omega$. A frame of reference can be selected such that only the cosine terms having an angular frequency of $2\omega$ contribute to net particle drift. Evaluating only these terms yields:

$$dv_x = \frac{kE}{2}[\cos(2\omega t)]dE_x, \quad (18)$$

$$dv_y = \frac{kE}{2}[\cos(2\omega t)]dE_y$$

If a perturbing electric field having the form of a quadrupole field that varies with a frequency 2ω is added to the basic electric field specified by Equation (17) then a net drift of particles can be caused. For a perturbing electric field given by:

$$dE_x = -dE_q x \cos(2\omega t) \text{ and } dE_y = dE_q y \cos(2\omega t) \quad (19)$$

it can be shown that:

$$\overline{dv} = \frac{kEdE_q}{4}\vec{r} \quad (20)$$

Equation (20) shows that for charged particles at all positions $\vec{r}$ there is a time-averaged drift toward the origin with a speed proportional to k, the coefficient that specifies the field-dependence of the mobility, E, the strength of the rotating field, and dEq, the strength of the perturbing quadrupole field.

Figure 2:
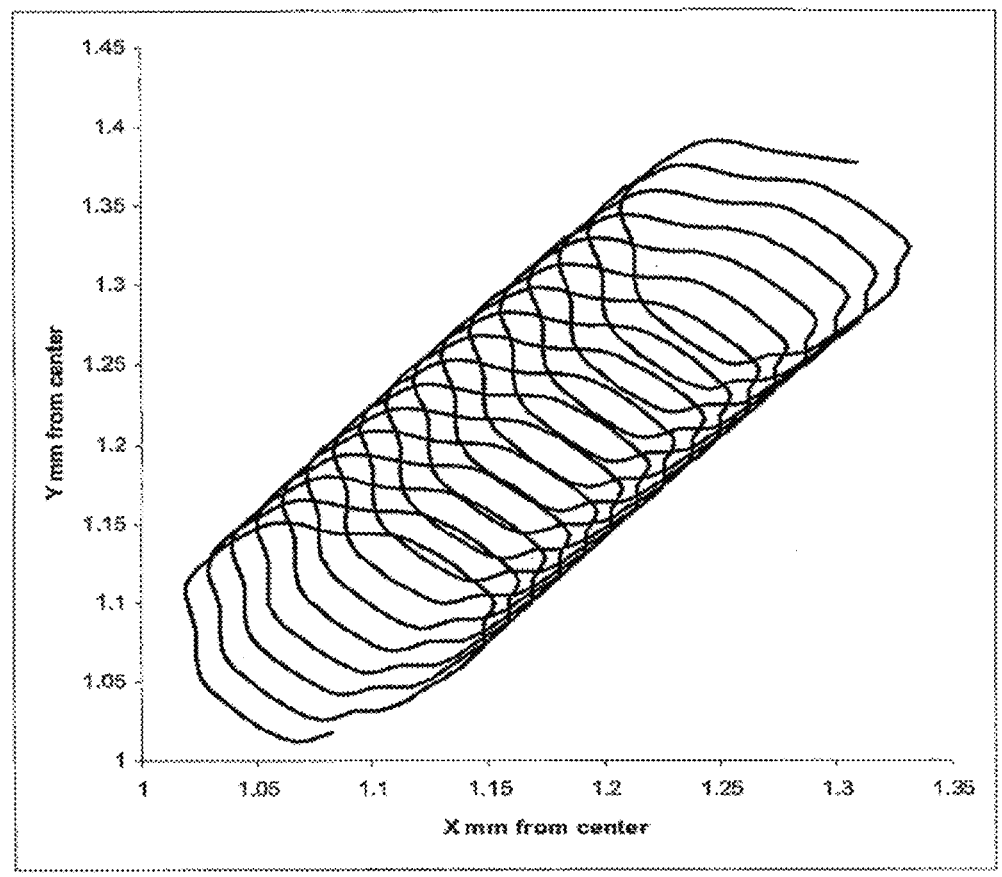
FIG. 2 is a plot showing a numerical simulation of the path of a particle exposed to a time-varying driving field and a time-varying mobility varying field.

The above calculation is for a case where the perturbing quadrupole field has a magnitude that is small in comparison to the rotating field. This is not necessary in general. FIG. 2 shows the result of a numerical simulation of the path of a particle in a case where the rotating electric field and quadrupole electric field are similar in magnitude. Motion begins at the top right hand side of FIG. 2 and progresses toward the bottom left over a period of 200 seconds. The applied electric fields are as described in Table I below. Each loop in the spiral path corresponds to a cycle of 12 voltage patterns each applied for 1 second. The uniform field amplitude is 3845 V/m at the origin (center of the electrode pattern). At the same location, the magnitude of the quadrupole component of the electric field is 4.2×105 V/m² or about 4200 V/m at a location 1 mm from the origin.

In many situations it is advantageous to concentrate particles in regions that are free of electrodes. Electrochemical processes at electrodes can cause damage to DNA and other sensitive materials. An electrical field that provides a particle focusing effect, as described above, can be provided without the need for electrodes at the location in which the particles become concentrated.

One can estimate the size of the spot into which particles can be concentrated from the Einstein-Smoluchowsky equation for diffusion with drift. A characteristic length scale, R, for the radius of a concentrated spot is given by:

$$R \propto \sqrt{\frac{D}{\mu_s}} \quad (21)$$

where D is the diffusion coefficient for the particles and $\mu_s$ is given by $kEE_q/4$.

Figure 3A:
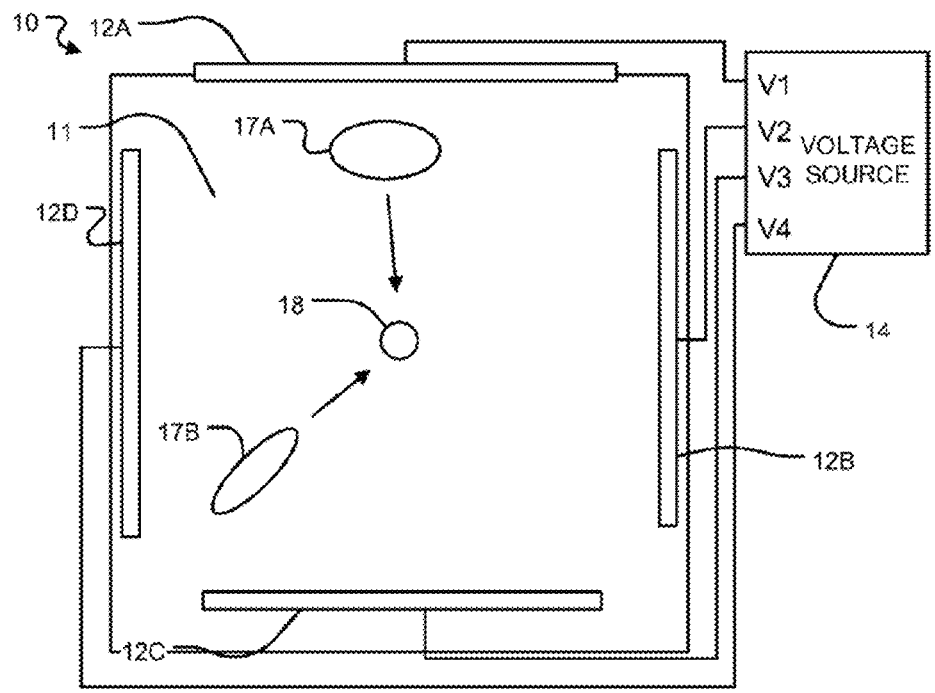
FIG. 3A is a schematic diagram of an apparatus that may be used to practice embodiments of the invention.

FIG. 3A shows apparatus 10 having a simple arrangement that can be used to practice the invention. A layer 11 of a medium, which may be a gel, such as an agarose gel, is located between four symmetrically arranged electrodes 12A, 12B, 12C, and 12D (collectively electrodes 12). It has been found to be desirable to provide electrodes 12 in the form of mesh electrodes. A power supply 14 applies individually controllable electrical potentials V1, V2, V3, and V4 to electrodes 12A through 12D respectively. Since it is the relative potentials of electrodes 12A through 12D that is significant, any one of electrodes 12A to 12D may be held at a convenient fixed voltage, such as 0 volts, while the voltages applied to the other electrodes are varied, if desired.

Figure 3B:
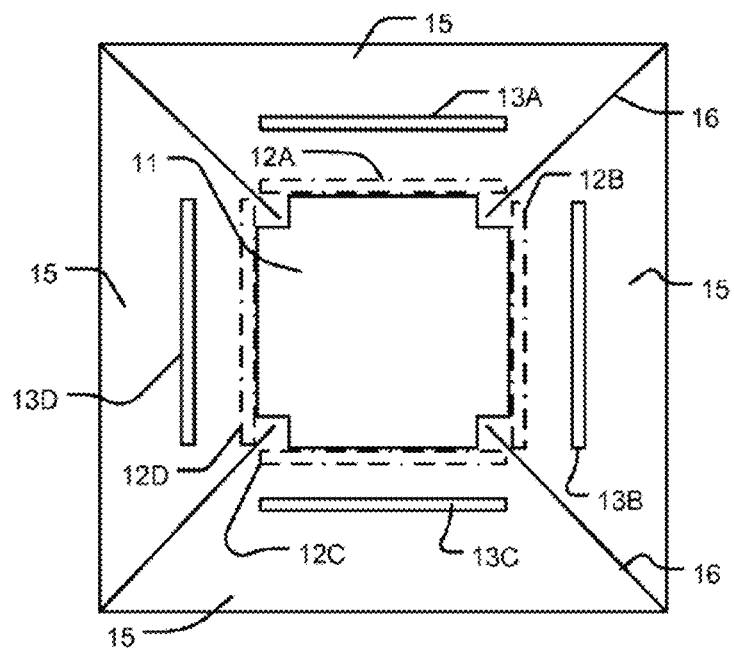
FIG. 3B is a schematic diagram of an apparatus that may be used to practice embodiments of the invention.

It is generally desirable to control the potentials applied to the electrodes to help stabilize the electric stimuli against small fluctuations due to changing temperature or changing power supply characteristics. Separate electrical potential sensing electrodes may be incorporated to provide feedback to a controller representing the actual electrical potential being applied. FIG. 3B is a schematic view of an apparatus comprising mesh electrodes 12A, 12B, 12C, and 12D and separate potential sensing electrodes 13A, 13B, 13C, and 13D (collectively electrodes 13). Large buffer reservoirs 15 maintain an ample supply of buffer against evaporation for long runs. Insulating barriers 16 separate adjacent reservoirs 15 electrically. Electrodes 13 are located in buffer reservoirs 15 and monitor the potential in the buffer. Feedback from electrodes 13 allows a suitably configured controller 14 to automatically adjust the voltages on mesh electrodes 12 to compensate for varying voltage drops across the mesh electrodes/buffer interface.

The magnitude of the applied voltage is chosen to match the size of the apparatus and the particles being separated. For DNA separations in agarose gels electric driving fields of approximately 50V/cm have been found to give satisfactory performance. The current supplied will depend upon the electrical conductivity and dimensions of the medium.

The application of the potentials causes electrically charged particles in medium 11 to move toward a central region 18. FIG. 3A shows groups 17A and 17B of particles moving toward concentration region 18. As noted above, the precise waveform according to which the applied electric fields vary is not critical to the operation of the invention. In a prototype embodiment of the invention, the potential variation of Equations (16) and (18) was approximated by a series of patterns of discrete voltages applied to electrodes 12A through 12D. In the prototype, each cycle was made up of 12 patterns that were each applied for 1 second before moving to the next pattern. Table 1 shows the voltages applied for each pattern.

TABLE 1

Applied voltages for scodaphoresis apparatus of FIG. 3A.
Voltage Patterns

| Pattern | Electrode 12A (V) | Electrode 12B (V) | Electrode 12C (V) | Electrode 12D (V) |
|---|---|---|---|---|
| 1 | 0 | −66 | 0 | −198 |
| 2 | 132 | 132 | 0 | 0 |
| 3 | 132 | 198 | 0 | 198 |
| 4 | 132 | 198 | 0 | 198 |
| 5 | 132 | 0 | 0 | 132 |
| 6 | 0 | −198 | 0 | −66 |
| 7 | 0 | −198 | 0 | −66 |
| 8 | −132 | −132 | 0 | 0 |
| 9 | −132 | 66 | 0 | 66 |
| 10 | −132 | 66 | 0 | 66 |
| 11 | −132 | 0 | 0 | −132 |
| 12 | 0 | −66 | 0 | −198 |

Figure 3C:
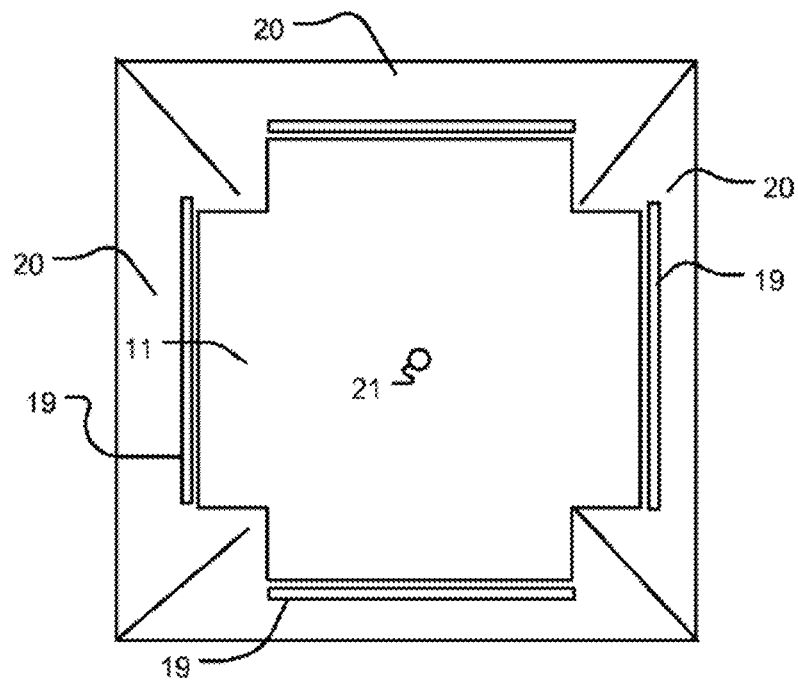
FIG. 3C is a schematic diagram of an apparatus that may be used to practice embodiments of the invention.

In the prototype embodiment of the invention illustrated schematically in FIG. 3C, medium 11 was in the form of a gel slab made up of 8-11 ml of 0.25% agarose gel (Agarose 2125 OmniPur available from EMD Chemicals of Gibbstown N.J., USA) forming a 3.8 cm square on an acrylic base in a 0.1× Tris-acetate-EDTA buffer. Four electrodes were submerged in the gel. Each electrode extended across one third of one side of the gel boat approximately 2.5 mm up from the bottom of the gel boat. DNA was prepared by mixing 8 µl of 500 µg/ml λ phage DNA (48,502 bp, part No. N3011L available from New England Biolabs of Beverly Mass., USA) with 12 µl 0.1×TAE. 5 µl spots of the DNA were pipetted directly onto the gel after the gel had set. A thin covering of TAE was placed on the gel. The voltage patterns of Table 1 were applied to the electrodes. It was found that the DNA spots were all carried to a central area of the gel.

For the DNA used in the prototype, D was measured experimentally to be $2 \times 10^{-12}$ m$^2$/s. $\mu_s$ was measured to have a value of approximately $1 \times 10^{-3}$ 1/s. Using these values, the limiting spot size was calculated to be on the order of 100 µm. Spot radii on the order of 150 to 250 µm have been achieved in experiments.

In another experiment, a homogeneous solution of 400 ng/ml λ DNA in 1% agarose gel (0.01×TAE) was subjected to scodaphoresis. The gel was prepared by mixing 3 ml of 1% agarose gel with 1.5 µl of 500 ng/µl 48,502 bp λ DNA and 1.5 µg ethidium bromide (500 ng/ml final concentration). The gel was allowed to cool to approximately 65° C. and then poured into the gel boat. The gel was arranged in a cross shape, as shown in FIG. 3C. Platinum electrodes 19 0.03 mm in diameter were located in open electrode regions 20 of the apparatus. The electrode regions were free from gel and filled with 0.01×TAE buffer.

The distance between opposing electrodes was approximately 2.4 cm. After approximately 90 minutes, the λ DNA was found to have been concentrated in a region 21 in the center of the gel boat in a spot having a full width at half maximum of about 300 µm. The concentration of the λ DNA in the spot was enhanced by a factor of approximately 3000 to 4000 as compared to the initial concentration of λ DNA in the gel boat. The ability to cause DNA to be concentrated in an area 21 which is away from electrodes is advantageous in various applications.

The concentration factor, F, that can be achieved using a square gel slab having sides of length L is calculated to be approximately:

$$F = \frac{1}{\pi}\left(\frac{L}{200}\ \mu m\right)^2 \qquad (22)$$

Therefore, other factors being equal, increasing the dimensions of the gel slab can increase the concentration factor. For example, calculations suggest that a 35 cm×35 cm square gel slab could produce a concentration factor on the order of $10^6$. To achieve the best concentration it may be desirable to take steps to inhibit diffusion of particles out of the 2D surface in which SCODA is being used to concentrate the particles.

Electrophoretic SCODA in two dimensions can be performed conveniently using four electrodes arranged in two opposing pairs, as described above. Other arrangements of three or more electrodes that are not collinear with one another could also be used. For example SCODA could be performed using three electrodes arranged at corners of a triangle. SCODA could also be performed using five or more electrodes arranged around a region of a medium.

Since the passage of electrical current through a medium can lead to heating of the medium and most practical media are electrically conducting to some degree it is desirable to design SCODA apparatus to minimize heating, where practical, and to ameliorate the effects of heating, where necessary. For example, SCODA may be practiced in ways which include one or more of:

cooling the medium through the use of a cooler in physical contact with the medium, cooling a buffer circulating around the medium, blowing cool air over the medium or evaporatively cooling the medium;

making the medium very thin, thereby reducing the electrical current flowing in the medium and improving dissipation of heat from the medium;

placing the medium on a thermally-conductive substrate that acts as a heat sink;

reducing the electrical conductivity of the medium by way of a chemical treatment or by separating from the medium unneeded species that give rise to increased electrical conductivity;

providing a reservoir of buffer and replenishing buffer surrounding the medium as the buffer evaporates (see, for example, FIG. 3B);

providing one or more temperature sensors that monitor temperature of the medium and controlling the temperature of the medium to remain within an acceptable range by controlling the electrical current supplied to electrodes; and, using a driving field other than an electrical field.

3D SCODA

Figure 3D:
FIG. 3D is a schematic diagram of an apparatus that may be used to practice embodiments of the invention.

FIG. 3D shows apparatus similar to that of FIG. 3A that has been modified by the provision of additional Z electrodes 22A and 22B. Z electrodes 22A and 22B are each maintained at a DC voltage. For negatively charged particles, Z electrodes 22A and 22B are kept more negative in potential than the 2D SCODA electrodes 12A, 12B, 12C, and 12D. The provision of the Z electrodes provides a focusing force in the Z axis, and a de-focusing force in the XY plane of medium 11. The defocusing force is counteracted by SCODA.

Figure 3E:
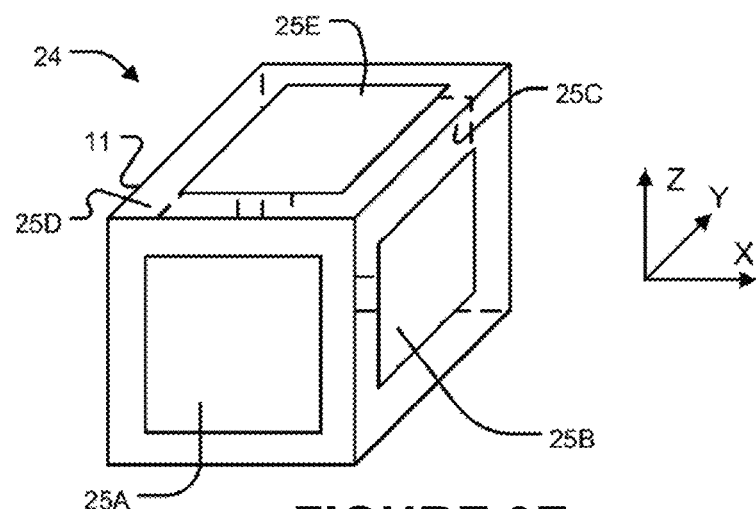
FIG. 3E is a schematic diagram of an apparatus that may be used to practice embodiments of the invention.

FIG. 3E shows apparatus 24 according to an embodiment of the invention that provides 3D concentration of particles in a cube-shaped block of medium 11 by alternately performing SCODA using electrodes in XY, XZ, and YZ planes. For example, electrodes 25A, 25B, 25C, and 25D are used for concentration in the XY plane. Electrodes 25A, 25E, 25C and another electrode (not visible in FIG. 3E) on the side of medium 11 opposed to electrode 25E are used for concentration in the YZ plane. Electrodes 25B, 25E, 25D and the electrode opposed to electrode 25E are used for concentration in the XZ plane.

Size Selection

If desired, SCODA processes can be made to select DNA and similar particles by size. This may be achieved by suitably adjusting the diffusion coefficient, D (D can be controlled by choice of medium), and the frequency of the driving field. Using higher driving field frequencies can cause larger particles to be less likely to be concentrated by SCODA. For example, in one experiment applying a driving field having a period of 12 seconds was found to concentrate both long λ DNA and shorter DNA fragments from a 1 kB ladder. It was found that reducing the period of the driving field to approximately 10 ms resulted in concentration of only the shorter DNA fragments but not the longer λ DNA fragments. While the inventors do not wish to be bound by any particular theory of operation, this size selection may be due to the 10 ms period being shorter than the relaxation time for the larger λ DNA fragments and longer than the relaxation time for the shorter DNA fragments.

In the same experiment it was found that SCODA (under these conditions) did not concentrate shorter DNA fragments (smaller than a few hundred bp). The selection out of the small sizes may be due to the smaller fragments having higher values for the diffusion coefficient D.

It is believed that SCODA provides a method for separating supercoiled plasmids from plasmids that are nicked or otherwise degraded.

Purification of DNA

Because SCODA can be made selective for different kinds of particles by choosing a suitable medium and/or combination of driving and mobility-varying fields, SCODA can be used to purify materials, such as DNA. SCODA can be applied to cause DNA (or optionally DNA having a particular size range) to concentrate at a spot or along a line while other materials are not concentrated at the spot or line.

For example, in initial experiments, λ DNA was concentrated from a mixture of λ DNA and bovine serum albumin (BSA). There was a 10:1 concentration ratio of BSA to λ DNA. The λ DNA was concentrated into a spot, as described above. The BSA was not concentrated in the spot.

In some embodiments of the invention, denaturing agents, protease, nuclease inhibitors and/or RNAase are added to a mixture of materials from which the particles are to be separated. Such agents may be provided to facilitate one or more of: reducing the binding of undesired molecules to fragments of DNA or other molecules that are desired to be concentrated; reducing the amount of RNA present, if so desired; preventing damage to DNA; and/or breaking down the undesired molecules into components that will not be concentrated by SCODA.

In some cases it may be desirable to use SCODA to separate particles of interest from a mixture which includes materials, such as salts, that cause the medium a high electrical conductivity. For example, bacterial cell cultures are often grown in media having salt contents on the order of up to 0.4M. In cases where it is desired to use electrophoretic SCODA to separate DNA directly from a cell culture, such as an $E.\ coli$ culture, the high electrical conductivity will result in higher electrical currents in the medium. This in turn can lead to heating of the medium. This issue may be addressed by one or some combination of the heating control techniques discussed above.

SCODA with Selective Media

The mobility of a particle in a medium may be made dependent upon the presence in the particle of a specific DNA sequence by providing a medium with which DNA interacts by binding interactions. For example, a gel may be made to include DNA oligonucleotides that are complementary to the DNA in the particles that it is desired to concentrate. The complementary DNA oligonucleotides may be covalently bonded to the gel.

If the characteristic time required for the particles to bind to the complementary DNA oligonucleotides is $t_{on}$ and the characteristic time required for the particles to dissociate from the DNA oligonucleotides is $t_{off}$ then the average drift velocity for a particle in the medium is given by:

$$\bar{v} = \mu(E) * E \frac{t_{on}}{t_{on} + t_{off}} \quad (23)$$

where $\mu(E)$ is the field-dependent particle mobility due to reptation effects. Typically, $t_{off}$ is determined by an Arrhenius relationship while $t_{on}$ is determined by diffusive effects. By selecting particles to have lengths of 1000 or more nucleotides, reasonable values for $t_{off}$ of 1 second or less can be achieved with practical values of electric field (for example, electric fields in the range of 100 to 200 V/cm).

Electric Driving Field Combined with Thermal Mobility Varying Field

A demonstration of SCODA was carried out by thermally altering the drag coefficient of current-carrying solute ions in an electrolyte. When applying an AC potential across an electrolyte solution, and synchronously raising and lowering the temperature of the solution, a net transport of ions is expected. If the oscillation frequency of the AC potential differs from the frequency of the thermal oscillations, a detectable component of the ionic current should be present at the difference of the two frequencies, indicating alternating (AC) transport due to SCODA.

Separation of Differentially Modified Molecules

In some embodiments, molecules that are identical except for the presence or absence of a chemical modification that alters the binding of the molecule for a probe are separated using SCODA. Some embodiments of SCODA are sufficiently sensitive to separate two molecules that have only a small difference in binding for the immobilized agent. Examples of such molecules include differentially modified molecules, such as methylated and unmethylated nucleic acids, methylated or acetylated proteins, or the like.

For example, it has been previously shown that methylation of cytosine residues increases the binding energy of hybridization relative to unmethylated DNA sequences. RNA sequences would be expected to display a similar increase in the binding energy of hybridization when methylated as compared to unmethylated sequences. The inventors have shown that one embodiment of SCODA can be used to separate nucleic acid sequences differing only by the presence of a single methylated cytosine residue. Other chemical modifications would be expected to alter the binding energy of a nucleic acid and its complementary sequence in a similar manner. Modification of proteins, such as through methylation, can also alter the binding of a protein of interest with a protein, RNA or DNA aptamer, antibody, or other molecule that binds to the protein at or near the methylation site. Accordingly, embodiments of SCODA can be used to separate differentially modified molecules of interest. While the examples herein are directed to methylation enrichment, SCODA can also be applied to enrichment and selection of molecules with other chemical differences, including, e.g., acetylation.

SCODA, and sequence-specific SCODA, may be used to enrich a specific sequence of methylated DNA out of a background of methylated and unmethylated DNA. In this application of SCODA, the strength of the SCODA focusing force may be related to the binding energy of the target DNA to the bound oligonucleotides. Target molecules with a higher binding energy may be made to focus more strongly than targets with lower binding energy. Methylation of DNA has previously been documented to slightly increase the binding energy of target DNA to its complementary sequence. Small changes in binding energy of a complementary oligonucleotide may be exploited through SCODA to preferentially enrich for methylated DNA. SCODA operating conditions may be chosen, for example as described above, such that the methylated DNA is concentrated while unmethylated DNA of the same sequence is washed off the gel.

Some embodiments can separate molecules with a difference in binding energy to an immobilized agent of less than kT, the thermal excitation energy of the target molecules. Some embodiments can separate molecules with a difference in binding energy to an immobilized agent of less than 0.19 kcal/mol. Some embodiments can separate molecules with a difference in binding energy to an immobilized agent of less than 2.6 kcal/mol. Some embodiments can separate molecules with a difference in binding energy to an immobilized agent of less than 3.8 kcal/mol. Some embodiments can separate molecules that differ only by the presence of a methyl group. Some embodiments can separate nucleic acid sequences that differ in sequence at only one base.

Generation of a Time Varying Temperature Gradient

Embodiments of SCODA that use variations in temperature as the mobility altering field may use a periodically varying temperature gradient to produce a convergent velocity field. A periodically varying temperature gradient may be provided in any suitable manner, for example by the use of heaters or thermoelectric chillers to periodically heat and cool regions of the medium, the use of radiative heating to periodically heat regions of the medium, the application of light or radiation to periodically heat regions of the medium, Joule heating using the application of an electric field to the medium, or the like.

A periodically varying temperature gradient can be established in any suitable manner. For example, a temperature gradient may allow a particle increased mobility (i.e. at a higher temperature) when a driving field is applied toward the focus spot than when a driving field is applied away from the focus spot. In some embodiments, the temperature gradient is rotated to produce a convergent velocity field in conjunction with the application of a time-varying driving force.

In some embodiments, Joule heating using an electric field is used to provide a temperature gradient. In some embodiments, the electric field used to provide Joule heating to provide a temperature gradient is the same as the electric field that provides the driving field. In some embodiments, the magnitude of the electric field applied is selected to produce a desired temperature gradient within an matrix.

In some embodiments, a spatial temperature gradient is generated using a quadrupole electric field to provide the Joule heating. In some such embodiments, a two dimensional gel with four electrodes is provided. Voltages are applied to the four electrodes such that the electric field in the gel is non-uniform, containing regions of high electric field (and consequently high temperature) and low electric field. The electric field is oriented such that the regions of high electric field tend to push negatively charged molecules towards the center of the gel, while regions of low electric field tend to push such molecules away from the center of the gel. In some such embodiments, the electric field that provides the temperature gradient through Joule heating is also the electric field that applies a driving force to molecules in the gel.

Figure 4:
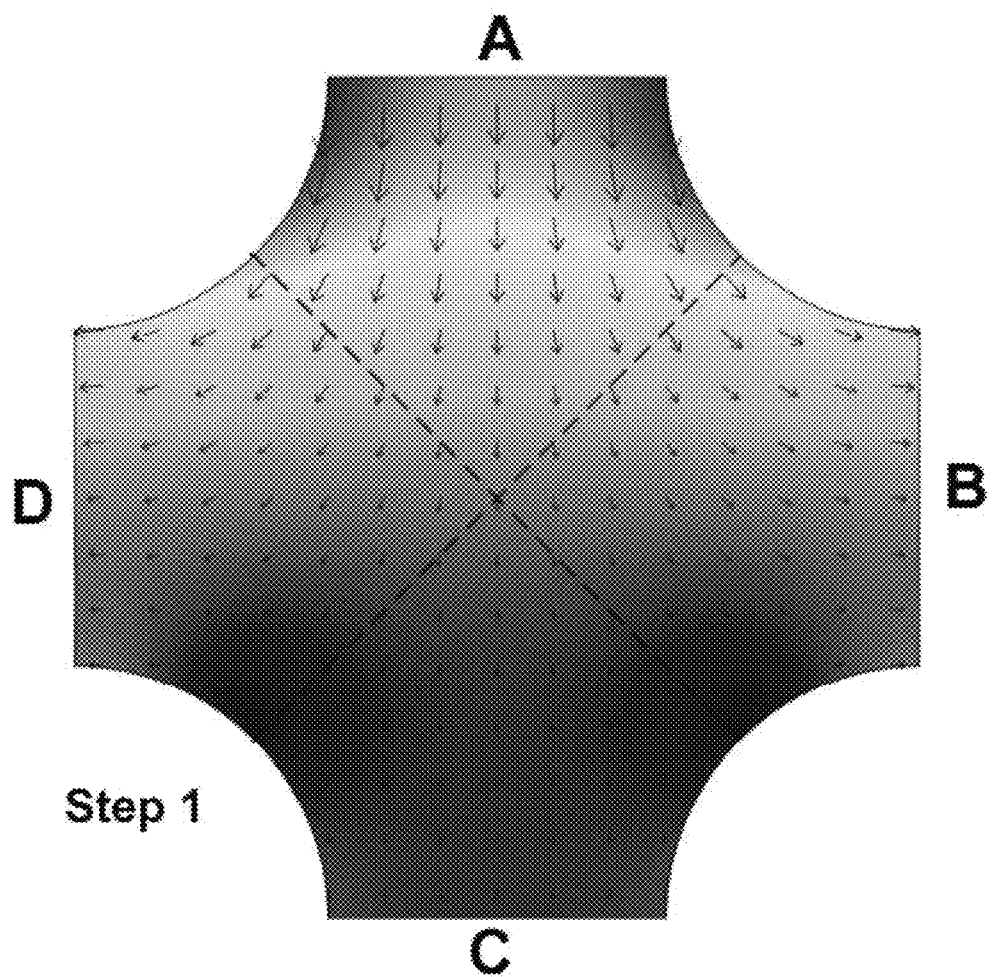
FIG. 4 shows an example of an electric field pattern suitable for two dimensional SCODA based concentration in some embodiments. Voltages applied at electrodes A, B, C, and D, are −V, 0, 0, and 0 respectively. Arrows represent the velocity of a negatively charged analyte molecule such as DNA. Color intensity represents electric field strength.

An example of such a field pattern is illustrated in FIG. 4. Voltages applied at electrodes A, B, C and D in FIG. 4 are –V, 0, 0, and 0 respectively. Arrows represent the velocity of a negatively charged analyte molecule. Color intensity represents electric field strength. The regions near electrode A have a high electric field strength, which decreases towards electrode C. The high field regions near electrode A tend to push negatively charged molecules towards the center of the gel, while the lower field regions near electrodes B, C, and D tend to push negatively charged molecules away from the center of the gel. In embodiments in which the electric field also provides the temperature gradient, the matrix will become hotter in regions of higher field strength due to Joule heating. Hence, regions of high electric field strength will coincide with regions of higher temperature and thus higher mobility. Accordingly, molecules in the high electric field regions near electrode A will tend to move a greater distance toward the center of the gel, while molecules in the lower electric field regions near electrodes B, C, and D have a lower mobility (are at a cooler temperature) and will move only a short distance away from the center of the gel.

Figure 5:
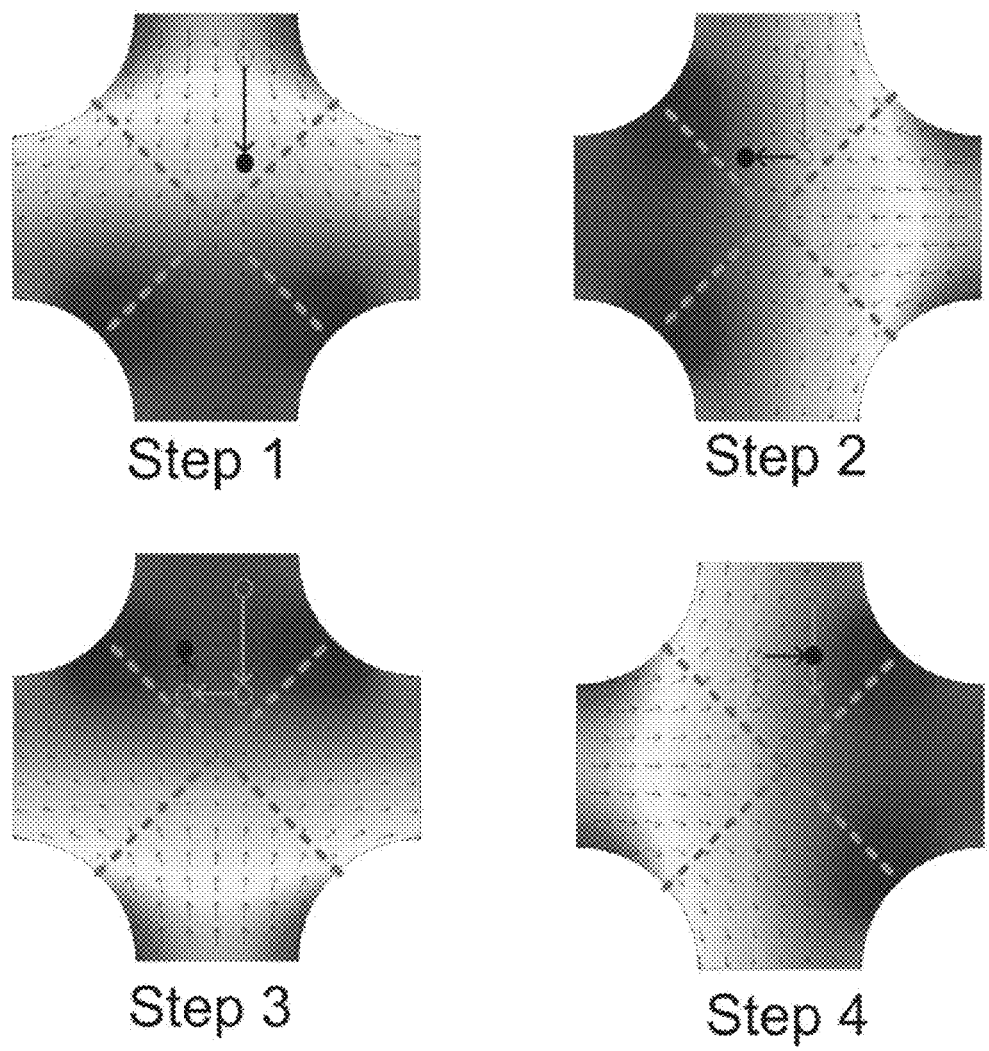
FIG. 5 shows stepwise rotation of the electric field leading to focusing of molecules whose mobility increases with temperature in one embodiment of SCODA. A particle path is shown by the arrows.

In some embodiments, the electric field pattern of FIG. 4 is rotated in a stepwise manner by rotating the voltage pattern around the four electrodes such that the time averaged electric field is zero as shown in FIG. 5. This rotating field will result in net migration towards the center of the gel for any molecule that is negatively charged and has a mobility that varies with temperature. In some embodiments, the electric field pattern is varied in a manner other than rotation, e.g. by sequentially shifting the voltage pattern by 180°, 90°, 180°, and 90°, or by randomly switching the direction of the electric field. As shown above, the mobility of a molecule moving through an matrix depends on temperature, not electric field strength. The applied electric field will tend to increase the temperature of the matrix through Joule heating; the magnitude of the temperature rise at any given point in the matrix will be proportional to the square of the magnitude of the electric field.

In embodiments in which the thermal gradient is provided by Joule heating produced by the electric field that also provides the driving field, the oscillations in the thermal gradient will have the same period as the electric field oscillations. These oscillations can drive SCODA based concentration in a two dimensional gel.

FIG. 5 illustrates the stepwise rotation of the electric field leading to focusing of molecules whose mobility increases with temperature or electric field according to such an embodiment. A particle path for a negatively charged molecule is shown. After four steps the particle has a net displacement toward the center of the gel. Molecules that do not experience a change in mobility with changing temperature or electric field will experience zero net motion in a zero time averaged electric field.

Theoretical Predictions of Focusing and Separation

In some embodiments, the electric field and subsequently the Joule heating within an SCODA gel are controlled by both the voltage applied to the source electrodes, and the shape of the gel. For example, superimposed rotating dipole and quadrupole fields can be used to drive electrophoretic SCODA concentration. The ratio of the strength of these two fields, the dipole to quadrupole ratio (DIQ), has an impact on the efficiency of SCODA focusing with a maximum at around DIQ=4.5, however the optimum is relatively flat with the SCODA force staying relatively constant for values between 1.75 and 10. One convenient choice of DIQ is 2. With this particular choice, only two distinct potentials need to be applied to the source electrodes, which can be achieved by connecting one electrode to a common voltage rail, grounding the other three, and rotating this pattern in a stepwise manner through the four possible configurations as shown in Table 2. Although analog amplifiers can be used and were used in the examples described herein, using a D/Q ratio of 2 allows one to use discrete MOSFET switches, which simplifies and reduces the required size and complexity of the power supplies.

TABLE 2

Voltage pattern for SCODA focusing with D/Q = 2.

| | Electrode A | Electrode B | Electrode C | Electrode D |
|---|---|---|---|---|
| Step 1 | –V | 0 | 0 | 0 |
| Step 2 | 0 | –V | 0 | 0 |
| Step 3 | 0 | 0 | –V | 0 |
| Step 4 | 0 | 0 | 0 | –V |

A starting point for a sequence specific gel geometry was the four-sided gel geometry used for the initial demonstration of electrophoretic SCODA. This geometry can be defined by two numbers, the gel width and the corner radius. The inventors started by using a geometry that had a width of 10 mm and a corner radius of 3 mm. An electro-thermal model of this geometry was implemented in COMSOL MULTIPHYSICS® modeling software (COMSOL, Inc, Burlington Mass., USA) to estimate the electric field and temperature profiles within the gel and establish whether or not those field and temperature profiles could drive concentration of a target with a temperature dependent mobility. The model used simultaneously solves Ohm's Law and the heat equation within the domain, using the power density calculated from the solution of Ohm's Law as the source term for the heat equation and using the temperature solution from the heat equation to determine the temperature dependent electrical conductivity of the electrolyte in the gel.

Figure 6:
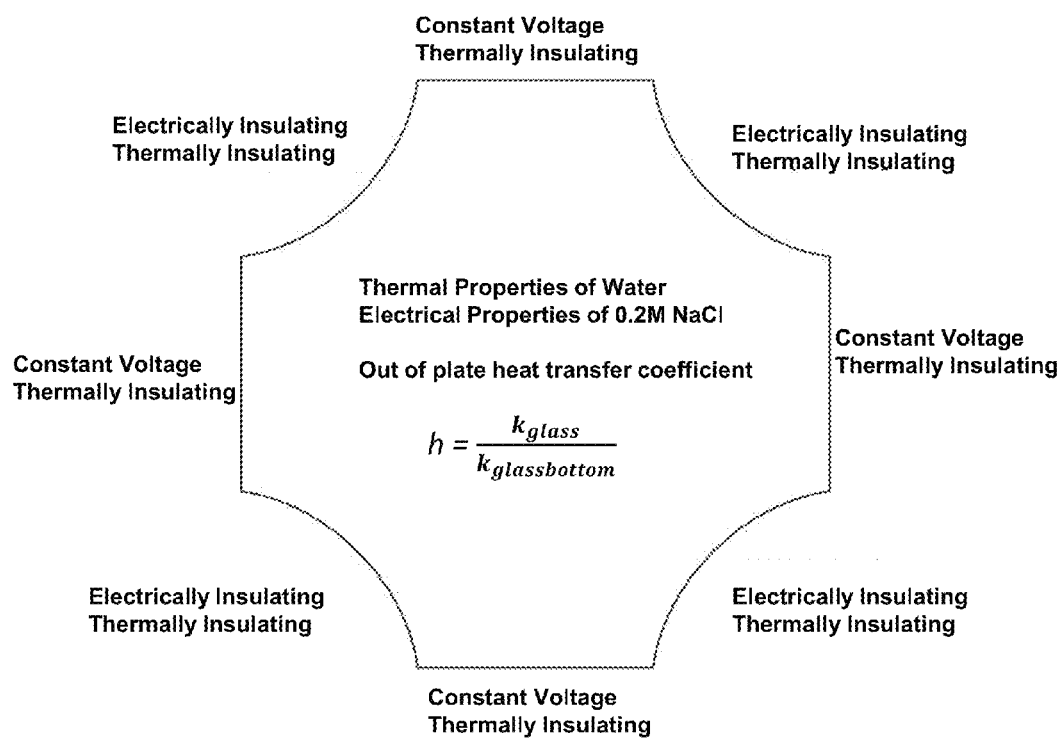
FIG. 6 shows the gel geometry including boundary conditions and bulk gel properties used for electrothermal modeling.
Figure 7:
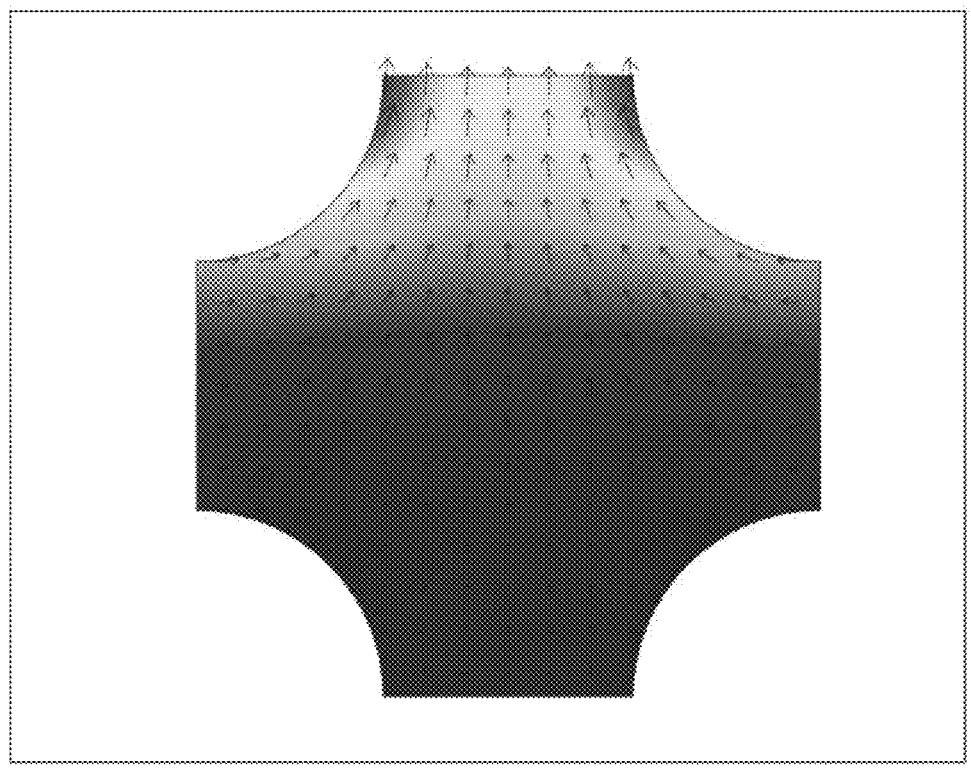
FIG. 7 shows the results of an electrothermal model for a single step of the SCODA cycle in one embodiment. Voltage applied to the four electrodes was −120 V, 0 V, 0 V, 0 V. Spreader plate temperature was set to 55° C. (328 K)
Figure 8:
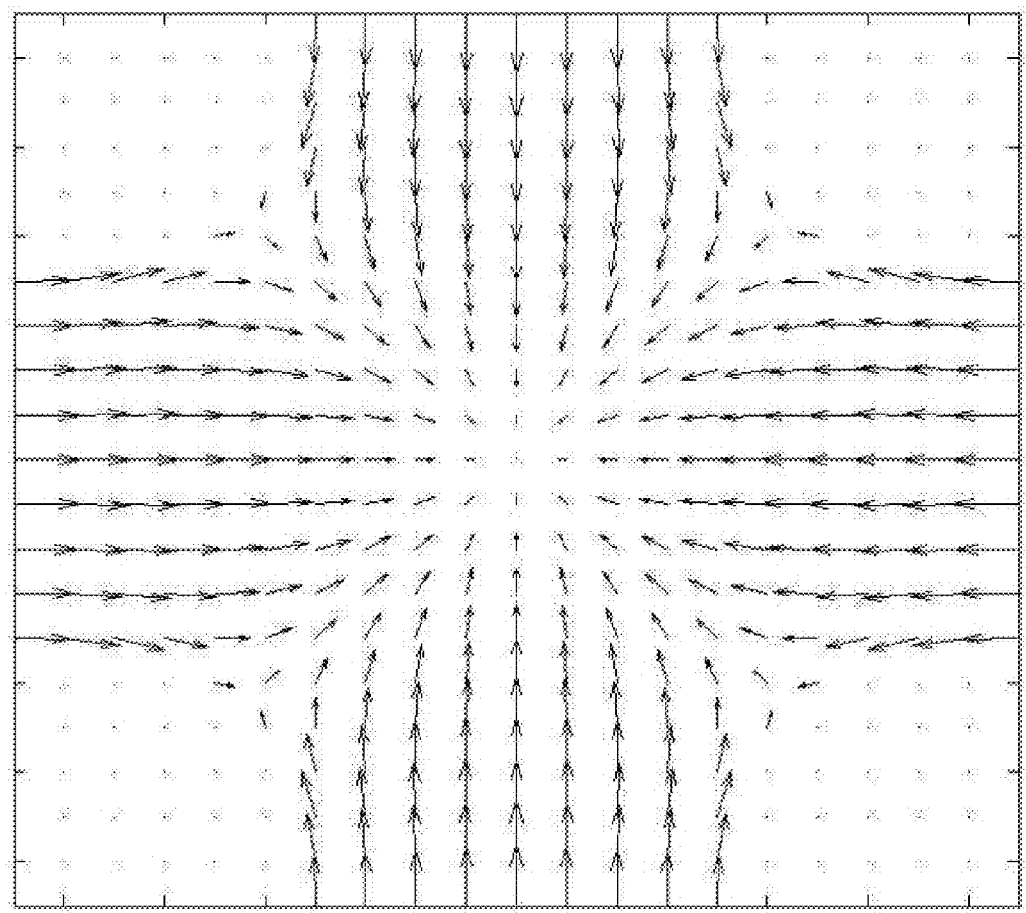
FIG. 8 shows SCODA velocity vector plots in one exemplary embodiment of the invention.

To obtain an accurate estimate of the temperature profile within the gel, the heat conducted out of the top and bottom of the gel are modeled. Boundary conditions and other model parameters are illustrated in FIG. 6. The thermal properties of water and electrical properties of 0.2 M NaCl were used. The gel cassettes are placed on an aluminum spreader plate that acts as a constant temperature reservoir. To model heat flow into the spreader plate the heat transfer coefficient of the glass bottom, given by k/t, was used. The temperature and electric field profiles solved by this model for a single step of the SCODA cycle are shown in FIG. 7. The voltage applied to the four electrodes was −120 V, 0 V, 0 V, 0 V, and the spreader plate temperature was set to 55° C. (328 K). The color map indicates gel temperature and the vector field shows the relative magnitude and direction of the electric field within the gel. Note that as DNA is negatively charged its migration direction will be opposite to the direction of the electric field.

Using experimentally determined values of mobility versus temperature for a given molecule and the thermal model described above, it is possible to determine the SCODA velocity everywhere in the gel for that particular molecule by taking the time average of the instantaneous drift velocity integrated over one complete cycle:

$$\vec{v}_s = \frac{1}{\tau} \int_0^\tau \mu(T(\vec{r}, t)) \vec{E}(\vec{r}, t) dt \qquad (24)$$

where μ is the temperature dependent mobility, E the electric field and τ the period of the SCODA cycle. The temperature and electric field were solved for four steps in the SCODA cycle and coupled with the mobility function. In this manner, the SCODA velocity everywhere in the gel can be calculated. Since discrete steps are being used, if it is assumed that the period is long enough that the phase lag between the electric field and temperature can be neglected, then the integral in equation (24) becomes a sum:

$$\vec{v}_s = \frac{\Sigma \mu(T_i(\vec{r})) \vec{E}_i(\vec{r}) t_i}{\Sigma t_i} \qquad (25)$$

where the velocity is summed over all four steps in the cycle.

In embodiments that are used to separate two similar molecules based on differences in binding for the immobilized probe, a washing force is superimposed over the SCODA focusing fields described above. In some embodiments, the washing force is a DC electric field, described herein as a DC bias. For molecules having to the immobilized probe, the SCODA focusing force applied by the SCODA focusing fields described above will tend to counteract movement of a molecule caused by the washing field, i.e. the SCODA focusing fields will tend to exert a restoring force on the molecules and the molecules will be preferentially focused as compared with molecules having a smaller binding affinity. Molecules that have a smaller binding to the immobilized probe will have a greater mobility through the matrix, and the restoring SCODA force will be weaker. As a result, the focus spot of molecules with a smaller binding affinity will be shifted. In some cases, the restoring SCODA force will be so weak that such molecules with a smaller binding affinity will be washed out of the matrix altogether.

In order to enrich for a specific biomolecule from a population of other similar biomolecules using SCODA, one may operate SCODA focusing electric fields with a superimposed DC bias. The DC bias may move the focused molecules off center, in such a way that the molecules with a lower binding energy to the immobilized binding sites move further off center than the molecules with higher binding energies, thus causing the focus to split into multiple foci. For molecules with similar binding energies, this split may be small while washing under bias. The DC bias may be superimposed directly over the focusing fields, or a DC field may be time multiplexed with the focusing fields.

In one exemplary embodiment used to separate nucleic acids having similar sequences, a DC bias is superimposed over the voltage pattern shown in Table 2, resulting in the voltage pattern shown below in Table 3. In some embodiments, the DC bias is applied alternately with the SCODA focusing fields, i.e. the SCODA focusing fields are applied for a period of time then stopped, and the DC bias is applied for a period of time then stopped.

TABLE 3

Applied voltages for focusing under a DC bias. Shown are values for a 120 V SCODA focusing potential superimposed over a 10 V DC bias.

| | Electrode A | Electrode B | Electrode C | Electrode D |
|---|---|---|---|---|
| Step 1 | −120 | 5 | 10 | 5 |
| Step 2 | 0 | −115 | 10 | 5 |
| Step 3 | 0 | 5 | −110 | 5 |
| Step 4 | 0 | 5 | 10 | −115 |

Figure 15A:
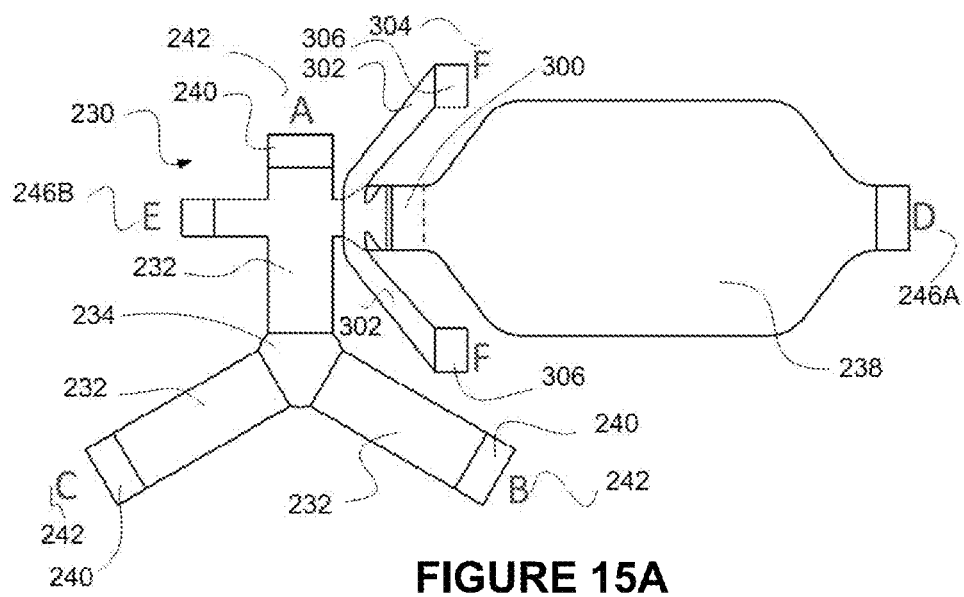
FIG. 15A illustrates a further embodiment of an example apparatus for separating particles with a sample loading interface including a filter gel and a sample loading interface wherein two Peltier elements are provided to independently control the temperature of regions of the sample loading interface and separation arm.
Figure 15B:
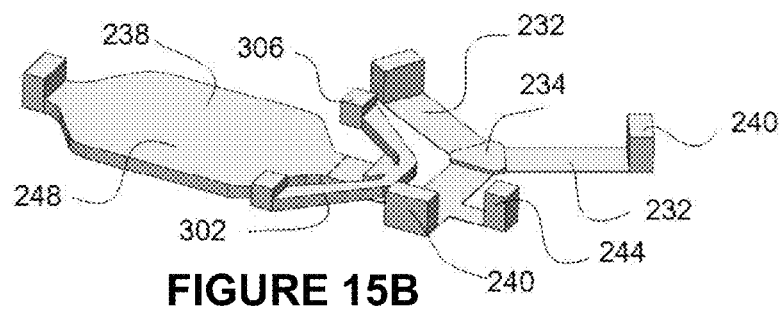
FIG. 15B illustrates a further embodiment of an example apparatus for separating particles with a sample loading interface including a filter gel and a sample loading interface wherein two Peltier elements are provided to independently control the temperature of regions of the sample loading interface and separation arm.
Figure 15C:
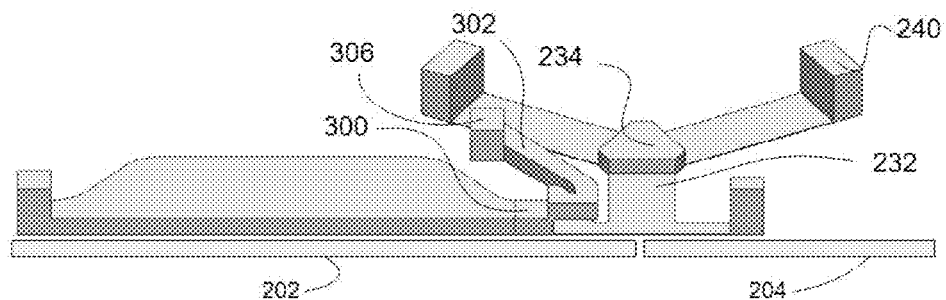
FIG. 15C illustrates a further embodiment of an example apparatus for separating particles with a sample loading interface including a filter gel and a sample loading interface wherein two Peltier elements are provided to independently control the temperature of regions of the sample loading interface and separation arm.
Figure 15D:
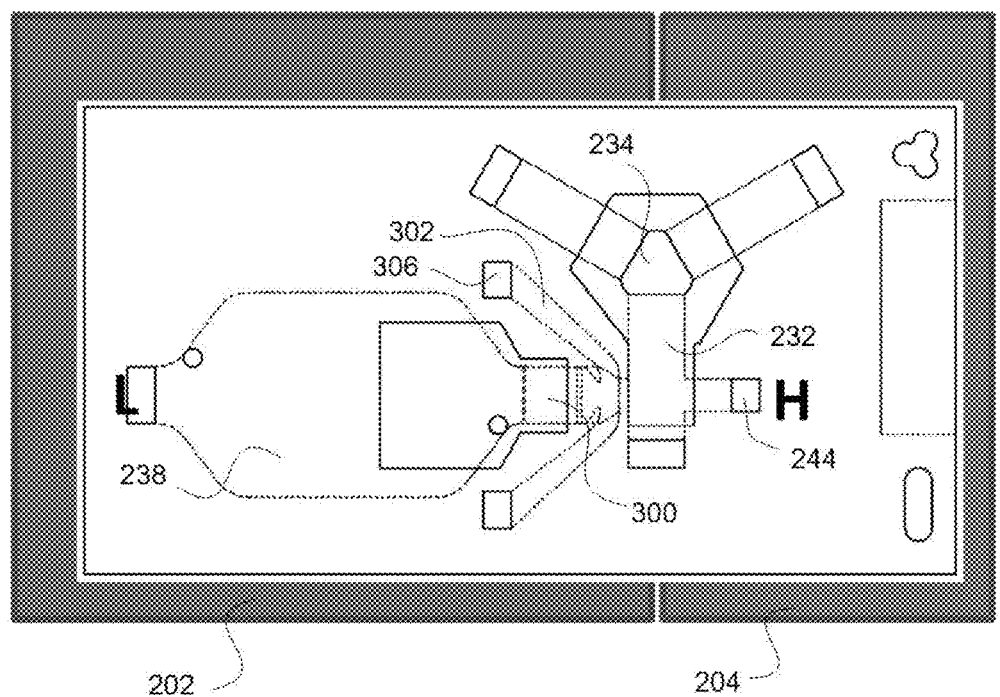
FIG. 15D illustrates a further embodiment of an example apparatus for separating particles with a sample loading interface including a filter gel and a sample loading interface wherein two Peltier elements are provided to independently control the temperature of regions of the sample loading interface and separation arm.

The resulting velocity plots of both the perfect match and single base mismatch targets in the presence of the applied DC bias are shown in FIGS. 15A and 15B, respectively. Electric field and temperature were calculated using COMSOL using a spreader plate temperature of 61° C. The zero velocity location of the perfect match target has been moved slightly off center in the direction of the bias (indicated with a circular spot), however the mismatch target has no zero velocity point within the gel. These calculations show that it is possible to completely wash a target with a smaller binding from the immobilized probe from the gel area while capturing the target with a higher binding affinity, enabling selective purification, concentration and/or detection of a specific sequence, even where the nucleotide targets differ in sequence at only one position.

In some embodiments, the optimal combination of the driving field and the mobility altering field used to perform SCODA focusing where there is a maximum difference in focusing force between similar molecules is empirically determined by measuring the velocity of sample molecules through a medium as a function of the mobility varying field. For example, in some embodiments the mobility of a desired target molecule and a non-desired target molecule at various temperatures is measured in an matrix as described above, and the temperature range at which the difference in relative mobility is greatest is selected as the temperature range for conducting SCODA. In some embodiments, the focusing force is proportional to the rate at which the velocity changes with respect to the perturbing field dv/df, where v is the molecule velocity and f the field strength. One skilled in the art may maximize dv/df so as to maximize SCODA focusing and to enable fast washing of contaminants that do not focus. To maximally separate two similar molecules, SCODA may be carried out under conditions such that $dv_a/df - dv_b/df$ (where $v_a$ is the velocity of molecule a, and $v_b$ is the velocity of molecule b) is maximized.

In some embodiments, the strength of the electric field applied to an matrix is calculated so that the highest temperature within the gel corresponds approximately to the temperature at which the difference in binding between two molecules to be separated is highest.

In some embodiments, the temperature at which the difference in binding between the two molecules to be separated is highest corresponds to the temperature at which the difference between the melting temperature of a target molecule and the agent and the melting temperature of a non-target molecule and the agent is highest. In some embodiments, the maximum difference between the melting temperature of a target molecule and the agent and the melting temperature of a non-target molecule and the agent is less than about 9.3° C., in some embodiments less than about 7.8° C., in some embodiments less than about 5.2° C., and in some embodiments less than about 0.7° C.

In some embodiments, the ratio of target molecules to non-target molecules that can be separated by SCODA is any ratio from 1:1 to 1:10,000 and any value there between, e.g. 1:100 or 1:1,000. In some embodiments, after conducting SCODA, the ratio of non-target molecules relative to target molecules that is located in a focus spot of the target molecules has been reduced by a factor of up to 10,000 fold.

Separation of Particles Having Differing Morphologies

In some embodiments, SCODA can be used to separate particles of different morphologies. For example, in nucleic acids, the morphology of a nucleic acid may differ because of variations in shape (e.g., secondary structure) or because of bonding interactions between complementary (or non-complementary) base pairs. Additionally, sequence deletions, splices, and insertions can result in double stranded nucleic acids with buckles, nicks, etc., resulting in different morphology as compared to other nucleic acids, e.g., wild-type nucleic acids. When morphological differences result in different mobilities in a separation medium, SCODA protocols can be designed to separate the particles.

Because different morphologies result in different melting temperatures, it is possible to separated strand pairings with only a single nucleotide change, regardless of location. Akin to the mobility differences discussed above with respect to targets, mobility differences of double stranded nucleic acids are typically most pronounced over a window of temperatures near the melting temperature ($t_m$). At temperatures below the melting temperature, double stranded nucleic acids of the same approximate length will have approximately the same mobility. At temperatures greater than the melting temperature, double stranded nucleic acids dissociate into their single stranded components and experience decreased mobility. At a temperature in the neighborhood of the melting temperature, however, heteroduplexes and homoduplexes experience different mobilities because the heteroduplex is slightly less stable than the homoduplex due to one or more mismatched bases. Thus, at temperatures in the neighborhood of the melting temperature, heteroduplexed nucleic acid strand pairings can be separated from homoduplexed nucleic acid strand parings.

The velocity of a heteroduplex undergoing scodaphoresis is given by Equation 26:

$$V_{he} = \frac{E_L * t_L}{t}(\mu_{L,he} - \mu_{H,he}) \qquad (26)$$

where $E_L$ is the magnitude of the low field in the SCODA pattern, $t_L$ is the time spent is the low field orientation, t is the total time of one rotation of the SCODA field pattern, and μ is the heteroduplex mobility at the high or low field temperature (T). A similar relationship can be derived for the velocity of a homoduplex, $V_{ho}$:

$$V_{ho} = \frac{E_L * t_L}{t}(\mu_{L,ho} - \mu_{H,ho}) \qquad (27)$$

Figure 9:
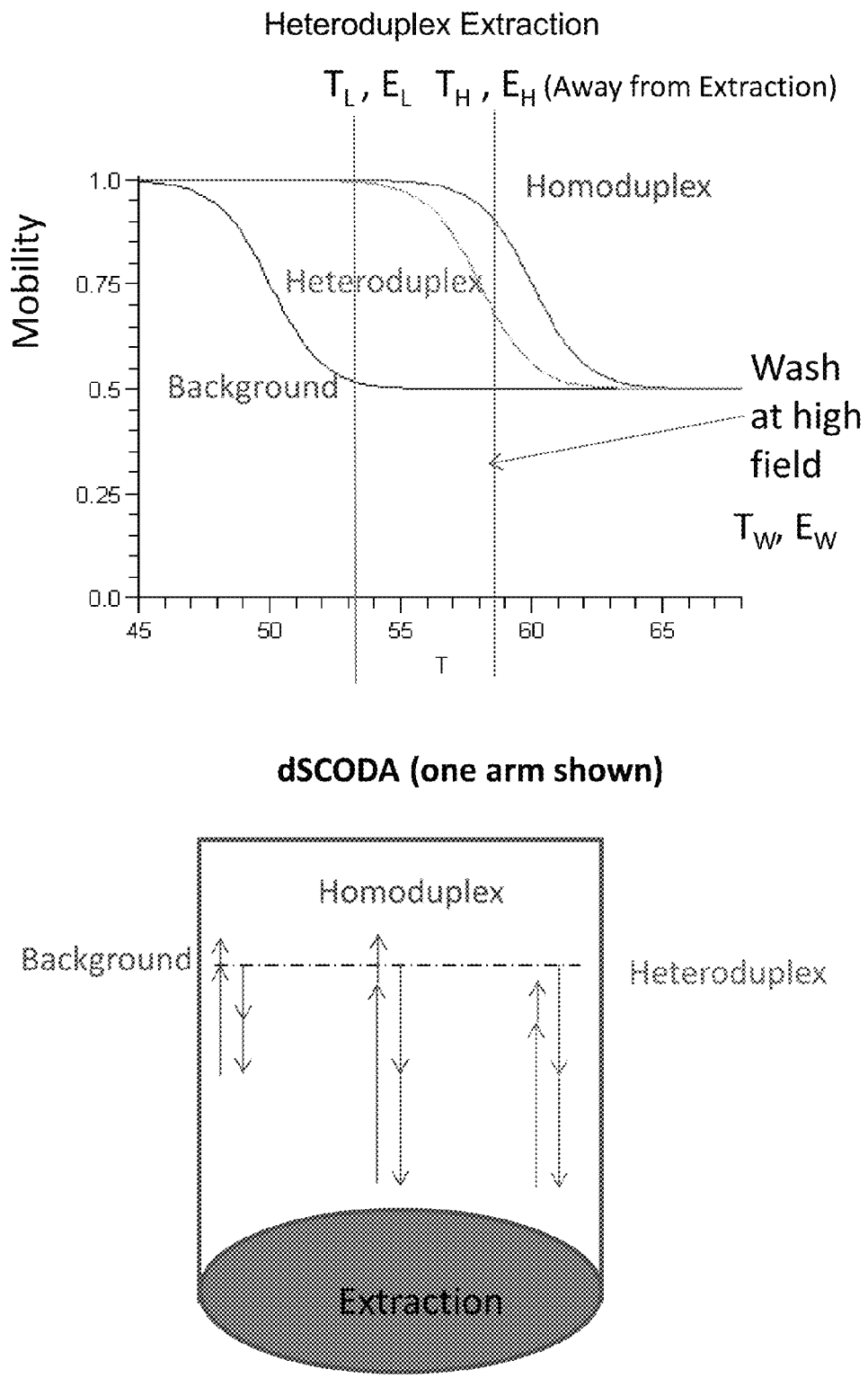
FIG. 9 depicts mobility differences with temperature for a heteroduplexed nucleic acid paring strand and a homoduplexed nucleic acid pairing strand. The choice of low and high field temperatures allows extraction of the heteroduplexed nucleic acid pairing strand.
Figure 10:
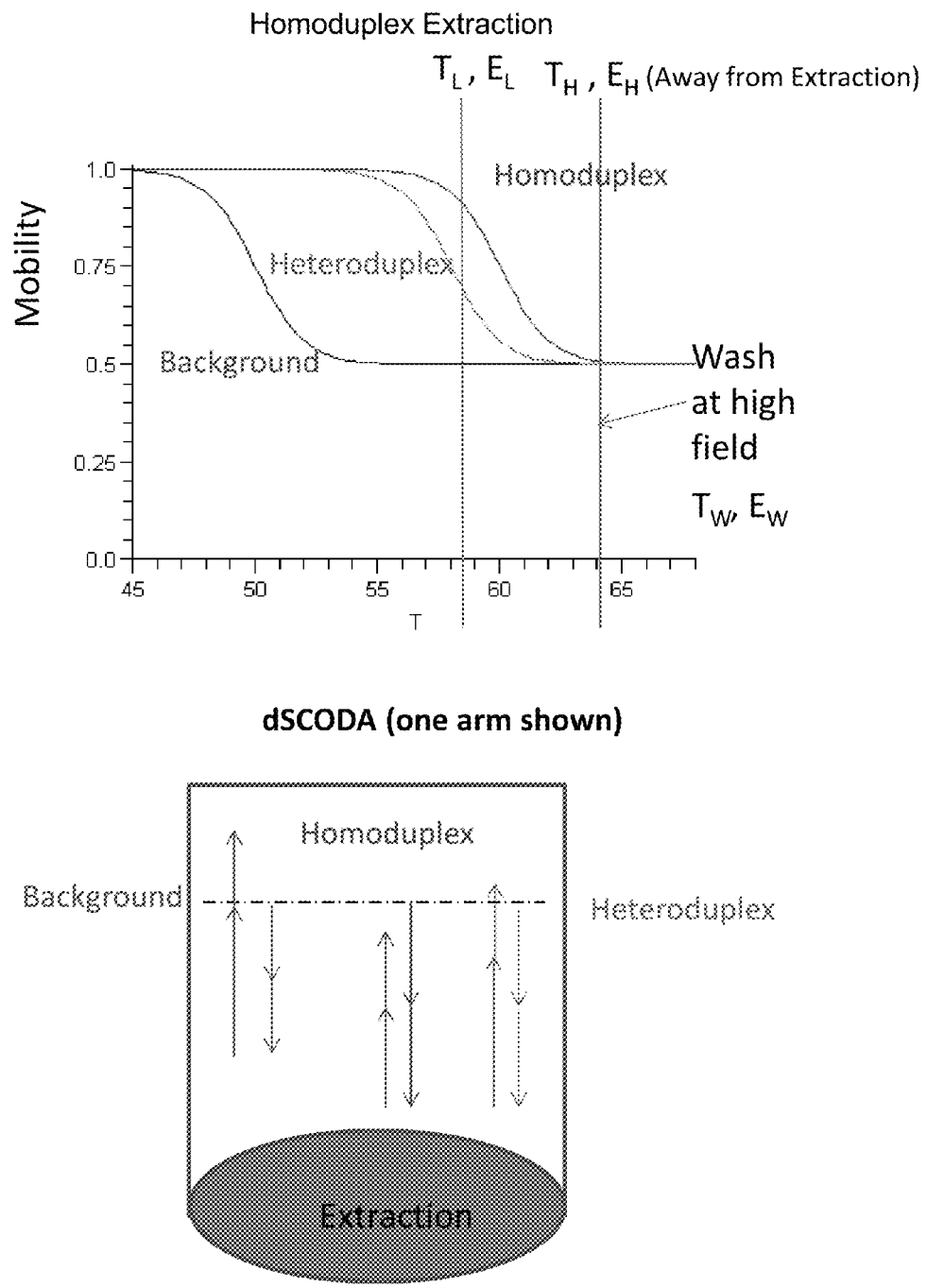
FIG. 10 depicts mobility differences with temperature for a heteroduplexed nucleic acid paring strand and a homoduplexed nucleic acid pairing strand. The choice of low and high field temperatures allows extraction of the homoduplexed nucleic acid pairing strand.

The relationship between temperature (T) and mobility (μ) for a hypothetical heteroduplex nucleic acid strand pairing and a homoduplex nucleic acid strand pairing is shown in FIGS. 9 and 10. In FIGS. 9 and 10, the mobility of the species is normalized to 1 (unitless) and the temperature (T) is given in degrees Celsius. Because this separation method capitalizes on denaturing properties to separate hetero- and homo-duplexes, the method may be generally referred to as "dSCODA" for "denaturing SCODA," or "d-scodaphoresis."

The difference between heteroduplex and homoduplex velocity, $V_{he} - V_{ho}$, can be written as $$\Delta V = \frac{E_L * t_L}{t}(\Delta\mu_H - \Delta\mu_L) \qquad (28)$$

where $\Delta\mu_L = \Delta\mu_{L, ho} - \Delta\mu_{L, he}$, and $\Delta\mu_L = \Delta\mu_{H, ho} - \Delta\mu_{H, he}$. To maximize separation between heteroduplexes and homoduplexes, i.e., ΔV, $\Delta\mu_H$ should be maximized and $\Delta\mu_L$ minimized. As shown in FIG. 9, these conditions can be achieved at $T_L$, or lower, where the mobility of both the homoduplexes and heteroduplexes is the same, and $T_H$, where the difference in the mobility is maximized.

By choosing appropriate field strengths and durations, it is possible to separate the homoduplexes from the heteroduplexes and selectively focus either the homoduplexes or the heteroduplexes in the extraction region. Once in the extraction region the targets can be recovered and further processed, e.g., sequenced. As shown in FIG. 9, an electric field ($E_H$) pushing the particles with greater mobility, i.e., the homoduplexes, away from the extraction region at $T_H$ results in only the heteroduplexes being driven to the extraction region.

In the methods described herein, a wash step is added as the final step of the sequence to drive the homoduplexes and the background away from the extraction. See bottom image of FIG. 9. To minimize background in the selected focused product, it is best to wash the separation medium at a temperature at which the heteroduplexes and the homoduplexes have the greatest difference in mobility. In the instance of heteroduplex extraction, i.e., FIG. 9, a wash step is used while the medium is at $T_H$, resulting in a net negative motion of the background and homoduplexes.

As discussed above the mobility of the particles if variable in the neighborhood of the melting temperature, that is $\mu_{H,he} = \mu_{f,he} * p_{H,he}$, where $\mu_{f,he}$ is the free heteroduplexed mobility with no denaturation (i.e., 1 in FIGS. 9 and 10), and $p_{H,he}$ is the probability of the target not being denatured at a certain temperature. Considering the instance where the heteroduplex and the homoduplex are of the same length, the free mobility of both particles in the separation matrix can be written as $\mu_{f,he} = \mu_{f,ho} = \mu$. Because the low field mobility has been normalized to 1, the net velocity of the heteroduplexes can be rewritten as:

$$V_{he} = \frac{\mu * E_L}{t}(t_L - p_{H,he}(t_L + t_w)) \quad (29)$$

where $t_L$, is the time during which the low electric field is applied, $t_W$ is the time during which the wash is applied, and t is the total time of one rotation of the SCODA field pattern, including wash. A similar equation holds true for the net velocity of particles of the homoduplexes. In short, as expected, the most effective washing to recover the heteroduplex or the homoduplex will be where the difference in temperature mobility is the highest.

In an alternate SCODA scheme, shown in FIG. 10, it is possible to focus the homoduplexes at the extraction region by choosing different temperatures so that $\Delta V$ (equation 46) is maximized but negative. As shown in FIG. 10, this condition is achieved when $T_L$ corresponds to a maximum in differential mobility, while $T_H$ is at the approximate melting temperature of the homoduplex, i.e., a point at which the homoduplexes and heteroduplexes have the same mobility. Because $\Delta V$ in FIG. 10 is in the opposite direction of FIG. 9, the homoduplexes are focused in the extraction region. Furthermore, by coupling this arrangement with a high field wash, as described above, the background in the focused homoduplex product is further reduced.

Regarding equations 27-29, it is clear that there is no need for additional components in the separation matrix to achieve separation on the basis of structural morphology. However, a variety of separation matrices can be used for morphologic separation, e.g., to separate closely related homoduplexes and heteroduplexes. For instance, the separation medium could comprise immobilized particles that do not chemically interact with the duplexed nucleic acids, but cause an increase in the different mobilities of the species as a function of temperature. Alternatively, the extraction could be done in a liquid separation medium in the presence of a tortuous medium such as zeolites or polymer beads.

One of skill will additionally appreciate that the invention can be used to separate a sample based on morphologies different from heteroduplexed versus homoduplexed. For example, the methods could be used to sort nucleic acid strands by length based upon their differential interactions with the medium as a function of temperature. Alternatively, nucleic acids of different organisms or from different subjects (e.g., a mother and a fetus) can be sorted using the described methods.

While the method can be performed on sample that has received little preparative clean up, in many cases, the final results will be improved if the starting sample comprises nucleic acids that are closely related and of similar size. As discussed previously, many applications will benefit from selective amplification of targeted sequence regions and subsequent denaturing and reannealing of the amplicons to create a population of homoduplexed and heteroduplexed nucleic acids. Various methods for preparing a sample for amplification are known. In most instances, the amplification, e.g., PCR, will be limited to reduce introduced errors, e.g., as discussed previously. For example, the a sample may be pre-amplified with 25 or less cycles of PCR, e.g., 20 or less cycles of PCR, e.g., 15 or less cycles of PCR, e.g., 10 or less cycles of PCR, e.g., 5 or less cycles of PCR. Even using small amounts of PCR, the described methods allow isolation of heteroduplexes having strands corresponding to mutation rates of less than 1% compared to the wild-type, e.g., less than 0.5% compared to the wild type, e.g., less than 0.1% compared to the wild type, e.g., less than 0.05% compared to the wild type, e.g., less than 0.01% compared to the wild type.

In some instances, other modifications, e.g., differential methylation or acetylation of nucleic acids will result in morphological differences that can be distinguished with the methods described above. Systems and methods for separating, purifying, concentrating and/or detecting differentially modified molecules as described above can be applied in fields where detection of biomarkers, specific nucleotide sequences or differentially modified molecules is important, e.g. epigenetics, fetal DNA detection, pathogen detection, cancer screening and monitoring, detection of organ failure, detection of various disease states, and the like. For example, in some embodiments SCODA is used to separate, purify, concentrate and/or detect differentially methylated DNA in such fields as fetal diagnostic tests utilizing maternal body fluids, pathogen detection in body fluids, and biomarker detection in body fluids for detecting cancer, organ failure, or other disease states and for monitoring the progression or treatment of such conditions.

In some embodiments, a sample of bodily fluid or a tissue sample is obtained from a subject. Cells may be lysed, genomic DNA is sheared, and the sample is subjected to SCODA. In some embodiments, molecules concentrated using SCODA are subjected to further analysis, e.g. DNA sequencing, digital PCR, fluorescence detection, or the like, to assay for the presence of a particular biomarker or nucleotide sequence. In some embodiments, the subject is a human.

It is known that fetal DNA is present in maternal plasma, and that differential methylation of maternal versus fetal DNA obtained from the maternal plasma can be used to screen for genetic disorders (see e.g. Poon et al., 2002, *Clinical Chemistry* 48:1, 35-41). However, one problem that is difficult to overcome is discrimination between fetal and maternal DNA. SCODA as described above may be used to preferentially separate, purify, concentrate and/or detect DNA which is differentially methylated in fetal DNA versus maternal DNA. For example, SCODA may be used to concentrate or detect DNA which is methylated in the fetal DNA, but not in maternal DNA, or which is methylated in maternal DNA but not fetal DNA. In some embodiments, a sample of maternal plasma is obtained from a subject and subjected to SCODA using an oligonucleotide probe directed to a sequence of interest. The detection of two foci after the application of SCODA focusing fields may indicate the presence of DNA which is differentially methylated as between the subject and the fetus. Comparison to a reference sample from a subject that exhibits a particular genetic disorder may be used to determine if the fetus may be at risk of having the genetic disorder. Further analysis of the sample of DNA obtained through differential modification SCODA through conventional methods such as PCR, DNA sequencing, digital PCR, fluorescence detection, or the like, may be used to assess the risk that the fetus may have a genetic disorder.

One embodiment of the present systems and methods is used to detect abnormalities in fetal DNA, including chromosome copy number abnormalities. Regions of different chromosomes that are known to be differentially methylated in fetal DNA as opposed to maternal DNA are concentrated using SCODA to separate fetal DNA from maternal DNA based on the differential methylation of the fetal DNA in a maternal plasma sample. Further analysis of the separated fetal DNA is conducted (for example using qPCR, DNA sequencing, fluorescent detection, or other suitable method) to count the number of copies from each chromosome and determine copy number abnormalities.

Most cancers are a result of a combination of genetic changes and epigenetic changes, such as changes in DNA methylation (e.g. hypomethylation and/or hypermethylation of certain regions, see e.g. Ehrich, 2002, *Oncogene* 21:35, 5400-5413). SCODA can be used to separate, purify, concentrate and/or detect DNA sequences of interest to screen for oncogenes which are abnormally methylated. Embodiments of SCODA are used in the detection of biomarkers involving DNA having a different methylation pattern in cancerous or pre-cancerous cells than in healthy cells. Detection of such biomarkers may be useful in both early cancer screening, and in the monitoring of cancer development or treatment progress. In some embodiments, a sample obtained from a subject, e.g. a sample of a bodily fluid such as plasma or a biopsy, may be processed and analyzed by differential modification SCODA using oligonucleotide probes directed to a sequence of interest. The presence of two foci during the application of SCODA fields may indicate the presence of differential methylation at the DNA sequence of interest. Comparison of the sample obtained from the subject with a reference sample (e.g. a sample from a healthy patient and/or a sample known to originate from cancerous or pre-cancerous tissue) can indicate whether the cells of the subject are at risk of being cancerous or pre-cancerous. Further analysis of the sample of DNA obtained through differential modification SCODA through conventional methods such as PCR, DNA sequencing, digital PCR, fluorescence detection, or the like, may be used to assess the risk that the sample includes cells that may be cancerous or pre-cancerous, to assess the progression of a cancer, or to assess the effectiveness of treatment.

In some embodiments, a specific nucleotide sequence is captured in the gel regardless of methylation (i.e. without selecting for a particular methylation status of the nucleic acid). Undesired nucleotide sequences and/or other contaminants may be washed off the gel while the specific nucleotide sequence remains bound by oligonucleotide probes immobilized within the separation medium. Then, differential methylation SCODA is used to focus the methylated version of the sequence while electrically washing the unmethylated sequence toward a buffer chamber or another gel where it can then be recovered. In some embodiments, the unmethylated sequence could be preferentially extracted.

In some embodiments, biomolecules in blood related to disease states or infection are selectively concentrated using SCODA. In some embodiments, the biomolecules are unique nucleic acids with sequence or chemical differences that render them useful biomarkers of disease states or infection. Following such concentration, the biomarkers can be detected using PCR, sequencing, or similar means. In some embodiments, a sample of bodily fluid or tissue is obtained from a subject, cells are lysed, genomic DNA is sheared, and SCODA is performed using oligonucleotide probes that are complementary to a sequence of interest. SCODA is used to detect the presence of differentially methylated populations of the nucleic acid sequence of interest. The presence of differentially methylated populations of the target sequence of interest may indicate a likelihood that the subject suffers from a particular disease state or an infection.

In some embodiments, the focusing pattern of the target nucleic acid produced by SCODA from a subject is compared with the focusing pattern of the target nucleic acid produced by SCODA from one or more reference samples (e.g. an equivalent sample obtained from a healthy subject, and/or an equivalent sample obtained from a subject known to be suffering from a particular disease). Similarities between the focusing pattern produced by the sample obtained from the subject and a reference sample obtained from a subject known to be suffering from a particular disease indicate a likelihood that the subject is suffering from the same disease. Differences between the focusing pattern produced from the sample obtained from the subject and a reference sample obtained from a healthy subject indicate a likelihood that the subject may be suffering from a disease. Differences in the focusing pattern produced from the sample obtained from the subject and a reference sample obtained from a healthy subject may indicate the presence of a differential modification or a mutation in the subject as compared with the healthy subject.

Apparatus for Performing SCODA

In some embodiments, SCODA is performed on an electrophoresis apparatus comprising a region for containing the matrix, buffer reservoirs, power supplies capable of delivering large enough voltages and currents to cause the desired effect, precise temperature control of the SCODA medium (which is a gel in some embodiments), and a two color fluorescence imaging system for the monitoring of two different molecules in the SCODA medium.

In an embodiment, the apparatus includes at least three electrodes circumferentially surrounding a central reservoir with a separation medium between at least one electrode and the central reservoir. Circumferentially implies that the electrodes are located around a periphery at a distance from the central reservoir. The electrodes need not be on a circular path, nor do the electrodes have to be individually curved in shape. The electrodes must be electrically separable, so that the electrodes can be individually indexed as described below. The electrodes do not have to fill an amount of the circumferential distance and the electrodes do not have to be of the same shape. Typically, the central reservoir will contain a buffer or an additional separation medium, making it possible to recover the targeted molecules, e.g. for amplification and/or sequencing. In one arrangement, the apparatus includes arms extending outward from the central reservoir, each arm being associated with an electrode.

Embodiments of the present invention can be used to concentrate charged target particles in a collection region while limiting or preventing movement of charged target particles out of the collection region, without the need to place an electrode in the collection region. A separation apparatus with n separation arms, wherein n is at least 3, is provided. All n separation arms are in electrical contact through the collection region. Voltages are applied through the separation arms such that the electric field strength differs between at least one of the separation arms and the remaining arms. The voltage configuration is varied to produce net motion of the charged target particles in a desired direction. Conditions of electric field strength and a variable mobility altering field (which can be the electric field strength in some embodiments) are selected to produce net motion of target particles in a desired direction (i.e. either toward or away from the collection region). Contaminating particles that are not electrically charged, or that have a mobility that does not vary significantly under the application of the mobility altering field, experience little or no net motion under the influence of the electric field. In some embodiments, conditions of electric field strength and mobility altering field are selected so that a contaminating particle that is structurally similar to the target particle (e.g. a methylated form of the target particle or a particle having the same sequence as the target particle with one point mutation) experiences net motion in a direction opposite to the net motion experienced by the target particle. Particles that reach the collection region experience a restoring force upon movement into any one of the separation arms that tends to return such particles to the collection region. Thus, target particles can be collected in the collection region, without the need to provide an electrode in the collection region.

Figure 11:
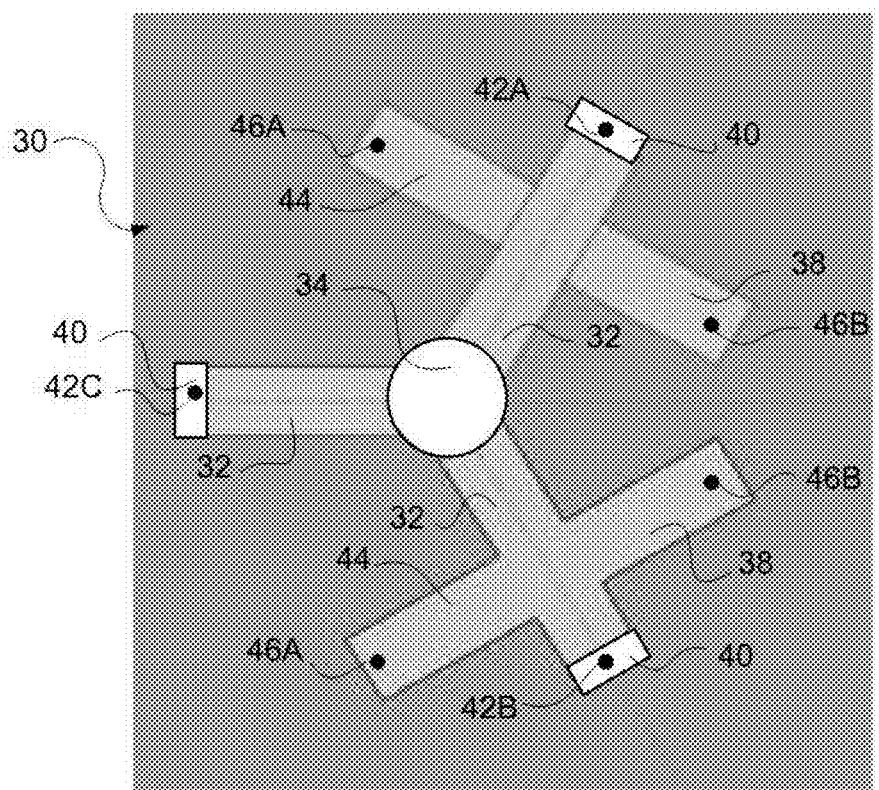
FIG. 11 shows an embodiment of an example apparatus according to one embodiment of the present invention.

FIG. 11 shows an apparatus 30 for separating particles according to one embodiment. Apparatus 30 has three separation arms 32 disposed around a central reservoir 34. In the illustrated embodiment, separation arms 32 are symmetrically disposed around central reservoir 34. Central reservoir 34 provides the collection region in the illustrated embodiment. Separation arms 32 are spaced apart; that is, the ends of separation arms 32 do not directly contact one another, but are separated by central reservoir 34. Each one of separation arms 32 includes separation medium (shown as 136 in FIG. 14B).

As used herein with reference to separation arms 32, the term "length" refers to a direction along separation arm extending between central reservoir 34 and the distal end of separation arm 32. "Width" refers to a direction perpendicular to and in the same plane as "length".

In some embodiments, central reservoir 34 optionally includes separation medium. Removal and extraction of collected target particles is facilitated in embodiments in which central reservoir 34 is filled with buffer.

A buffer chamber 40 is provided at the distal end of each separation arm 32 (i.e. the end opposite central reservoir 34) so that an electric field can be applied to each separation arm. Each buffer chamber 40 is provided with an electrode, shown schematically as 42A, 42B and 42C, so that an electric field can be applied to each separation arm 32.

Electrically charged target particles in a sample can be injected into a separation arm 32 by applying an electric field that drives the charged target particles into the separation arm. In some embodiments, injection of electrically charged target particles is done perpendicular to the direction that particles travel within separation arm 32, so that contaminating particles are not drawn to the central reservoir 34 during sample loading. Alternatively, target particles can be injected into separation arm 32 in any suitable manner, for example via the distal ends of separation arms 32, or vertically from a reservoir positioned above separation arms 32.

In the illustrated embodiment, at least one separation arm 32 is provided with a loading reservoir 38. Loading buffer chambers 44 are provided on the sides of separation arms 32 opposite loading reservoir 38. Loading electrodes, shown schematically as 46A, are provided in each loading buffer chamber 44. Complementary loading electrodes, shown schematically as 46B, are provided in each loading reservoir 38. In use, a sample is injected into one or more separation arms 32 by loading the sample in the appropriate loading reservoir(s) 38. A suitable potential difference is applied across opposing loading electrodes 46A, 46B to inject electrically charged components of the sample into separation medium 36 within separation arms 32. For example, where the target particles are nucleic acids, which are typically negatively charged, a positive voltage is applied to electrode 46A and a negative voltage is applied to electrode 46B to inject the nucleic acids into separation arm 32.

In some embodiments, a single loading reservoir is used to load the sample into multiple separation arms 32. In such embodiments, a single electrode 46B can be used in conjunction with several electrodes 46A to load the sample.

Electrically charged particles can be loaded in any suitable manner, including from above the separation arms and/or from the distal ends of the separation arms. In the illustrated embodiment, loading buffer chambers 44 are positioned towards the distal ends of separation arms 32 (i.e. the ends of separation arms 32 away from central reservoir 34). Loading buffer chambers 44 are configured to inject electrically charged particles perpendicularly into separation arms 32 so that the paths of travel of the charged particles entering a separation arms 32 extend across the width of the separation arm 32. Injection of electrically charged particles perpendicularly into separation arms 32 as in the illustrated embodiment minimizes the risk that non-target particles will reach central reservoir 34 during the injection process.

After the sample has been injected into separation arms 32, voltages are applied to electrodes 42A, 42B and 42C to produce an electric field and cause movement of particles within separation arms 32 (i.e. to provide a driving field). The direction of the driving field in a given separation arm 32 is varied from time to time. Concurrently with the application of the driving field, but not necessarily simultaneously, a mobility altering field is applied to vary the mobility of particles within separation arms 32. The effect of the mobility altering field is varied from time to time. In some embodiments, the electric field is both the driving field and the mobility altering field.

In some embodiments, including the illustrated embodiment, the electric field that provides the driving field also provides the mobility altering field. For example, for particles that have a mobility that varies with electric field strength, e.g. nucleic acids such as DNA or RNA, the applied electric field can provide both the driving field and the mobility altering field. For example, the following voltage patterns may be applied across electrodes 42A, 42B and 42C:

TABLE 4

Exemplary voltage pattern for embodiment with three separation arms.

| Step | Electrode 42A | Electrode 42B | Electrode 42C |
|------|---------------|---------------|---------------|
| 1 | H | H | L |
| 2 | L | H | H |
| 3 | H | L | H |

Where "H" represents a high voltage applied to the electrode, and "L" represents a low voltage applied to the electrode. At times when the voltage applied to an electrode associated with a particular separation arm 32 is high, the electric field strength in that particular separation arm 32 will be low. In the illustrated embodiment, the current flowing through separation arm 32C in step 1 will be twice the current flowing through either one of separation arms 32A or 32B in embodiments in which all separation arms have the same impedance (i.e. the amount of current flowing through separation arm 32C must equal the sum of the amount of current flowing through separation arms 32A and 32B). Thus, the electric field strength in separation arm 32C in this high electric field strength condition will be twice the electric field strength in either of separation arms 32A or 32B. Each of steps 1, 2 and 3 represents a discrete configuration of the driving field (the electric field) and the mobility altering field (the electric field) for this exemplary embodiment. The application of each of steps 1, 2 and 3 one time represents one cycle.

In some embodiments, the high voltage may be any voltage between 100 V and 1000 V, e.g. 100 V, 125 V, 150 V, 175 V, 200 V, 225 V, 250 V, 275 V, 300 V, 325 V, 350 V, 375 V. 400 V, 425 V, 450 V. 475 V, 500 V, 525 V, 550 V. 575 V, 600 V, 625 V, 650 V, 675 V. 700 V. 725 V. 750 V. 775 V. 800 V. 825 V. 850 V. 875 V, 900 V, 925 V, 950 V. 975 V, or 1000 V and the low voltage may be any voltage lower than the high voltage. The polarity of the voltage is selected depending on the charge of the target particles (positive or negative). The low voltage is 0 V in some embodiments. The effect of applying the voltages summarized in Table 4 on a negatively charged molecule from a sample that has a mobility that varies with electric field strength, for example a nucleic acid such as DNA or RNA, is illustrated schematically in FIG. 12 and described below with reference to the movement of an exemplary polynucleotide molecule. In step 1, separation arms 32A and 32B are regions of low electric field strength. Arm 32C is a region of high electric field strength, as indicated by diagonal shading. Negatively charged particles, such as polynucleotides, in separation arms 32A and 32B will move in a direction away from central reservoir 34 by a distance $\mu_L E_L t$, where $\mu_L$ is the mobility of the particle at the low electric field strength, $E_L$ is the low electric field strength, and t is the time for which the low electric field is applied. This movement is indicated schematically by arrows 50A, 50B. This motion will coincide with the time interval during the period of the cycle in which the electric field strength is low, and in which the mobility of the polynucleotides through separation medium 36 is lower (due to the relatively low electric field strength in separation arms 32A, 32B). Thus, the distance traveled by the polynucleotides located in separation arms 32A and 32B away from central reservoir 34 will be relatively small.

In step 2, separation arms 32B and 32C are regions of low field strength, as indicated by an absence of shading, while separation arm 32A is a region of high field strength, as indicated by diagonal shading. Negatively charged particles, such as polynucleotides, in separation arm 32B will again move in a direction away from central reservoir 34, as indicated by arrow 52B. This motion will coincide with the time interval during the period of the cycle in which the electric field strength is relatively low and in which the mobility of the polynucleotides through separation medium 36 is lower (due to the low electric field strength in separation arm 32B). Thus, the distance traveled by polynucleotides in separation arm 32B ($\mu_L E_L t$) away from central reservoir 34 will be relatively small. Negatively charged particles, such as polynucleotides, in separation arm 32A will move in a direction toward central reservoir 34, as indicated by arrow 54A. This motion will coincide with the time interval during the period of the cycle in which electric field strength is high and in which the mobility of the polynucleotides through separation medium 36 is higher (due to the high electric field strength in separation arm 32A). Thus, the distance traveled by the polynucleotides in separation arm 32A toward central reservoir 34 will be relatively large, and can be described as $\mu_H E_H t$, where $\mu_H$ is the mobility of the polynucleotide particle at the high electric field strength condition, $E_H$ is the high electric field strength, and t is the time for which the high electric field strength is applied.

In step 3, separation arms 32A and 32C are regions of low field strength, while separation arm 32B is a region of high field strength. Negatively charged 30 particles, such as polynucleotides, in separation arm 32A will move in a direction away from central reservoir 34, as indicated by arrow 52A. This motion will coincide with the time interval during the period of the cycle in which the electric field strength in separation arm 32 is low and in which the mobility of the polynucleotides through separation medium 36 is lower (due to the low electric field strength in separation arm 32A). Thus, the distance traveled by polynucleotides in separation arm 32A ($\mu_L E_L t$) in a direction away from central reservoir 34 will be relatively small. Negatively charged particles, such as polynucleotides, in separation arm 32B will move in a direction toward central reservoir 34, as indicated schematically by arrow 54B. This motion will coincide with the time interval during the period of the cycle in which the electric field strength is high and in which the mobility of the polynucleotides through separation medium 36 is higher (due to the high electric field strength in separation arm 32B). Thus, the distance traveled by the polynucleotides in separation arm 32B ($\mu_H E_H t$) toward central reservoir 34 will be relatively large.

In this example, negatively charged particles that do not have a mobility that varies with electric field strength, or that does not vary significantly with electric field strength (i.e. for which $\mu_L$ is equal or similar to $\mu_H$) will tend to experience zero net motion towards or away from central reservoir 34, because the times and electric field strengths have been selected such that the magnitude of the steps taken away from central reservoir 34 by such particles as represented, for example, by arrows 50A and 52A will tend to be equal or nearly equal to the magnitude of the steps taken towards central reservoir 34 by such particles, as represented, for example, by arrow 54A. That is, because the electric field strength at times of low electric field strength is ½ the electric field strength at times of high electric field strength, and because the particle experiences the low electric field strength for twice the length of time as the high electric field strength, the net motion of the particle will tend to be zero or close to zero.

Steps 1, 2 and 3 can be repeated to effect net motion of target particles that have a mobility that varies with electric field strength within separation arms 32. In some embodiments, operating conditions including the electric field strength and the length of time the electric field is applied are selected so that the motion of target particles toward central reservoir 34 during times of high electric field strength (illustrated as arrows 54A, 54B) is greater than twice as large as the total motion away from central reservoir 34 during times of low electric field strength during one cycle (illustrated as arrows 50A, 50B and 52A, 52B). That is, the average distance traveled by the target particles during all times of low electric field strength in one cycle is less than the average distance traveled by the target particles during times of high electric field strength in one cycle. In this manner, target particles can be concentrated in central reservoir 34 if the polarity of the applied voltage is selected appropriately. In the described exemplary embodiment, particles that have a mobility that varies with electric field strength (e.g. polynucleotides) can be separated from particles that have a mobility that does not vary with electric field strength, or which varies to a lesser extent with electric field strength (e.g. proteins).

Figure 12:
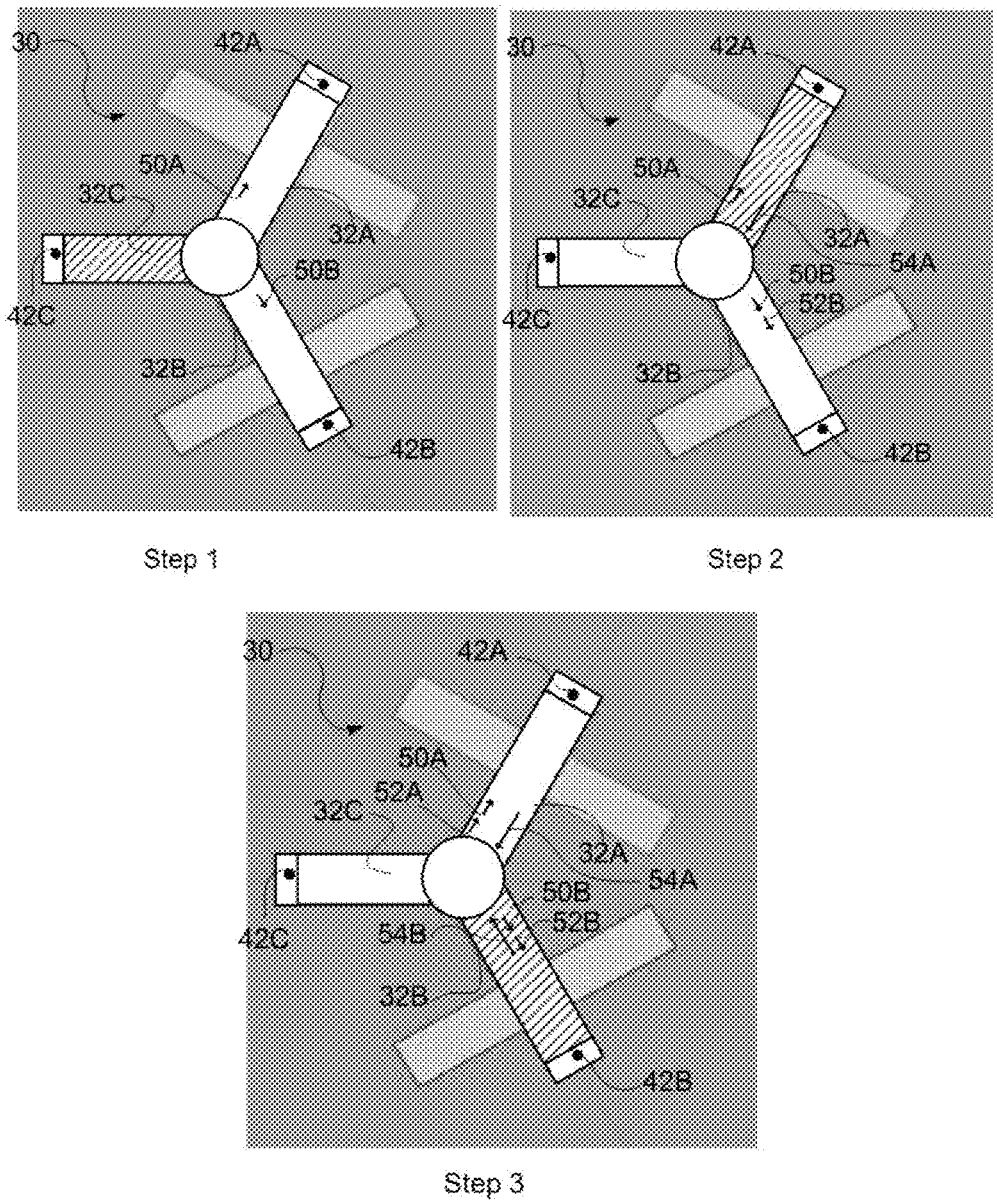
FIG. 12 shows the movement of a hypothetical particle under applied electric fields in an exemplary embodiment.

It is not necessary that the electric field pattern be rotated as described above with respect to steps 1, 2 and 3 as illustrated in FIG. 12. For example, the electric field pattern could be applied using random or occasionally varying combinations of the configuration of steps 1, 2 and 3. As long as the electric field pattern is such that the electric field in each separation arm containing target particles to be separated spends approximately ⅓ of the time in the high electric field strength configuration and approximately ⅔ of the time in a low electric field strength configuration, the net motion of the target particles will be towards central reservoir 34. Similarly, in an embodiment having n separation arms as described below, net motion of target particles towards central reservoir 34 can be effected in each one of the separation arms if the electric field pattern in that separation arm spends, on average, approximately 1/n of the time in the high electric field strength configuration and approximately (n−1)/n of the time in the low electric field strength configuration.

Apparatus 30 could be provided with any desired number n of separation arms 32, where n is greater than or equal to 3. For example, in some embodiments, apparatus 30 has 4, 5, 6, 7, 8, 9, 10, 11 or 12 separation arms 32. At least three separation arms are required so that the electric field strength can be varied as described above.

In embodiments where there are three or more separation arms and central reservoir 34 contains buffer, particles that enter central reservoir 34 will experience a net restoring force towards the separation arm that they came from (because the mobility of the particles will not vary within the buffer contained in central reservoir 34) and will tend to collect at the interface between the separation arm and central reservoir 34. The number of separation arms to be used in a particular embodiment would be determined by one skilled in the art depending on the nature of the particles to be separated using apparatus 30. The voltage patterns applied to such an apparatus would be similar. For example, Table 5 illustrates an exemplary voltage pattern that could be applied to an apparatus having six separation arms 32. In the exemplary embodiment, one separation arm is at a high electric field strength and the remaining (n−1) separation arms are at a low electric field strength in each cycle, similar to the embodiment described above.

TABLE 5

Exemplary voltage pattern for embodiment with six separation arms, each having one electrode, identified below as A, B, C, D, E or F.

| Step | Electrode | | | | | |
| --- | --- | --- | --- | --- | --- | --- |
| | A | B | C | D | E | F |
| 1 | H | H | L | H | H | H |
| 2 | H | H | H | L | H | H |
| 3 | H | H | H | H | L | H |
| 4 | H | H | H | H | H | L |
| 5 | L | H | H | H | H | H |
| 6 | H | L | H | H | H | H |

Providing a larger number of separation arms 32 can increase the significance of the electric field dependence of the net motion of particles within separation arms 32. That is, the magnitude of the difference between the electric field strength at the high electric field strength condition versus at the low electric field strength condition will be greater in embodiments having a larger number of separation arms 32. Particles that have a mobility in medium 36 that is highly dependent on electric field strength will tend to move a relatively larger amount in the direction of arrows 54A, 54B under conditions of higher field strength. Also, a greater number of steps in the direction of arrows 50A, 50B and 52A, 52B will be taken. Specifically, particles will take n−1 steps in the direction away from central reservoir 34, where n is the number of separation arms 32, for each step taken toward central reservoir 34.

In contrast, providing a smaller number of separation arms 32, e.g. three separation arms as shown in the illustrated embodiment, will decrease the significance of the electric field dependence of a particle's mobility on the net movement of that particle within separation arms 32. In some embodiments, for example those that exploit a binding interaction between the target particle and the medium assist in or effect separation, and/or those embodiments in which a field other than electric field strength (e.g. temperature, light, pH or salt concentration) is used as the mobility altering field, decreasing the significance of the electric field dependence of a particle's mobility on the net movement of that particle as aforesaid enhances separation of such target particles from other similar particles that share a similar electric field dependence of mobility (e.g. oligonucleotides of a similar length).

While the exemplary embodiments have been described above with reference to one separation arm having a high electric field strength while the remaining (n−1) separation arms have a low electric field strength, alternative embodiments could provide a high electric field strength in more than one separation arm at a time. For example, in the exemplary embodiment having six separation arms, two separation arms could be provided with a high electric field strength and four separation arms provided with a low electric field strength and the electric field pattern could be rotated.

Separation arms 32 need not be symmetrically disposed as illustrated. Separation arms 32 need not be generally rectangular in shape as illustrated. Separation arms 32 need not extend in straight lines as illustrated. A symmetrical arrangement of separation arms can help to provide a uniform electric field strength in each of the separation arms. Configurations of apparatus 30, including separation arms 32 and central reservoir 34, that interfere appreciably with the uniform flow of electric current through each separation arm 32 should be avoided if maximum efficiency is desired.

Separation arms 32A, 32B and 32C need not all have the same shape as one another as illustrated. For example, the widths, lengths and/or shape of separation arms 32 could be varied relative to one another, provided that the overall volume and geometry is such that the electric fields are matched in each separation arm 32. Where the separation arms will be loaded with particles to be separated, the configuration of the separation arms should be selected so that the driving and mobility altering fields will be consistent across all configurations of a cycle. For example, in embodiments in which the electric field is both the driving field and the mobility altering field, the geometry of each separation arm and the applied voltage should be selected so that the field strength is consistent across any given cross section of the width of each separation arm loaded with sample for each configuration of the electric field. In embodiments in which the electric field is the driving field and Joule heating is used to generate heat so that temperature is used in whole or in part as the mobility altering field, the geometry of each separation arm and the applied voltage should be selected so that the temperature and electric field strength are consistent across any given cross-section of the width of each separation arm loaded with sample for each configuration of the electric field, and so that equilibrium points are avoided. If a particular separation arm will not be loaded with particles to be separated, that particular separation arm can have any desired geometry. In some such embodiments, the impedance of that particular separation arm is approximately the same as the impedance of the other separation arms to avoid creation of a bias.

Figure 13A:
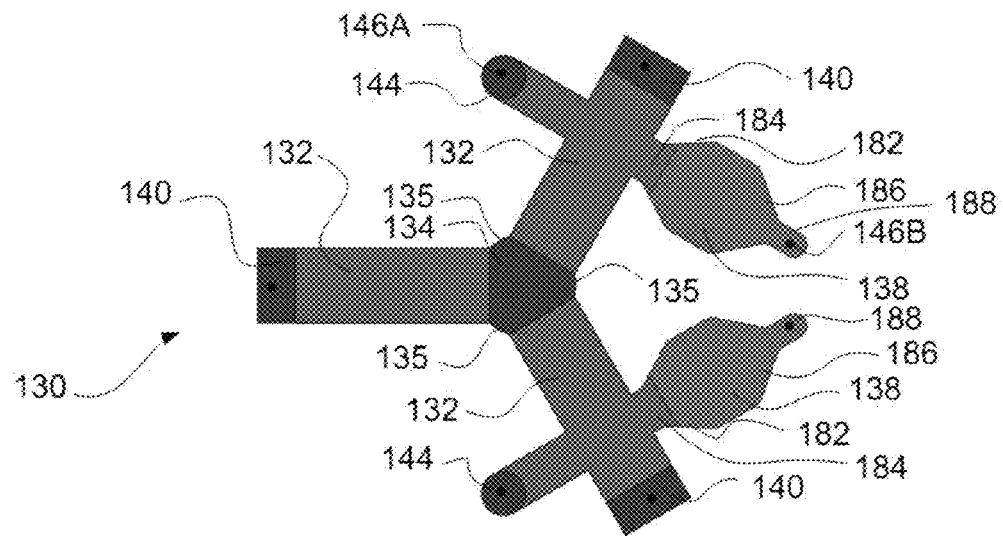
FIG. 13A is a top view showing schematically the configuration of a separation medium according to another embodiment.
Figure 13B:
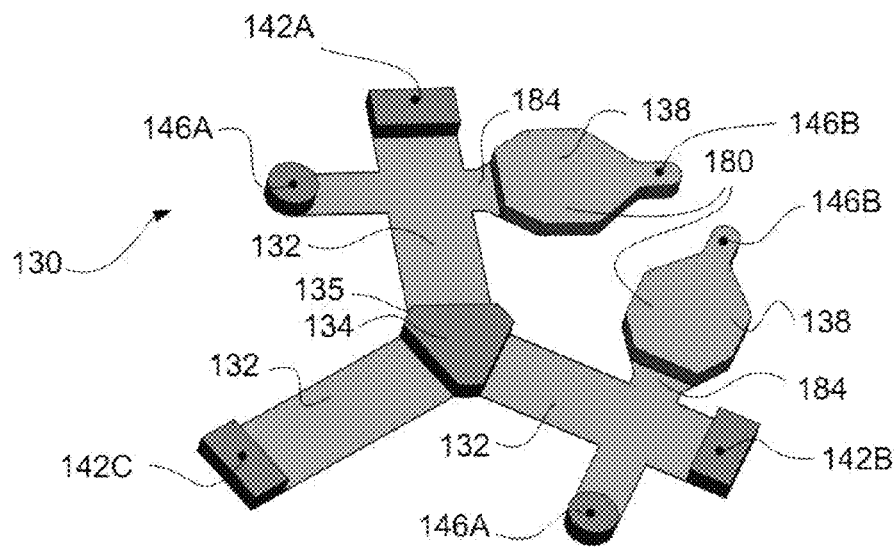
FIG. 13B is a perspective view of the separation medium of FIG. 13A.
Figure 13C:
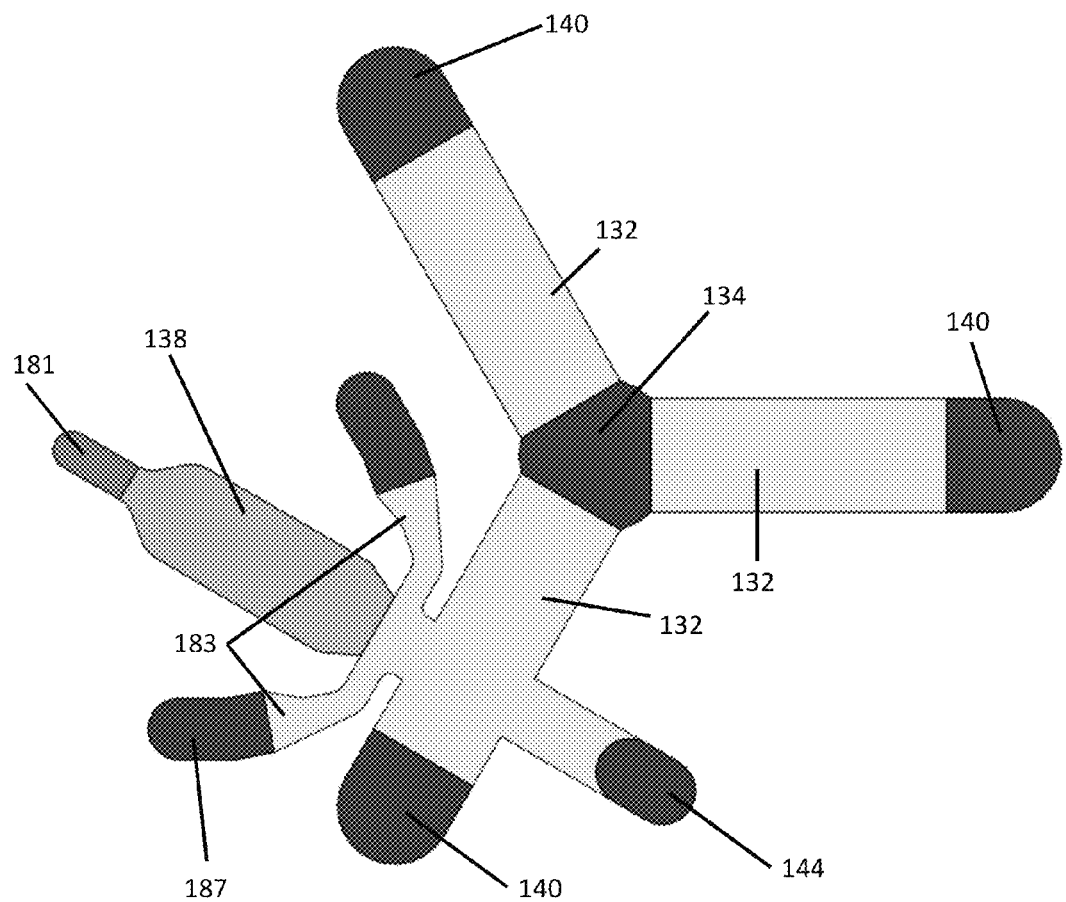
FIG. 13C is a top view of an alternate embodiment of FIG. 13A having streamlines that help constrain the sample during injection.
Figure 14A:
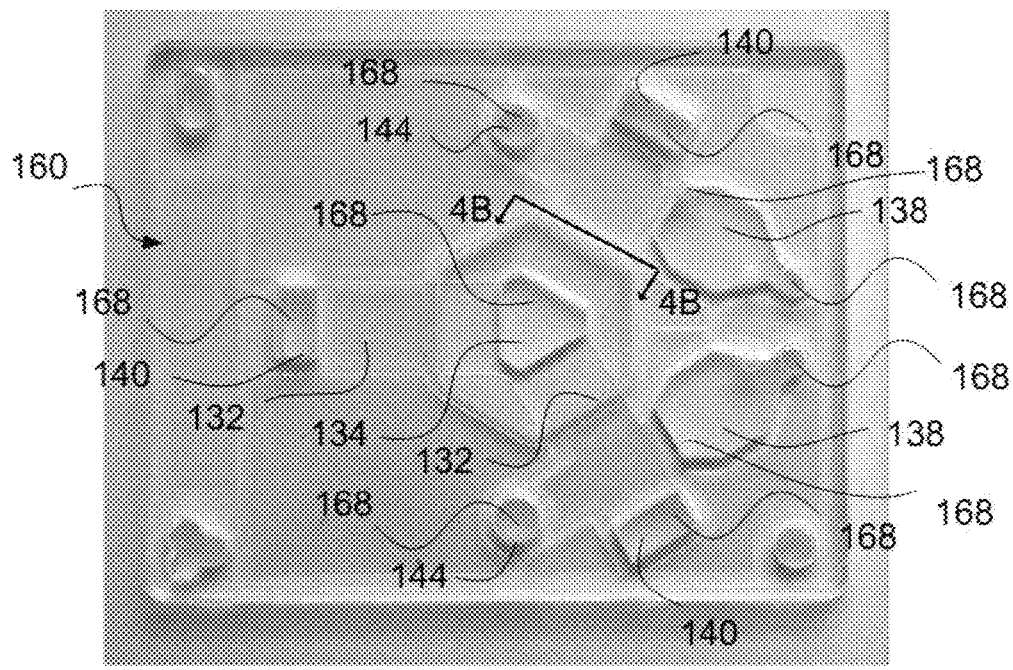
FIG. 14A is a top view of a photograph of a gel cassette for use with the apparatus of FIGS. 13A and 13B.
Figure 14B:
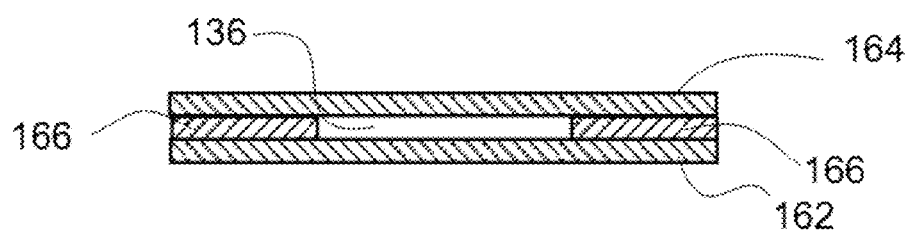
FIG. 14B is a schematic cross-sectional drawing of the cassette of FIG. 14A.

FIGS. 13A-13C illustrate a second exemplary embodiment of an apparatus 130 for separating particles. Portions of apparatus 130 that correspond in function to portions of apparatus 30 are indicated with like reference numerals incremented by 100. In the illustrated embodiment, separation arms 132 are disposed between a base plate 162 and a top plate 164 (FIG. 14). Access apertures 168 (FIG. 14A) define portions of central reservoir 134, loading reservoirs 138, and buffer chambers 140 and 144. The depths of central reservoir 134, loading reservoirs 138, and buffer chambers 140 and 144 is thus defined in part by the thickness of top plate 164 (FIG. 14B). In the illustrated embodiment, central reservoir 134, loading reservoirs 138, and buffer chambers 140 and 144 are all deeper than the thickness of separation medium 136 (FIG. 14B).

In the illustrated embodiment, central reservoir 134 is of a generally triangular shape, with rounded or trimmed corners 135. Central reservoir 134 is shaped to minimize any potential distortions to the electric field used to move sample particles in arms 132.

In the illustrated embodiment of FIGS. 13A and 13B, loading reservoir 138 has a relatively wider middle portion 180. However, loading reservoir 138 can be of the same width as separation arms 132, as shown in FIG. 13C. In FIGS. 13A and 13B, tapered portion 182 narrows from middle portion 180 toward an injection surface 184 on separation arm 132. A second tapered portion 186 narrows from middle portion 180 toward an electrode chamber 188 for receiving a loading electrode, shown schematically as 146B. A separate loading buffer chamber 144 receives loading electrode 146A.

In some embodiments, loading of sample into the separation arms is enhanced. For example, in the embodiment illustrated in FIGS. 13A and 13B, loading reservoir 138 has a greater depth than the thickness of separation medium 136. Providing a loading reservoir 138 with a height greater than the thickness of separation medium 136 allows the sample volume to be increased, without making the surface area required for loading reservoir 138 unduly large. In other embodiments, as depicted in FIG. 13C, sample loading can be enhanced with the inclusion of electrical streamlines 183. Electrical streamlines 183 are in the same plane as the gel of separation arms 132, and help constrain the sample to a narrow physical window during injection. When used, a voltage is applied from the agarose dam 181 and electrical streamlines 183 to the electrode across the separation arm 132. When used to load nucleic acids, for example, the configuration in FIG. 13C reduces loading losses due to nucleic acid spreading upon injection. Such techniques are especially useful when evaluating high value samples, such as forensic crime samples, where any nucleic acid loss can skew the results.

With reference to FIGS. 14A and 14B, in one embodiment a cassette 160 for use with apparatus 130 has a base plate 162 and a top plate 164. Plates 162, 164 may be made of any suitable non-electrically-conductive material, for example plastic, acrylic or glass. In embodiments in which temperature is used as the mobility altering field, at least one of base plate 162 and top plate 164 should be made from a material with good thermal conductivity, for example, glass.

Base plate 162 may be secured to top plate 164 in any suitable manner, for example by being integrally formed therewith, clamped thereto, secured thereto with an acceptable adhesive, or the like. In the illustrated embodiment of FIGS. 14A and 14B, base plate 162 is secured to top plate 164 using a layer of pressure sensitive adhesive 166. Pressure sensitive adhesive 166 maintains the spacing between base plate 162 and top plate 164. Pressure sensitive adhesive is cut to provide the desired configuration of separation medium 136. That is, portions of pressure sensitive adhesive 166 are removed where pressure sensitive adhesive 166 would otherwise interfere with separation arms 132, central reservoir 134, loading reservoir 138, electrode buffer chambers 140, loading buffer chambers 144, or the like. For example, where the separation medium is a gel such as polyacrylamide or agarose, pressure sensitive adhesive 166 can be cut to the desired shape, bonded between base plate 162 and top plate 164, and the gel can be poured in each separation arm 132. Where the separation medium is relatively thin, e.g. 100 μm, capillary action will draw the gel between plates 162, 164, and the gel will take on the shape defined by pressure sensitive adhesive 166. Access apertures 168 are provided in the top plate to provide access to loading reservoirs 138, central reservoir 134, to enable electrodes 140, 142, 146 to be inserted into the corresponding buffer chambers. In embodiments in which the gel is sufficiently thick that capillary action will not prevent the gel from entering loading reservoirs 138, central reservoir 134, electrode buffer chambers 140 or loading buffer chambers 144, suitable gel dams or other structures can be used to prevent the gel from flowing into these regions when being poured.

In the illustrated embodiment, the thickness of separation medium 136 is defined by the thickness of the layer of pressure sensitive adhesive 166. Separation medium 136 may have any desired thickness. In some exemplary embodiments, separation medium 136 is 100 μm thick. The thickness of separation medium 136 could be increased to increase the sample capacity of cassette 160. However, if separation medium 136 is made too thick, separation medium 136 will take longer to heat and cool (i.e. the thermal response time of separation medium 136 will be increased), which may be undesirable in some embodiments that use temperature as the mobility altering field. The thermal relaxation time of a separation arm filled with separation medium approximately 100 μm thick has been found to be on the order of ~200 ms in one exemplary embodiment. If separation medium 136 is made too thin, the capacity of cassette 160 may become undesirably low. The capacity of cassette 160 is determined by the volume of a sample to be loaded, the mass of charged target particle (e.g. DNA) to be loaded, and the concentration of electrically charged species (including salts) in the sample.

In some embodiments, a filter gel can be used upstream of a separation medium to reduce the level of contaminants present in a sample before target particles are subjected to separation, as well as to increase the capacity of the separation medium. The capacity of an apparatus can depend on all of the volume and salinity of a sample and the amount of charged target and contaminant particles present in a sample. That is, the capacity of an apparatus may be limited by any of the volume of a sample (a sample which is too large in volume may not be loaded), the salinity of a sample (i.e. the presence of too many ions may interfere with electrophoresis if the salinity of the sample is too high), or the amount of target particle in a sample (e.g. the presence of too much nucleic acid in the sample, whether target or contaminating sequence, may interfere with electrophoresis). A filter gel as described below allows for a larger volume of sample to be loaded, allows for the removal of excess ions in the sample during loading, and/or allows for the removal of particles similar in nature to the target particle but which do not interact as strongly with the immobilized agent in the filter gel (e.g. for the removal of nucleic acids that have a sequence that is not similar to a target nucleic acid). In use, a filter gel can be positioned upstream of the separation apparatus, so that particles can be first loaded into the separation gel, and then loaded onto the separation apparatus.

A filter gel is a separation medium (for example agarose or polyacrylamide gel) that has an agent immobilized therein. The agent is selected to have a binding for target particles of interest (e.g. oligonucleotides having a particular sequence). A sample is injected into the filter gel by application of an electric field under conditions such that the target particles of interest bind to the immobilized agent (or alternatively the sample could be mixed with the filter gel when the filter gel is poured). Under the influence of the electric field, contaminating particles that do not bind to the agent pass through the filter gel. In some embodiments, the contaminating particles can be removed via an exhaust gel downstream of the filter gel during sample loading, so that contaminating particles do not enter the separation medium.

After contaminating particles have passed through the filter, conditions are changed so that the target particles do not bind the agent (e.g. the temperature is raised), and an electric field is applied to inject the target particles from the filter gel into the separation medium. A filter gel can be used together with any apparatus for conducting electrophoresis to reduce the level of contaminants present and/or to increase the capacity of the apparatus. For example, a filter gel could be provided upstream of a conventional electrophoresis gel used to separate oligonucleotides based on size.

FIGS. 15A, 15B, 15C and 15D illustrate a third exemplary embodiment of an apparatus 230 for separating particles. Portions of apparatus 230 that correspond in function to portions of apparatus 30 are identified by like reference numerals incremented by 200. In the illustrated embodiment, loading reservoir 238 is thicker than the separation medium in separation arms 232. A filter gel 300 is provided at the end of loading reservoir 238 adjacent separation arm 232 (the edge of the filter gel 300 is indicated by a dashed line). Filter gel 300 includes a plurality of immobilized agents that bind to target particles in sample 248. In some embodiments, the plurality of immobilized agents are all the same agent. During injection of sample 248 into separation arm 232, target particles can be bound to the immobilized agents in filter gel 300 while contaminating particles are washed through filter gel 300. After sample 248 has been loaded, target particles can then be eluted for injection into separation arm 232 in any suitable manner In some embodiments, target particles are bound to the immobilized agents in filter gel 300 at a relatively low temperature, and the target particles are eluted by increasing the temperature to a level where the target particles do not bind significantly to the immobilized agents. In some embodiments, separation arm 232 includes the same agent as filter gel 300. In some embodiments, separation arm 232 includes a different agent than filter gel 300. In some embodiments, the agent in filter gel 300 has a stronger binding for both the target particle and non-target particles than the agent in separation arms 232. In some embodiments, separation arm 232 does not include an agent, while filter gel 300 does include an agent.

In some embodiments, temperature regulators such as heating and/or cooling units are provided adjacent to the medium to facilitate temperature control. In some embodiments, one or more Peltier elements are provided to adjust the temperature of the separation medium. In some such embodiments, the Peltier elements are positioned adjacent to the base plate (e.g. base plate 162) and the base plate is made from a thermally conductive material, e.g. glass. In some embodiments, a controller is provided to regulate the operation of the Peltier elements and/or the electrodes. Peltier elements can be used to heat and/or cool the separation medium, depending on the desired application.

In some embodiments, including the illustrated embodiment of FIGS. 15A, 15B, 15C and 15D, two Peltier elements 202, 204 (shown only in FIGS. 15C and 15D) are provided adjacent separation arm 232 and filter gel 300, beneath the base plate of the gel cassette (not shown). Peltier elements 202, 204 are independently operable; that is, the temperature of each of Peltier elements 202 and 204 can be separately controlled. In some embodiments, a controller is provided to control the operation of Peltier elements 202, 204 and/or electrodes 242, 304 and/or 246A/246B (the electrodes are schematically labeled as the letters A, B and C (electrodes 242), F (304), D (246A) and E (246B) in FIG. 15A). In some embodiments, including the illustrated embodiment, Peltier elements 202, 204 abut one another within (in the illustrated embodiment, at approximately the midpoint of) the width of separation arm 232. To inject sample 248 into separation arm 232, an electric field is applied across loading electrodes 246A and 246B (or, as described below, electrodes 246A and 304) Initially, the temperature of Peltier element 202, which is adjacent filter gel 300, is maintained at a low temperature at which the target particle binds strongly to the immobilized agent (e.g. a temperature below the melting temperature of the target particle-agent duplex). Contaminating particles do not bind to the immobilized agent, or bind the immobilized agent to a lesser extent than the target particles. Consequently, contaminating particles can be washed through the filter gel 300, while the target particles are stacked at approximately the interface between loading reservoir 238 and filter gel 300. This step can be described as "filter injection".

After sample 248 has been loaded on filter gel 300, the temperature of Peltier element 202 can be increased to a level at which the target particles bind poorly or not at all to the immobilized agent (e.g. a temperature above the melting temperature of the target particle-agent duplex). Continued application of an electric field across loading electrodes 246A and 246B will cause the target particles to be injected into separation arm 232. This step can be described as "hot injection" of the target particles.

In some embodiments, including the illustrated embodiment, separation arm 232 also includes an immobilized agent that binds to the target particles. Target particles can be stacked in the separation medium prior to the application of electric fields to separate the particles by providing a temperature gradient in the path of travel of particles entering the separation medium. For example, a temperature profile can be created across the width of the separation arm, such that target particles entering the separation medium from the filter gel are at a high temperature at which the target particles bind poorly or not at all to the immobilized agent, while a point within the path of travel of the target particles entering the separation arm downstream of the filter gel is at a relatively low temperature at which the target particles are likely to remain bound to the immobilized agent. Target particles will tend to bind to the immobilized agent at the point where the temperature drops, thereby stacking the target particles within the separation medium.

For example, in the illustrated embodiment, a second Peltier element 204 is provided adjacent separation arm 232 and in the path of travel of particles being injected into separation arm 232. Peltier elements 202 and 204 are positioned so that the interface between the two elements is at a convenient location relative to the width of separation arm 232. In some embodiments, the interface between Peltier elements 202 and 204 is located at approximately the midpoint of the width of separation arm 232. Peltier elements 202 and 204 can be spaced apart. In some embodiments, Peltier elements 202 and 204 are positioned close together, so that target particles can be stacked in a narrow band as described below.

Stacking of target particles within separation arm 232 may be done by filter injection of the target particles in filter gel 300 as described above, followed by hot injection of the target particles into separation arm 232 by increasing the temperature of Peltier element 202. During the hot injection step, the temperature of Peltier element 204 is maintained at a low temperature at which the target particles bind effectively to the immobilized agent in separation arm 232 (e.g. at a temperature below the melting temperature of the target particle-agent duplex). After the target particles have been stacked in separation arm 232, the temperature of Peltier element 202 can be reduced and the temperature of Peltier element 204 can be increased so that the temperature of both elements 202 and 204 is approximately the same, and is at a level at which the electric fields are to be applied to electrodes 242 (represented by the letters A, B and C in FIG. 15A).

In some embodiments, loading reservoir 238 includes exhaust arms 302, as in the illustrated embodiment of FIGS. 15A, 15B, 15C and 15D. The exhaust arms are provided to receive contaminants flowing through the filter gel during sample loading. Exhaust arms allow contaminants to be removed from the sample and from the filter gel without allowing the contaminants to enter the separation medium. By applying an electric field across both the filter gel and the exhaust arms, contaminants that do not bind to the immobilized agent within the filter gel can be removed, without contaminating the separation medium.

In some embodiments, exhaust arms 302 are filled with the same gel as filter 300. In some embodiments, the gel filling exhaust arms 302 includes an immobilized agent therein. Exhaust arms 302 are coupled to a loading electrode 304 (represented schematically as the letter F in FIG. 15A) which sits in a loading electrode buffer chamber 306. In the illustrated embodiment, two exhaust arms 302 extend outwardly from filter gel 300. Exhaust arms 302 can be provided with any desired configuration. In some embodiments, exhaust arms 302 can conveniently extend out of the plane of the separation medium to remove contaminant particles.

In the illustrated embodiment, exhaust arms 302 contact filter gel 300 at a point vertically above the surface of loading reservoir 238. In this way, an electric field can be applied between electrodes 246A and 304 to remove contaminants during stacking of target particles in filter gel 300. Such contaminants do not enter separation arm 232, as the contaminants pass through exhaust arms 302 to buffer chamber 306.

Figure 16:
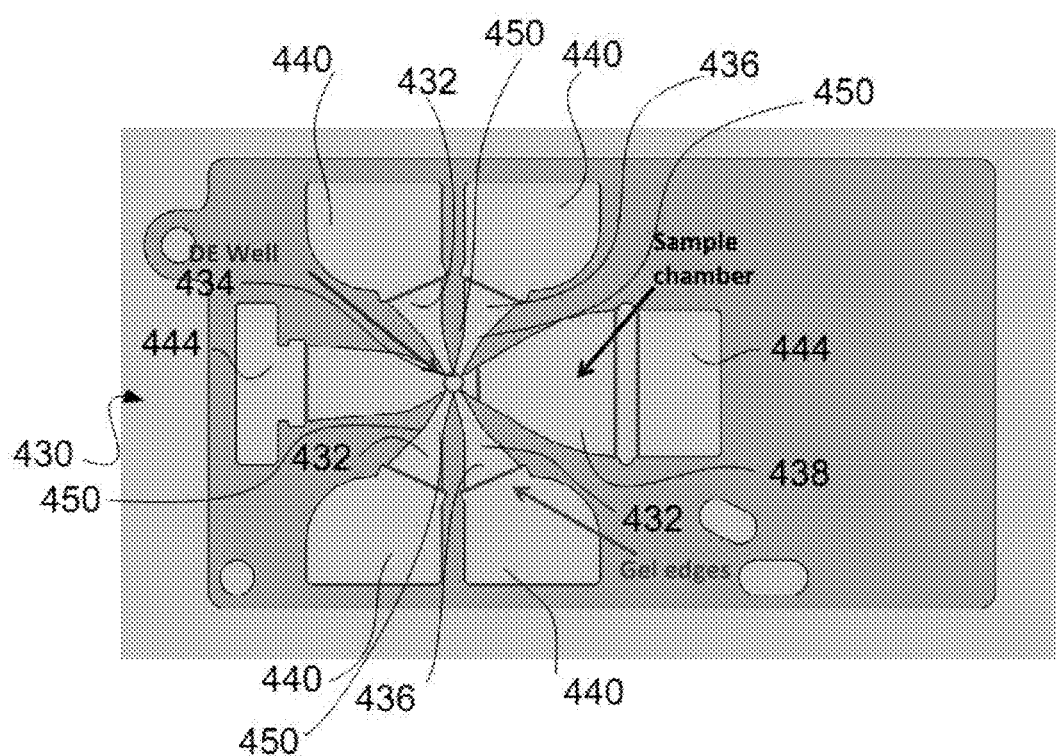
FIG. 16 is a top view of a further embodiment of an example apparatus for separating particles having four tapered separation arms.

FIG. 16 shows a further embodiment of an example apparatus 430 for separating particles. Portions of apparatus 430 that correspond in function to portions of apparatus 30 are indicated by like reference numerals incremented by 400. Apparatus 430 has four separation arms 432. The separation arms 432 of apparatus 430 are tapered, that is, the width of separation arms 432 at a point proximate central reservoir 434 is narrower than the width of separation arms 432 at a point distal from central reservoir 434. By varying the width of separation arms 432 along their length, the magnitude of current density at any given point along the length of separation arms 432 can be varied. That is, due to conservation of electric charge, the amount of charge passing through a cross-section taken at any point along the length of separation arm 432 must be the same as the amount of charge passing through a cross-section taken at any other point along the length of separation arm 432. Thus, the amount of current passing through a cross-section at which separation arm 432 is relatively narrower will be larger than the amount of current passing through a cross-section at which separation arm 432 is relatively wider. The temperature within the separation medium can be varied based on the amount of current passing through a cross-section at a particular point within the separation arm 432.

In some embodiments, including the illustrated embodiment, the tapered separation arms 432 have a point at which the angle of taper outwardly from a center line running along the length of the separation arms increases slightly, indicated at 450. The presence of a point or region 450 at which the angle of taper changes can help to enhance the effects of changes in temperature and electric field strength, resulting in a sharper separation of particles.

The creation of varying electric field strengths or temperatures within the tapered separation arms 432 allows for the creation of equilibrium points for particles with certain characteristics within separation arms 432. For example, for particles that have a mobility that varies with both electric field strength and temperature, by selection of appropriate conditions, at a certain point along the length of separation arms 432, the net motion of a target particle in one cycle can change from net negative (i.e. away from central reservoir 434) to net positive (i.e. toward central reservoir 434). The target particle will tend to remain at that equilibrium point within separation arm 432. After other particles have been moved out of separation arms 432, the operating conditions can be adjusted so that the target particle experiences net positive motion towards central reservoir 434. Target particles can then be removed from central reservoir 434 and subjected to further analysis.

For example, the illustrated embodiment of FIG. 16 can be used to separate oligonucleotides such as DNA based on size. The oligonucleotides can be loaded on the separation arms 432 using sample chamber 438 by injecting oligonucleotides through central reservoir 434 by the application of an electric field. The mobility of DNA through the separation medium varies with both temperature and electric field strength. The temperature dependence and electric field strength dependence of the mobility of larger DNA particles are both greater than the temperature dependence and electric field strength dependence of the mobility of shorter DNA particles. These differences can be used to separate DNA based on length.

Electric fields can be applied to cause net movement of the DNA in a selected direction based on the change in mobility of the DNA with changes in electric field strength. For example, the DNA can be caused to move inwardly by the application of a high positive voltage to three electrodes positioned at the distal ends of the separation arms and a low voltage to the fourth electrode positioned at the distal end of the separation arm) in the manner described above. Such electric fields can be termed focusing fields (because DNA tends to be focused in to central reservoir 434). The DNA can alternatively be caused to move outwardly by the application of a high positive voltage to one electrode and a low voltage to the remaining three electrodes at the distal end of the separation arms. Such electric fields can be termed defocusing fields (because the DNA tends to move outwardly, away from central reservoir 434).

Application of the electric fields also causes a change in temperature of the separation medium. Because the separation arms have a tapered shape, a larger amount of current will pass through a cross section of the separation arm taken nearer to the central reservoir 434 than farther away from the central reservoir 434. Consequently, the amplitude and phase of the thermal oscillations established by the application of the electric fields change along the length of the separation arms. Because DNA mobility also depends on both temperature and electric field strength, the net movement of the DNA along the length of the separation arm will depend on the relative dominance of changes in mobility in response to temperature oscillations within the separation medium versus changes in mobility in response to changes in electric field strength. When applying defocusing fields, if conditions are chosen so that the phase of the thermal oscillations is out of phase with the defocusing electric fields towards the distal portion of the separation arms (e.g. due to a high thermal lag time for the gel to be heated due to Joule heating), some molecules will reach an equilibrium position, at which net movement toward the distal end of the separation arm caused by changes in mobility due to the changes in electric field strength will be equal to net movement toward central reservoir 434 caused by changes in mobility due to changes in temperature within the separation medium. That is, the net movement due to changes in mobility caused by changes in electric field strength will be in one direction (distally away from central reservoir 434) while net movement due to changes in mobility caused by changes in temperature can be in the opposite direction (i.e. toward central reservoir 434). Conditions can be selected so that the equilibrium position for DNA having a particular size of interest is inside the separation arms, while DNA having other sizes is washed out of the distal ends of the separation arms.

In alternative embodiments, a temperature gradient can be established using heating or cooling units positioned adjacent to any shaped separation arm (e.g. a rectangularly-shaped separation arm) to create equilibrium points in a similar manner.

In some embodiments, the separation of one particle from other similar particles is enhanced by applying a wash field superimposed over the electric fields used to separate particles. In some embodiments, the wash field is an electric field. In some embodiments, the wash field is provided by applying the electric field in one configuration of the cycle for a longer period of time (a washing time) than the electric field is applied in the other n–1 configurations of the cycle. The temperature and duration for which the wash field is applied can be adjusted to effect separation of particles based on the differences in of the particles for an immobilized agent. The washing field essentially causes a departure from the condition that the net motion for particles whose mobilities do not vary under the influence of the mobility altering field is zero.

Using an exemplary embodiment having three separation arms, Table 6 summarizes an exemplary voltage pattern that could be used to separate particles with a washing field using the exemplary embodiment illustrated in FIG. 11. In the exemplary embodiment described below, the mobility altering field is provided by Joule heating caused by the electric field that provides the driving field. In this embodiment, the temperature of the separation medium is maintained at a desired base temperature, e.g. in the range of 40° C. to 60° C., for example using a Peltier element as described above, and the heat produced by the electric field is sufficient to produce the desired increase in temperature. Because of Joule heating due to the passage of current through the separation medium, the temperature within the separation medium will generally be higher than the base temperature set by a temperature controller (e.g. the temperature in the separation medium will generally be higher than the temperature of the Peltier element).

TABLE 6

Exemplary voltage pattern for embodiment with three separation arms providing a washing field.

| Step | Electrode 42A | Electrode 42B | Electrode 42C | Duration |
|---|---|---|---|---|
| 1 | H | L | H | 1 second |
| 2 | L | H | H | 1 second |
| 3 | H | H | L | 1 second |
| 4 | H | H | L | 0.5 second |

In the exemplary embodiment summarized in Table 6, step 4 provides the washing electric field to the separation arms.

Figure 17:
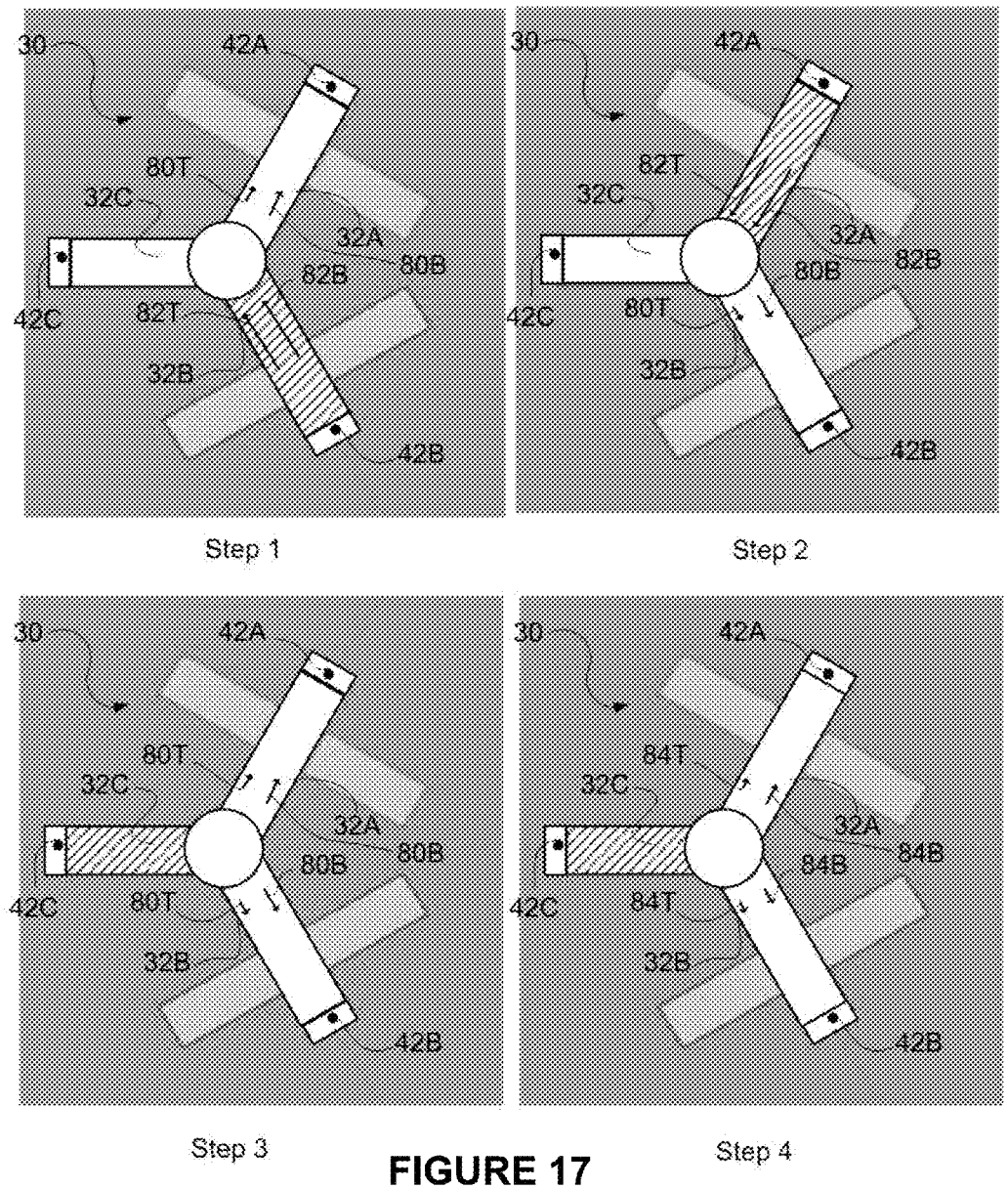
FIG. 17 shows the movement of a hypothetical particle under applied electric fields in an exemplary embodiment using a wash field.

With reference to FIG. 17, the movement of an exemplary pair of oligonucleotide molecules, a target molecule having a perfect sequence match to an oligonucleotide probe immobilized within the separation medium, and a background molecule having a single base mismatch to an oligonucleotide probe immobilized within the separation medium, under the applied electric fields is described. For purposes of the exemplary description below, a mixture of target and background molecules is loaded on each of separation arms 32A and 32B and injected into the separation medium. No sample is loaded on separation arm 32C, which is a washing arm as explained below.

In step 1, separation arms 32A and 32C are regions of low electric field strength (the voltages applied at electrodes 42A and 42C are high). Arm 32B is a region of high electric field strength, as indicated by diagonal shading. Due to conservation of current, the amount of heat being generated by Joule heating in the separation medium in arm 32B will be 4/greater than the amount of heat being generated by Joule heating in separation arms 32A and 32C, where I is the current flowing through each of separation arms 32A and 32C. Thus, arm 32B will also be at a higher temperature than arms 32A and 32C. Both the target and background molecules in separation arm 32A will move in a direction away from central well 34. Because the probability that the background molecules will be bound to the immobilized agent is less than the probability that the target molecules will be bound to the immobilized agent, on average the background molecules in separation arm 32A will move farther during this step than the target molecules in separation arm 32A. The magnitude and direction of this movement are indicated schematically by arrows 80T and 80B in FIG. 17.

In arm 32B, the temperature is higher than in arm 32A. Both the target molecule and the background molecule have a mobility within the medium that approaches the unbound mobility, i.e. the probability that either the target molecule or the background molecule will bind to the immobilized agent is low. Both the target molecule and the background molecule will move approximately the same distance toward central reservoir 34, as indicated schematically by arrows 82T, 82B. Because arm 32B is a region of high electric field strength, the distance travelled by both the target molecule and the background molecule will be greater than it would be at low field strength.

In step 2, separation arms 32B and 32C are regions of low field strength, while separation arm 32A is a region of high field strength, as indicated by diagonal shading. Due to conservation of current, the amount of heat being generated by Joule heating in the separation medium in arm 32A will be 4/greater than the amount of heat being generated by Joule heating in separation arms 32B and 32C, where I is the current flowing through each of separation arms 32A and 32C. Thus, separation arm 32A will also be at a higher temperature than arms 32B and 32C. Both the target and background molecules in separation arm 32B will move in a direction away from central well 34. Because the probability that the background molecules will be bound to the immobilized agent is less than the probability that the target molecules will be bound to the immobilized agent, on average the background molecules in separation arm 32B will move farther during this step than the target molecules in separation arm 32B. The magnitude and direction of this movement are indicated schematically by arrows 80T and 80B in FIG. 17.

In arm 32A, the temperature is higher than in arm 32B. Both the target molecule and the background molecule have a mobility within the medium that approaches the unbound mobility, i.e. the probability that either the target molecule or the background molecule will bind to the immobilized agent is low. Both the target molecule and the background molecule will move approximately the same distance toward central reservoir 34, as indicated by arrows 82T, 82B. Because arm 32A is a region of high electric field strength, the distance travelled by both the target molecule and the background molecule will be greater than it would be at low field strength.

In step 3, separation arms 32A and 32B are regions of low field strength, while separation arm 32C is a region of high field strength, as indicated by diagonal shading. Due to conservation of current, the amount of heat being generated by Joule heating in the separation medium in arm 32C will be 4/greater than the amount of heat being generated by Joule heating in separation arms 32A and 32B, where I is the current flowing through each of separation arms 32A and 32B. Thus, arm 32C will be at a higher temperature than arms 32A and 32B. Both the target and background molecules in separation arms 32A and 32B will move in a direction away from central well 34. Because the probability that the background molecules will be bound to the immobilized agent is less than the probability that the target molecules will be bound to the immobilized agent, on average the background molecules in separation arms 32A and 32B will move farther during this step than the target molecules in separation arms 32A and 32B. The magnitude and direction of this movement are indicated schematically by arrows 80T and 80B in FIG. 17.

In step 4, conditions remain the same as in step 3 for a further period of time (a washing time). Typically, the washing field applied at step 4 will be applied for a shorter period of time than the other configurations of the cycle. In this example, the electric field configuration of step 4 is applied for 0.5 seconds, whereas the electric fields of steps 1, 2 and 3 are applied for 1 second. Both the target and background molecules in separation arms 32A, 32B take a further step away from central reservoir 34, as illustrated by arrows 84T, 84B in FIG. 17. Because the time for which the washing field is applied is only ½ as long as the time for which the low electric field is applied in step 3, the distance traveled by both the target and background molecules in step 4 is on average only ½ as far as the distance traveled in step 3.

In some embodiments in which a wash field is to be applied, sample is loaded on only n−1 of the n separation arms. That is, no sample is loaded on one of the separation arms. For example, in an embodiment having three separation arms, sample is loaded on only two of the separation arms. The arm in which no sample is loaded can be referred to as a "washing arm". In the exemplary embodiment described above, application of the wash field moves negatively charged particles in two (i.e. n−1 where n is 3) of the separation arms away from the central reservoir (as described with reference to separation arms 32A and 32B above). Any negatively charged particles present in separation arm 32C will move towards the central reservoir under the influence of the wash field. Thus, negatively charged particles, including the background molecules, could experience net motion towards central reservoir 34 under the application of a wash field. Loading sample on separation arm 32C could lead to contamination of the target molecules recovered in central reservoir 34 with background molecules. In the illustrated embodiment, separation arm 32C is a wash arm. No sample is loaded on arm 32C. This avoids a risk that the washing field will cause negatively charged particles to move from arm 32C to central reservoir 34.

Where a component (e.g. a power supply, electrode, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

EXAMPLES

Example 1

Separation of KRAS Homoduplex DNA from KRAS Heteroduplex DNA

Figure 18:
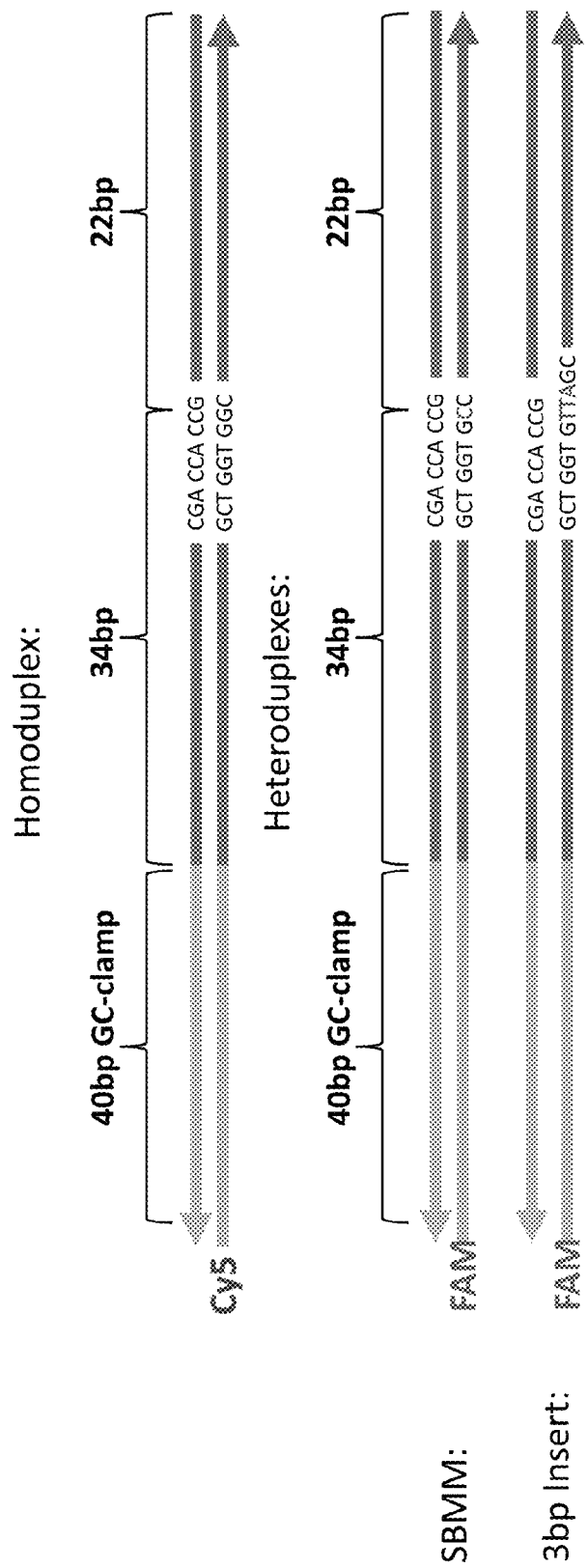
FIG. 18 shows homoduplexed and heteroduplexed KRAS nucleic acids used in Example 1.

KRAS homoduplexed DNA oligos and heteroduplexed DNA oligos were obtained from a commercial supplier (Integrated DNA Technologies, Coralville, Iowa). Each oligo was approximately 96 base pairs in length and included a 40 bp GC-clamp. The duplexes for the experiment are depicted in FIG. 18. One oligo of each duplex (sense or anti-sense) was labeled with a fluorescent tag so that duplexes could be visualized during the separation (See FIG. 19).

The homoduplexes contained two complementary strands, the first strand has SEQ ID NO. 1: AGCGGGCG-GCGCGGGGCGCGGGCAGGGCG-GCGGGGGCGGGCTGA CTTATATTTGAACACCAT-CAACCTCGACCACCGCATCCGTTCTCACGGAACTG; the complementary strand was SEQ ID NO. 2: TCGCCCGC-CGCGCCCCGCGCCCGTCCCG CCGCCCCCGC-CCGACTGAATATAAACTTGTGGTAGTTG-GAGCTGGTGGCGTAGGCAAGAG TGCCTTGAC. The homoduplexes were labeled with Cy5, thus they were observable as red fluorescence during the separation. The heteroduplexes comprised either a single base mismatch (SBMM) at G13 or a three-base insert (3 bp Insert) at G13 (See FIG. 18). The SBMM sequences were SEQ ID NO. 3: AGCGGGCG-GCGCGGGGCGCGGGCAGGGCGGCG GGGGCGGGCTGACTTATATTTGAACAC-CATCAACCTCGACCACCGCATCCGTTCTCACGG AACTG, and the complementary strand except for the single base mismatch shown in FIG. 19, i.e., SEQ ID NO. 4: TCGC-CCGCCGCGCCCCGCGCCCGTCCCGCCGC-CCCCGCCCGA CTGAATATAAACTTGTGGTAGTTG-GAGCTGGTGCCGTAGGCAAGAGTGCCTTGAC. The 3 bp Insert sequences were SEQ ID NO. 5: AGCGGGCG-GCGCGGGGCGCGGGCAGGG CGGCGGGGGCGGGCTGACT-TATATTTGAACACCATCAACCTCGAC-CACCGCATCCGTTCT CACGGAACTG, and the complementary strand except for the three base insert shown in FIG. 19, i.e., SEQ ID NO. 6: TCGCCCGCCGCGCCCCGCGC-CCGTCCCGCCGCCCCCGCCCG ACTGAATATAAACT-TGTGGTAGTTGGAGCTGGTGTTAGCG-TAGGCAAGAGTGCCTTGAC. Both types of heteroduplexes were labeled with FAM, and were observable as green fluorescence during the separation.

A sample including a mixture of the homoduplexes and the SBMM was loaded onto a SCODA separation chip including a polyacrylamide gel without agents (Boreal Genomics, Los Altos, Calif.). The extraction was run with variable times and temperatures as described in the tables below. The buffer used was 1×TB (0.089 M tris base+0.089 M boric acid) and 3.5 M Urea with a pH of 8.41 and a conductivity of 0.55 mS/cm.

The sample was injected onto the separation medium using 500 V at 20° C. with 70 mC accumulated charge. The sample then underwent a 5-block SCODA separation, detailed pictorially in FIG. 19. The times, voltages, and temperatures used during the separation are shown in tables 7 to 11 below.

Figure 20:
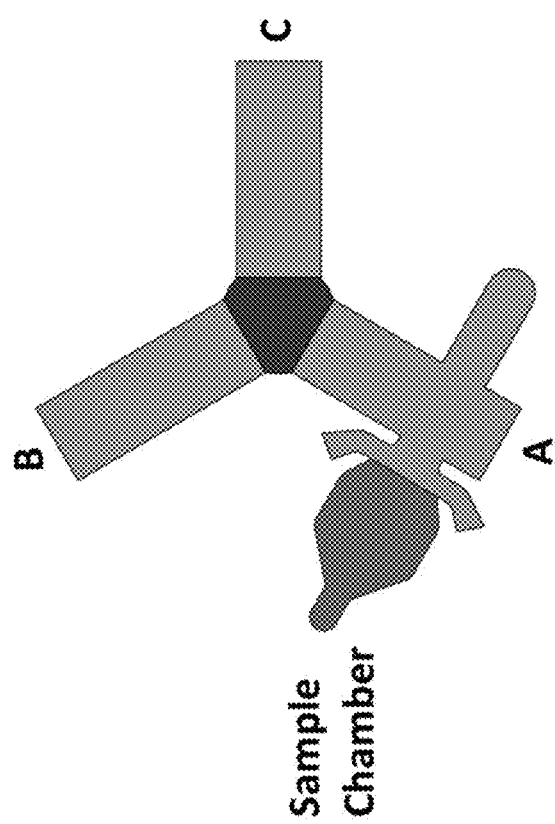
FIG. 20 shows the 3-arm cartridge configuration used in Examples 1 and 2.

The configuration of electrodes A, B, and C, referenced in the Tables, is depicted in FIG. 20.

TABLE 7

54° C. SCODA block with no wash; 30cycles × 6.9 sec/cycle; total duration 3:27 min.

| | Voltage at Electrode/V | | |
|---|---|---|---|
| Time/ms | A | B | C |
| 2000 | 0 | 900 | 0 |
| 300 | — | — | — |
| 2000 | 0 | 0 | 900 |
| 300 | — | — | — |
| 2000 | 900 | 0 | 0 |
| 300 | — | — | — |

TABLE 8

56° C. SCODA block with no wash; 30 cycles × 6.9 sec/cycle; total duration 3:27 min.

| | Voltage at Electrode/V | | |
|---|---|---|---|
| Time/ms | A | B | C |
| 2000 | 0 | 900 | 0 |
| 300 | — | — | — |
| 2000 | 0 | 0 | 900 |
| 300 | — | — | — |
| 2000 | 900 | 0 | 0 |
| 300 | — | — | — |

TABLE 9

58° C. SCODA block with no wash; 30 cycles × 6.9 sec/cycle; total duration 3:27 min.

| | Voltage at Electrode/V | | |
|---|---|---|---|
| Time/ms | A | B | C |
| 2000 | 0 | 900 | 0 |
| 300 | — | — | — |
| 2000 | 0 | 0 | 900 |
| 300 | — | — | — |
| 2000 | 900 | 0 | 0 |
| 300 | — | — | — |

TABLE 10

60° C. SCODA block with 1.5 s wash; 75 cycles × 8.4 sec/cycle; total duration 10:30 min.

| | Voltage at Electrode/V | | |
|---|---|---|---|
| Time/ms | A | B | C |
| 2000 | 0 | 900 | 0 |
| 300 | — | — | — |
| 2000 | 0 | 0 | 900 |
| 300 | — | — | — |
| 3500 | 900 | 0 | 0 |
| 300 | — | — | — |

TABLE 11

60° C. SCODA block with no wash; 90 cycles × 6.9 sec/cycle; total duration 10:21 min.

| | Voltage at Electrode/V | | |
|---|---|---|---|
| Time/ms | A | B | C |
| 2000 | 0 | 900 | 0 |
| 300 | — | — | — |
| 2000 | 0 | 0 | 900 |
| 300 | — | — | — |
| 2000 | 900 | 0 | 0 |
| 300 | — | — | — |

Figure 19:
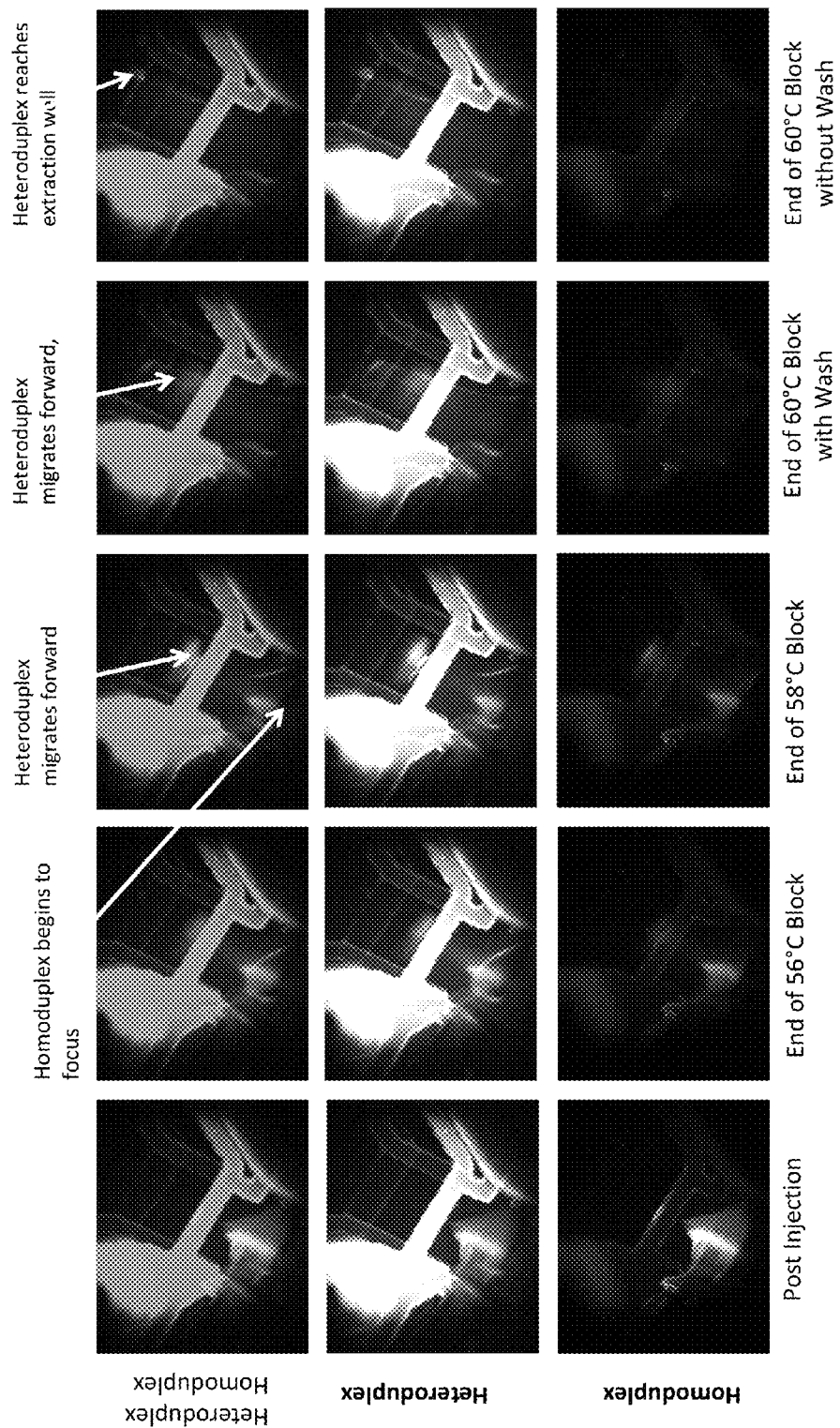
FIG. 19 shows fluorescent images of the separation and focusing of the heteroduplexed KRAS nucleic acids in Example 1.

Separation of the homoduplexes from the heteroduplexes, and subsequent recovery of the heteroduplexes can be seen in FIG. 19. FIG. 19 shows fluorescence images after various SCODA block described above in Tables 7 to 11. The top row of FIG. 19 is a real color image showing both red (homoduplex) and green (heteroduplex) fluorescence. The middle row is the green channel, and the bottom row the red. (The background fluorescence results from fluorescent moieties in the buffer.)

Separation of the homoduplexes from the heteroduplexes is evident in the center top image. With additional cycles and washing the homoduplexes are washed completely from the medium, as visible in the bottom row. At the same time the homoduplexes are removed from the medium, the heteroduplexes are focused into the extraction well. The focused heteroduplexes are visible as a bright spot in the upper right-hand quadrant of rightmost center-row image. Once the heteroduplexes were concentrated in the well, they were easily extracted. In a clinical sample, the extracted heteroduplexes could be sequenced to identify the nature of the mutation(s).

Example 2

Differential Stacking of KRAS Homoduplex DNA Versus KRAS Heteroduplex DNA During Injection Injection stacking can be used to the efficiency of loading, and thus, the yield of separated targets. Whereas in some instances the sample is injected at a constant temperature (see, e.g., the left-hand column of FIG. 19), it is also possible to inject a sample across a temperature transition, as shown in FIG. 21, to facilitate a higher yield of the target species, e.g., heteroduplexed nucleic acids.

Figure 21:
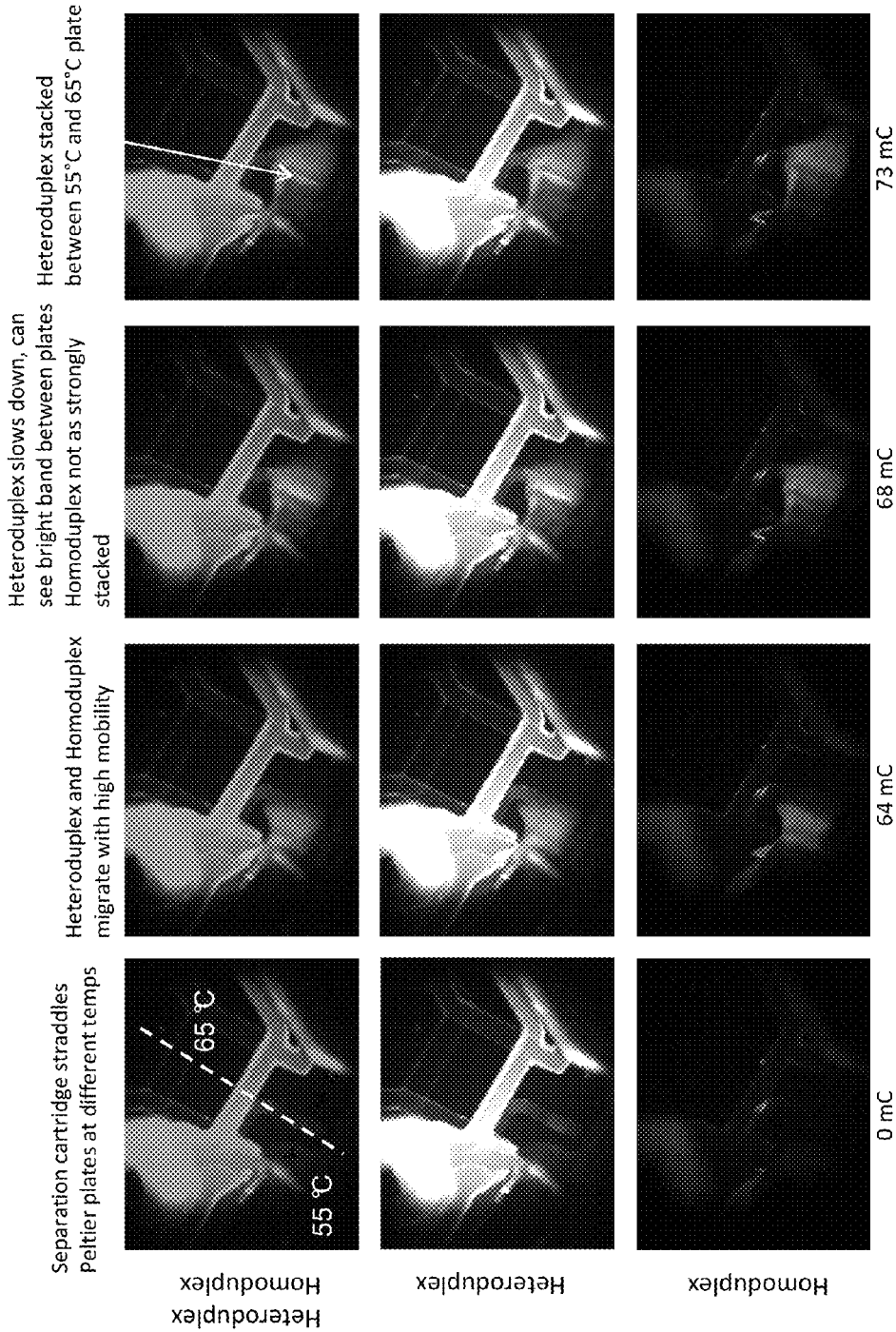
FIG. 21 shows stacking of heteroduplexed KRAS nucleic acids during loading. Stacking at loading results in more-effective loading, and thus, higher yields of isolated targets.

The dashed line in the upper left image of FIG. 21 shows the approximate location of a transition between two Peltier temperature plates under a separation cartridge similar to the one described in Example 1. Using this set-up it is possible to create a temperature step at the approximately the dashed line within the separation medium in the loading region. As discussed previously, and depicted in the mobility curves of FIGS. 9 and 10, the homoduplexes and the heteroduplexes have similar mobilities at temperatures of about 55° C. and less. When a sample having both heteroduplexes and homoduplexes is injected over the transition (i.e., dashed line) the heteroduplexes experience a sudden decrease in mobility, causing the heteroduplexes to be stacked up near the transition while the homoduplexes experience a similar, but less pronounced, stacking effect. Stacking of heteroduplexes results in a line of fluorescence visible in the upper rightmost image.

The stacking method disclosed in this Example can be used in addition to the separation techniques described in Example 1 in order to increase the recovery of heteroduplexes from a mixture. Stacking methods decrease the amount of heteroduplexes that are washed out of the focus fields during injection.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for separating a mixture of homoduplexed and heteroduplexed nucleic acids, comprising;
    loading a sample comprising a mixture of homoduplexed and heteroduplexed nucleic acids on a separation medium;
    applying a time-varying driving field to the separation medium; and
    applying a time-varying mobility varying field to the separation medium,
    thereby causing the homoduplexed nucleic acids to be separated from the heteroduplexed nucleic acids.

2. The method of claim 1, wherein the time-varying mobility varying field is temperature.

3. The method of claim 1, wherein the time-varying driving field comprises two non-collinear electric fields.

4. The method of claim 1, wherein the time-varying driving field comprises three non-collinear electric fields.

5. The method of claim 1, wherein the heteroduplexed nucleic acids comprise a first sequence and a second sequence, and either the first or the second sequence is known.

6. The method of claim 5, wherein the known sequence comprises a sequence that is associated with an oncogene.

7. The method of claim 6, wherein the oncogene is selected from a RAS-related oncogene, a p53-related tumor suppressor gene, and a WNT-related oncogene.

8. The method of claim 1, wherein the heteroduplexed nucleic acids comprise a first sequence and a second sequence, and neither the first nor the second sequence is known.

9. The method of claim 1, wherein the heteroduplexed nucleic acids comprise a first sequence and a second sequence and the first and second sequences are complementary strand paired except for a mutation selected from a nucleotide polymorphism, a base deletion, or a base insertion.

10. The method of claim 9, wherein the mutation is a single nucleotide polymorphism (SNP).

11. The method of claim 1, wherein the heteroduplexed nucleic acids comprise a first sequence and a second sequence and the first and second sequences are complementary strand paired except for a chemical modification selected from differential methylation or differential acetylation.

12. The method of claim 1, further comprising:
    obtaining a sample comprising nucleic acids;
    denaturing the nucleic acids to produce single-stranded oligomers; and
    reannealing the single-stranded oligomers to create a sample comprising a mixture of homoduplexed and heteroduplexed nucleic acids.

13. The method of claim 12, wherein the sample comprising nucleic acids comprises a dominant nucleic acid sequence comprising a majority of the nucleic acid sequences in the sample.

14. The method of claim 13, wherein at least a portion of the heteroduplexed nucleic acids comprises a pairing strand having the dominant nucleic acid sequence and a non-dominant nucleic acid sequence.

15. The method of claim 1, further comprising recovering the heteroduplexed nucleic acids.

16. The method of claim 15, further comprising amplifying the recovered heteroduplexed nucleic acids.

17. The method of claim 15, further comprising sequencing the recovered heteroduplexed nucleic acids.

18. The method of claim 12, wherein the sample comprising nucleic acids comprises PCR amplicons.

19. The method of claim 18, wherein the PCR amplicons comprise primers with a GC clamp region.

20. A method for determining a mutation in a nucleic acid sample, comprising:
    amplifying a plurality of non-identical nucleic acids in a sample to create a plurality of non-identical amplicons;
    denaturing and reannealing the non-identical amplicons to produce a sample comprising a mixture of homoduplexed and heteroduplexed nucleic acids;
    loading the sample comprising a mixture of homoduplexed and heteroduplexed nucleic acids on a separation medium;
    applying both a time-varying driving field and a time-varying mobility varying field to the separation medium, thereby causing the homoduplexed nucleic acids to be separated from the heteroduplexed nucleic acids; and
    recovering the heteroduplexed nucleic acids.

* * * * *

SEQUENCE LISTING

```
<160> NUMBER OF SEQ ID NOS: 6

<210> SEQ ID NO 1
<211> LENGTH: 97
<212> TYPE: DNA
<213> ORGANISM: Artificial sequence
<220> FEATURE:
<223> OTHER INFORMATION: Synthetic sequence

<400> SEQUENCE: 1
agcgggcggc gcggggcgcg ggcagggcgg cggggggcggg ctgacttata tttgaacacc      60
atcaacctcg accaccgcat ccgttctcac ggaactg                               97

<210> SEQ ID NO 2
<211> LENGTH: 97
<212> TYPE: DNA
<213> ORGANISM: Artificial sequence
<220> FEATURE:
<223> OTHER INFORMATION: Synthetic sequence

<400> SEQUENCE: 2
tcgcccgccg cgccccgcgc ccgtcccgcc gcccccgccc gactgaatat aaacttgtgg      60
tagttggagc tggtggcgta ggcaagagtg ccttgac                               97

<210> SEQ ID NO 3
<211> LENGTH: 97
<212> TYPE: DNA
<213> ORGANISM: Artificial sequence
<220> FEATURE:
<223> OTHER INFORMATION: Synthetic sequence

<400> SEQUENCE: 3
agcgggcggc gcggggcgcg ggcagggcgg cggggggcggg ctgacttata tttgaacacc      60
atcaacctcg accaccgcat ccgttctcac ggaactg                               97

<210> SEQ ID NO 4
<211> LENGTH: 97
<212> TYPE: DNA
<213> ORGANISM: Artificial sequence
<220> FEATURE:
<223> OTHER INFORMATION: Synthetic sequence

<400> SEQUENCE: 4
tcgcccgccg cgccccgcgc ccgtcccgcc gcccccgccc gactgaatat aaacttgtgg      60
tagttggagc tggtgccgta ggcaagagtg ccttgac                               97

<210> SEQ ID NO 5
<211> LENGTH: 97
<212> TYPE: DNA
<213> ORGANISM: Artificial sequence
<220> FEATURE:
```

```
<223> OTHER INFORMATION: Synthetic sequence

<400> SEQUENCE: 5
agcgggcggc gcggggcgcg ggcagggcgg cgggggcggg ctgacttata tttgaacacc    60
atcaacctcg accaccgcat ccgttctcac ggaactg                             97

<210> SEQ ID NO 6
<211> LENGTH: 100
<212> TYPE: DNA
<213> ORGANISM: Artificial sequence
<220> FEATURE:
<223> OTHER INFORMATION: Synthetic sequence

<400> SEQUENCE: 6
tcgcccgccg cgccccgcgc ccgtcccgcc gccccgccc gactgaatat aaacttgtgg    60
tagttggagc tggtgttagc gtaggcaaga gtgccttgac                         100
```